United States Patent [19]

Wenger et al.

[11] Patent Number: 4,859,229
[45] Date of Patent: Aug. 22, 1989

[54] 3-ARYLURACILS HAVING AN ETHER (THIO) CARBOMYLOXY OR SULPHOMYLOXY SUBSTITUENT ON THE AROMATIC MOIETY

[75] Inventors: Jean Wenger, Uster; Paul Winternitz, Greifensee, both of Switzerland

[73] Assignee: Hoffmann-La Roche Inc., Nutley, N.J.

[21] Appl. No.: 76,415

[22] Filed: Jul. 21, 1987

[30] Foreign Application Priority Data

Jul. 31, 1986 [CH] Switzerland ............. 3090/86
Jun. 12, 1987 [CH] Switzerland ............. 2207/87

[51] Int. Cl.$^4$ ............. A01N 43/54; C07D 239/55
[52] U.S. Cl. ............. 71/92; 544/309; 544/313; 544/314
[58] Field of Search ............. 544/309, 313, 314; 71/92

[56] References Cited

U.S. PATENT DOCUMENTS

| 3,235,357 | 2/1966 | Loux ............. | 544/313 |
| 3,235,360 | 2/1966 | Soboczenski ............. | 71/92 |
| 3,235,363 | 2/1966 | Luckenbaugh et al. ............. | 71/92 |
| 3,291,592 | 12/1966 | Evans ............. | 544/313 |
| 3,330,640 | 7/1967 | Luckenbaugh ............. | 544/314 |
| 3,352,862 | 11/1967 | Loux ............. | 544/313 |
| 3,360,520 | 12/1967 | Luckenbaugh et al. ............. | 544/309 |
| 3,436,207 | 4/1969 | Soboczenski ............. | 71/92 |
| 3,580,913 | 5/1971 | Lutz ............. | 544/309 |
| 3,838,128 | 9/1974 | Lutz ............. | 544/309 |
| 3,869,457 | 3/1975 | Lutz ............. | 544/309 |
| 4,266,056 | 5/1981 | Henrick et al. ............. | 544/314 |
| 4,358,591 | 11/1982 | Kohn ............. | 544/314 |
| 4,746,352 | 5/1988 | Wenger et al. ............. | 544/314 |

FOREIGN PATENT DOCUMENTS 1924232 12/1969 Fed. Rep. of Germany .
1035096 8/1962 United Kingdom .
1035097 12/1962 United Kingdom .
 968661 9/1964 United Kingdom .
 968666 9/1964 United Kingdom .
1000803 8/1965 United Kingdom ............. 544/309
1035098 7/1966 United Kingdom .
2043629 12/1978 United Kingdom .
2021098 11/1979 United Kingdom ............. 544/309

OTHER PUBLICATIONS

Chemical Abstract 94:192252u (1981).

Primary Examiner—Anton H. Sutto
Assistant Examiner—Cecilia Shen
Attorney, Agent, or Firm—Jon S. Saxe; Bernard S. Leon; Matthew Boxer

[57] ABSTRACT

The invention is concerned with 3-aryluracils of the formula

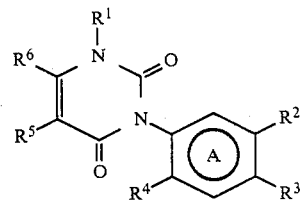

wherein $R^1$, $R^2$, $R^3$, $R^4$, $R^5$ and $R^6$ are as described herein, as well as salts thereof and their manufacture, weed control compositions which contain such compounds as the active substance and the use of the active substances or compositions for weed control. The invention is also concerned with herbicidally-active starting materials and weed control compositions containing these.

36 Claims, No Drawings

3-ARYLURACILS HAVING AN ETHER (THIO) CARBOMYLOXY OR SULPHOMYLOXY SUBSTITUENT ON THE AROMATIC MOIETY

BRIEF SUMMARY OF THE INVENTION

The present invention is concerned with heterocyclic compounds, namely 3-aryluracils of the formula

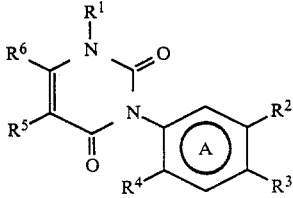

wherein
$R^1$ is hydrogen, $C_{1-4}$-alkyl, $C_{1-4}$-haloalkyl, formyl or $C_{2-6}$-alkanoyl,
$R^2$ is an ether group or a residue containing a (thio)carbonyloxy group or sulphonyloxy group, whereby this residue is directly attached to the benzene nucleus A via the oxygen atom,
$R^3$ is halogen or cyano,
$R^4$ is hydrogen or halogen,
$R^5$ is hydrogen, halogen or $C_{1-4}$-alkyl,
$R^6$ is $C_{1-4}$-alkyl or $C_{1-4}$-haloalkyl, or
$R^5$ and $R^6$ together are tri- or tetramethylene,
as well as salts of those compounds of formula I in which $R^1$ is hydrogen.

The compounds in accordance with the invention, i.e. the compounds of formula I as well as their salts, have herbicidal activity and are suitable as active substances of weed control compositions. Accordingly, the invention also embraces weed control compositions which contain compounds in accordance with the invention as the active substance, a process for the manufacture of these compounds as well as the use of such compounds or compositions for the control of weeds.

DETAILED DESCRIPTION OF THE INVENTION

In formula I "halogen" denotes fluorine, chlorine, bromine and iodine. The alkyl residues can be straight-chain or branched, and this also applies to the alkyl part of the haloalkyl and alkanoyl groups. A $C_{1-4}$-haloalkyl group can have one or more halogen atoms, with trifluoromethyl being an example of a multiply halogenated alkyl group.

In those formulae below in which an oblique line (/) appears, this denotes alternatives. Thus, for example, under the group

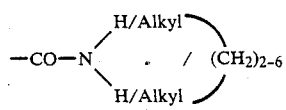

there are to be understood the following groups:
—CONH$_2$, —CONHalkyl, —CON(alkyl)$_2$ and

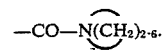

The invention is concerned with heterocyclic compounds, namely 3-aryluracils of the formula

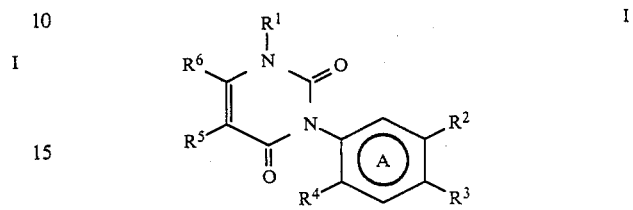

wherein
$R^1$ is hydrogen, $C_{1-4}$-alkyl, $C_{1-4}$-haloalkyl, formyl or $C_{2-6}$-alkanoyl,
$R^2$ is an ether group or a residue containing a (thio)carbonyloxy group or sulphonyloxy group, whereby this residue is directly attached to the benzene nucleus A via the oxygen atom,
$R^3$ is halogen or cyano,
$R^4$ is hydrogen or halogen,
$R^5$ is hydrogen, halogen or $C_{1-4}$-alkyl,
$R^6$ is $C_{1-4}$-alkyl or $C_{1-4}$-haloalkyl, or
$R^5$ and $R^6$ together are tri- or tetramethylene,
as well as salts of those compounds of formula I in which $R^1$ is hydrogen.

The following residues are examples of $R^2$ as an ether group:
$C_{1-8}$-alkoxy
$C_{3-7}$-cycloalkoxy
$C_{3-8}$-alkenoxy
$C_{3-6}$-alkynoxy
$C_{4-8}$-cycloalkylalkoxy
optionally substituted phenyl-$C_{1-4}$-alkoxy
$C_{1-8}$-haloalkoxy
$C_{3-9}$-haloalkenoxy
$C_{3-8}$-haloalkynoxy
$C_{2-8}$-cyanoalkoxy, especially of the formula

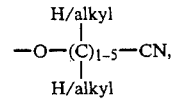

in which the sum of the carbon atoms is 2 to 8;
$C_{1-8}$-nitroalkoxy, especially of the formula

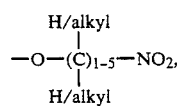

in which the sum of the carbon atoms is 1 to 8,
$C_{2-8}$-alkoxyalkoxy
$C_{6-8}$-cycloalkoxyalkoxy
$C_{4-8}$-alkenoxyalkoxy
$C_{5-8}$-alkoxyalkenoxy
$C_{4-8}$-alkynoxyalkoxy
$C_{5-8}$-alkoxyalkynoxy
optionally substituted phenoxy-$C_{1-4}$-alkoxy
optionally substituted phenoxy-$C_{3-4}$-alkynoxy
optionally substituted benzyloxy-$C_{1-4}$-alkoxy C$_{4-8}$-alkoxyalkoxyalkoxy
C$_{4-9}$-dialkoxyalkoxy, especially of the formula

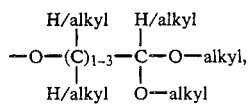

in which the sum of the carbon atoms is 4 to 9;
C$_{3-8}$-haloalkoxyalkoxy
C$_{4-8}$-haloalkenoxyalkoxy
C$_{2-8}$-alkylthioalkoxy
C$_{6-8}$-cycloalkylthioalkoxy
C$_{4-8}$-alkenylthioalkoxy
C$_{5-8}$-alkylthioalkenoxy
C$_{4-8}$-alkynylthioalkoxy
C$_{5-8}$-alkylthioalkynoxy
optionally substituted phenylthio-C$_{1-4}$-alkoxy
C$_{2-8}$-alkylsulphinylalkoxy
optionally substituted phenylsulphinyl-C$_{1-4}$-alkoxy
C$_{2-8}$-alkylsulphonylalkoxy
optionally substituted phenylsulphonyl-C$_{1-4}$-alkoxy
C$_{3-8}$-alkoxycarbonylalkoxy
formyl-, alkanoyl- or optionally substituted benzoylalkoxy, especially of the formula

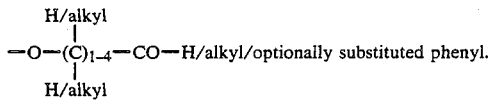

in which the sum of the carbon atoms with the exception of those of an optionally substituted phenyl group which may be present is 2 to 8;
optionally N-monosubstituted or N,N-disubstituted carbamoylalkoxy, especially of the formula

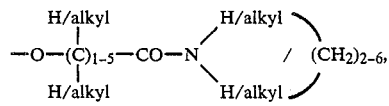

in which the sum of the carbon atoms is 2 to 10;
optionally N-monosubstituted or N,N-disubstituted β-aminoethoxy, especially of the formula

in which the sum of the carbon atoms is 2 to 8;
C$_{4-8}$-trialkylsilylalkoxy, especially of the formula

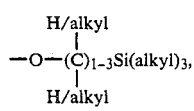

in which the alkyl groups are similar or different and the sum of the carbon atoms is 4 to 8;
a group of the formula

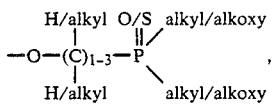

in which the sum of the carbon atoms is 3 to 8;
C$_{3-9}$-alkylideneaminooxyalkoxy, especially of the formula

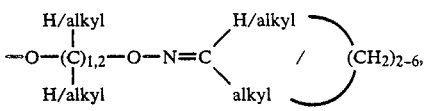

in which the sum of the carbon atoms is 3 to 9;
a group of the formula

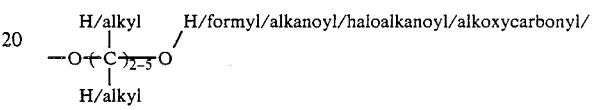

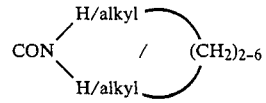

in which the sum of the carbon atoms is 3 to 10;
heterocyclyloxy or heterocyclylalkoxy, especially of the formula —O—(CH$_2$)$_{0-3}$-heterocyclyl, in which the heterocyclyl group is 3- to 7-membered, unsaturated, partially saturated or fully saturated and unsubstituted or substituted and contains up to 4 hetero atoms selected from nitrogen, oxygen and sulphur;
The following residues are examples of R$^2$ as a residue containing a (thio)carbonyloxy group:
Formyloxy
C$_{2-8}$-alkanoyloxy
C$_{2-5}$-thioalkanoyloxy
C$_{4-8}$-cycloalkanoyloxy
C$_{3-8}$-alkenoyloxy
C$_{3-8}$-alkynoyloxy
C$_{5-8}$-cycloalkylalkanoyloxy
optionally substituted benzoyloxy
optionally substituted phenyl-C$_{2-4}$-alkanoyloxy C$_{2-8}$-haloalkanoyloxy
C$_{3-6}$-cyanoalkanoyloxy
C$_{3-8}$-alkoxyalkanoyloxy
C$_{4-9}$-alkylcarbonylalkanoyloxy, especially of the formula

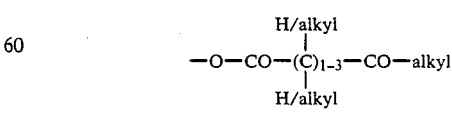

in which the sum of the carbon atoms is 4 to 9;
C$_{2-8}$-alkoxycarbonyloxy
C$_{6-8}$-cycloalkoxycarbonyloxy
C$_{3-8}$-alkenoxycarbonyloxy
C$_{4-8}$-alkynoxycarbonyloxy C$_{5-8}$-cycloalkylalkoxycarbonyloxy
optionally substituted phenoxycarbonyloxy
optionally substituted phenyl-C$_{1-4}$-alkoxycarbonyloxy
C$_{3-8}$-haloalkoxycarbonyloxy
C$_{4-8}$-alkoxyalkoxycarbonyloxy
C$_{2-8}$-(alkylthio)carbonyloxy
C$_{2-8}$-alkoxythiocarbonyloxy
C$_{2-8}$-(alkylthio)thiocarbonyloxy
N-monosubstituted or N,N-disubstituted carbamoyloxy, especially of the formula —O—CO—NR$^{21}$R$^{22}$ in which R$^{21}$ is hydrogen and R$^{22}$ is alkyl, cycloalkyl, cycloalkylalkyl, alkenyl, alkynyl, optionally substituted phenyl or optionally substituted phenyl-C$_{1-4}$-alkyl, or R$^{21}$ and R$^{22}$ each independently is alkyl or alkenyl, or R$^{21}$ and R$^{22}$ together are —(CH$_2$)$_{2-6}$- and in which, where no optionally substituted phenyl group is present, the sum of the carbon atoms is 2 to 10;
N-monosubstituted or N,N-disubstituted thiocarbamoyloxy, especially of the formula

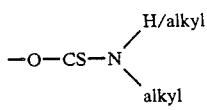

in which the sum of the carbon atoms is 2 to 9;
a group of the formula

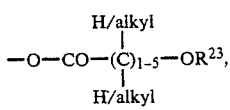

in which R$^{23}$ is hydrogen, formyl, alkanoyl, haloalkanoyl, alkoxycarbonyl or

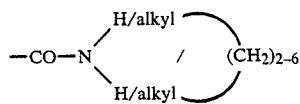

and the sum of the carbon atoms is 2 to 10;
a group of the formula

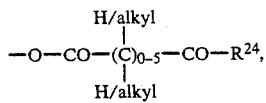

in which R$^{24}$ is hydroxy, alkoxy, haloalkoxy or

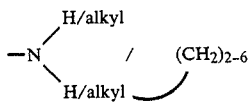

and the sum of the carbon atoms is 2 to 10;
heterocyclylcarbonyloxy or heterocyclylalkanoyloxy, especially of the formula —O—CO—(CH$_2$)$_{0-3}$-heterocyclyl in which the heterocyclyl group is 3- to 7-membered, unsaturated, partially saturated or fully saturated and unsubstituted or substituted and contains up to 4 hetero atoms selected from nitrogen, oxygen and sulphur;.

The following residues are examples of R$^2$ as a residue containing a sulphonyloxy group;

C$_{1-8}$-alkylsulphonyloxy
optionally substituted phenyl-C$_{1-4}$-alkylsulphonyloxy
optionally substituted phenylsulphonyloxy
C$_{1-5}$-alkoxysulphonyloxy
N-monosubstituted or N,N-disubstituted sulphamoyloxy, especially of the formula —O—SO$_2$—NR$^{25}$R$^{26}$ in which R$^{25}$ and R$^{26}$ is hydrogen and alkyl, independently of each other alkyl, hydrogen and cycloalkyl or together —(CH$_2$)$_{3-6}$- and the sum of the carbon atoms is 1 to 8.

In the above residues a halogen atom which may be present is fluorine, chlorine, bromine or iodine. A haloalkoxy, haloalkenoxy, haloalkynoxy or haloalkanoylo,xy group, per se or as part of a larger residue, can have one or more (similar or different) halogen atoms. The alkyl, alkenyl and alkynyl groups—as parts of larger residues—can be straight-chain or branched. In the case of optionally substituted phenyl, phenoxy, phenylthio, benzyloxy or benzoyl—as part of a larger residue—there come into consideration the respective aromatic groups which can carry on the benzene nucleus substituents which are usual in plant protection such as, for example, halogen atoms, especially fluorine, chlorine and bromine, nitro, cyano and lower alkyl, haloalkyl and alkoxy groups, As examples of heterocyclyl groups—as parts of larger residues—there may be named: oxiranyl, 2-furyl, 2-tetrahydrofuryl, 1,3-dioxolan-2-yl, 1,3-oxathiolan-2-yl, 1,3-dithiolan-2-yl, tetrahydro-2H-pyran-2-yl, 2-oxo-tetrahydro-3-furyl, 2-thienyl, 2-pyridyl, 3-pyridyl, 2-pyrimidinyl and 1-methyl-3-tr[fluoromethyl-1H-1,2,4-triazol-5-yl.

In the case of the salts of the compounds of formula I there come into onsideration especially alkali metal salts, e.g. sodium and potassium salts; alkaline earth metal salts, e.g. calcium and magnesium salts; and ammonium salts, i.e. unsubstituted ammonium salts and mono- or multiply-substituted ammonium salts, e.g. triethylammonium, methylammonium and (2-hydroxyethyl)ammonium salts.

The possible presence of at least one asymmetric carbon atom in the compounds of formula I means that the compounds can occur in optically isomeric forms. Geometric isomerism can also occur when an aliphatic C=C double bond is present. Moreover, in the case of those compounds of formula I in which R$^1$ is hydrogen keto-enol tautomerism [—NH—CO—⇌—N=C(OH)—] can occur. Formula I is intended to embrace all of these possible isomeric forms as well as mixtures thereof.

preferred compounds of formula I are those wherein R$^1$ is C$_{1-4}$-alkyl, C$_{1-4}$-haloalkyl, formyl or C$_{2-6}$-alkanoyl. Especially preferred are compounds wherein R$^1$ is methyl. Independently of R$^1$ and from one another R$^2$ preferably is C$_{1-8}$-alkoxy, especially C$_{1-3}$-alkoxy; C$_{3-7}$-cycloalkoxy; C$_{3-8}$-alkenoxy, especially allyloxy; C$_{3-6}$-alkynoxy, especially propargyloxy; C$_{4-8}$-cycloalkylalkoxy; optionally substituted phenyl-C$_{1-4}$-alkoxy, especially optionally substituted benzyloxy; C$_{1-8}$-haloalkoxy; C$_{3-9}$-haloalkenoxy; C$_{2-8}$-alkoxyalkoxy; optionally substituted phenoxy-C$_{1-4}$-alkoxy; C$_{4-8}$-haloalkenoxyalkoxy; C$_{2-8}$-alkylthioalkoxy; N-alkyl- or N,N-dialkylcarbamoylalkoxy in which the sum of the carbon atoms is 2 to 10; C$_{3-8}$-alkynoyloxy; N-alkyl- or N,N-dialkylcarbamoyloxy in which the sum of the carbon atoms is 2 to 10: C$_{1-8}$-alkylsulphonyloxy; optionally substituted phenylsulphonyloxy; or N-alkyl or N,N-dialkylsulphamoyloxy in which the sum of the carbon atoms is 1 to 8; R$^3$ preferably is halogen, especially chlorine or bromine; $R^4$ preferably is halogen, especially fluorine; $R^5$ preferably is hydrogen, fluorine or methyl; and $R^6$ preferably is methyl or trifluoromethyl, Moreover, there are preferred certain combinations of $R^1$-$R^6$, namely;

$R^1$ different from hydrogen, $R^5$ hydrogen;
$R^1$ different from hydrogen, $R^4$ fluorine, $R^5$ hydrogen;
$R^1$ different from hydrogen, $R^5$ hydrogen, $R^6$ trifluoromethyl;
$R^1$ methyl, $R^4$ fluorine, $R^5$ hydrogen, $R^6$ trifluoromethyl;
$R^1$ methyl, $R^3$ chlorine, $R^4$ fluorine, $R^5$ hydrogen, $R^6$ trifluoromethyl.

As can be seen from formula I above, the phrase "$R^1$ different from hydrogen" means $R^1$ is $C_{1-4}$-alkyl, $C_{1-4}$-haloalkyl, formyl or $C_{2-6}$-alkanoyl, Indeed, throughout the specification, where $R^1$ is stated to be different from hydrogen, it is meant that $R^1$ is $C_{1-4}$-alkyl, $C_{1-4}$-haloalkyl, formyl or $C_{2-6}$-alkanoyl, unless the specification, specifically indicates otherwise.

Especially preferred individual compounds of formula I are:

3-(4-Chloro-2-fluoro-5-propargyloxyphenyl)-1-methyl-6-trifluoromethyl-2,4(1H,3H)-pyrimidinedione,
3-(4-chloro-2-fluoro-5-isopropoxyphenyl)-1-methyl-6-trifluoromethyl-2,4(1H,3H)-pyrimidinedione,
3-(5-ethoxy-4-chloro-2-fluorophenyl)-1-methyl-6-trifluoromethyl-2,4(1H,3H)-pyrimidinedione,
3-(4-chloro-2-fluoro-5-methoxyphenyl)-1-methyl-6-trifluoromethyl-2,4(1H,3H)-pyrimidinedione,
3-(5-butoxy-4-chloro-2-fluorophenyl)-1-methyl-6-trifluoromethyl-2,4(1H,3H)-pyrimidinedione,
3-(4-chloro-2-fluoro-5-propoxyphenyl)-1-methyl-6-trifluoromethyl-2,4(1H,3H)-pyrimidinedione,
3-(5-allyloxy-4-chloro-2-fluorophenyl)-1-methyl-6-trifluoromethyl-2,4(1H,3H)-pyrimidinedione,
3-(4-chloro-2-fluoro-5-isopropoxyphenyl)-1-methyl-6-pentafluoroethyl-2,4(1H,3H)-pyrimidinedione,
3-(4-chloro-2-fluoro-5-isopropoxyphenyl)-5-fluoro-1-methyl-6-pentafluoroethyl-2,4(1H,3H)-pyrimidinedione,
3-(4-chloro-2-fluoro-5-methoxymethoxy-phenyl)-1-methyl-6-trifluoromethyl-2,4(1H,3H)-pyrimidinedione,
2-chloro-5-[3,6-dihydro-2,6-dioxo-3-methyl-4-trifluoromethyl-1(2H)-pyrimidinyl]-4-fluorophenyl N-tert.butylcarbamate,
3-[5-(2-bromoethoxy)-4-chloro-2-fluorophenyl]-1-methyl-6-trifluoromethyl-2,4(1H,3H)-pyrimidinedione,
2-chloro-5-[3,6-dihydro-2,6-dioxo-3-methyl-4-trifluoromethyl-1(2H)-pyrimidinyl]-4-fluorophenyl p-chlorobenzenesulphonate,
3-[4-chloro-5-(3,3-dichloroallyloxy)-2-fluorophenyl]-1-methyl-6-trifluoromethyl-2,4(1H,3H)-pyrimidinedione,
3-{4-chloro-5-[2-(2,2-dichlorovinyloxy)-ethoxy]-2-fluorophenyl}-1-methyl-6-trifluoromethyl-2,4(1H,3H)-pyrimidinedione,
3-{4-chloro-5-[2-(2-methoxyethoxy)-ethoxy]-phenyl}-1-methyl-6-trifluoromethyl-2,4(1H,3H)-pyrimidinedione,
2-chloro-5-[3,6-dihydro-2,6-dioxo-3-methyl-4-trifluoromethyl-1(2H)-pyrimidinyl]-4-fluorophenyl dimethylsulphamate,
2-chloro-5-[3,6-dihydro-2,6-dioxo-3-methyl-4-trifluoromethyl-1(2H)-pyrimidinyl]-4-fluorophenyl methanesulphonate,
3-(4-chloro-2-fluoro-5-methylthiomethoxy-phenyl)-1-methyl-6-trifluoromethyl-2,4(1H,3H)-pyrimidinedione,
3-(4-chloro-5-difluoromethoxy-2-fluorophenyl)-1-methyl-6-trifluoromethyl-2,4(1H,3H)-pyrimidinedione,
2-chloro-5-[3,6-dihydro-2,6-dioxo-3-methyl-4-trifluoromethyl-1(2H)-pyrimidinyl]-4-fluorophenyl 2-propiolate,
3-[4-chloro-2-fluoro-5-(2-methoxyethoxy)-phenyl]-1-methyl-6-trifluoromethyl-2,4(1H,3H)-pyrimidinedione,
3-[5-(2-ethoxyethoxy)-4-chloro-2-fluorophenyl]-1-methyl-6-trifluoromethyl-2,4(1H,3H)-pyrimidinedione,
3-{4-chloro-5-[(p-chlorophenoxy)methoxy]-2-fluorophenyl}-1-methyl-6-trifluoromethyl-2,4(1H,3H)-pyrimidinedione,
3-(5-benzyloxy-4-chloro-2-fluorophenyl)-1-methyl-6-trifluoromethyl-2,4(1H,3H)-pyrimidinedione,
2-{2-chloro-5-[3,6-dihydro-2,6-dioxo-3-methyl-4-trifluoromethyl-1(2H)-pyrimidinyl]-4-fluorophenoxy}-N,N-dimethyl-acetamide,
3-(4-chloro-2-fluoro-5-isopropoxyphenyl)-1-difluoromethyl-6-methyl-2,4(1H,3H)-pyrimidinedione,
3-(4-chloro-5-cyclohexylmethoxy-2-fluorophenyl)-1-methyl-6-trifluoromethyl-2,4(1H,3H)-pyrimidinedione,
3-(4-chloro-5-cyclopentoxy-2-fluorophenyl)-1-methyl-6-trifluoromethyl-2,4(1H,3H)-pyrimidinedione and
2-chloro-5-[3,6-dihydro-2,6-dioxo-3-methyl-4-trifluoromethyl-1(2H)-pyrimidinyl]-4-fluorophenyl isopropanesulphonate.

Also representative of compounds of formula I are 3-(4-chloro-2-fluoro-5-$R^{2'}$-phenyl)-1-methyl-6-trifluoromethyl-2,4(1H,3H)-pyrimidinediones wherein $R^{2'}$ is:

3-Chloro-2-propynoxy, 2-cyano-n-propoxy, nitromethoxy, 4-methoxy-2-butynoxy, (2-chloroethoxy)methoxy, 4-methylthio-2-butenoxy, propargylthiomethoxy, 4-methylthio-2-butynoxy, methoxycarbonylmethoxy, isopropoxycarbonylmethoxy, 2-acetamidoethoxy, 2-methoxycarbonyloxy-ethoxy, (2-tetrahydrofuryl)methoxy, (1,3-oxathiolan-2-yl)methoxy, (1,3-dithiolan-2-yl)methoxy, tetrahydro-2H-pyran-2-yloxy, 2-thienyloxy, 2-pyridyloxy, thioacetoxy, trichloroacetoxy, (3-chloropropionyl)oxy, acetoacetoxy, (2-methoxyethoxy)carbonyloxy, N-phenylcarbamoyloxy, N-methylthiocarbamoyloxy, 4-hydroxybutyryloxy, 4-formyloxybutyryloxy, 4-acetoxybutyryloxy, 4-(methoxycarbonyloxy)butyryloxy, 4-(N-methylcarbamoyloxy)butyryloxy, 3-carboxy-propionyloxy, methoxycarbonylacetoxy, 3-carbamoyl-propionyloxy, 3-(N,N-dimethylcarbamoyl)-propionyloxy, isopropoxysulphonyloxy and N-cyclohexylsulphamoyloxy, Other representative of compounds of formula I are 3-(4-chloro-2-fluoro-5-propargyloxyphenyl)-1,6-dimethyl-2,4(1H,3H)-pyrimidinedione,
3-(4-chloro-2-fluoro-5-propargyloxyphenyl)-1-methyl-5,6,7,8-tetrahydro-2,4(1H,3H)-quinazolinedione,
3-(5-ethoxy-4-chloro-2-fluorophenyl)-5-fluoro-1-methyl-6-trifluoromethyl-2,4(1H,3H)-pyrimidinedione,
3-(5-ethoxy-4-chloro-2-fluorophenyl)-5-chloro-1-methyl-6-trifluoromethyl-2,4(1H,3H)-pyrimidinedione,
5-chloro-3-(4-chloro-2-fluoro-5-isopropoxyphenyl)-1-methyl-6-trifluoromethyl-2,4(1H,3H)-pyrimidinedione, 3-(4-chloro-2-fluoro-5-propargyloxyphenyl)-5-fluoro-1-methyl-6-trifluoromethyl-2,4(1H,3H)-pyrimidinedione, 5-chloro-3-(4-chloro-2-fluoro-5-propargyloxyphenyl)-1-methyl-6-trifluoromethyl-2,4(1H,3H)-pyrimidinedione, 3-(5-ethoxy-4-chloro-2-fluorophenyl)-5-fluoro-1-methyl-6-pentafluoroethyl-2,4(1H,3H)-pyrimidinedione, 3-(5-ethoxy-4-chloro-2-fluorophenyl)-5-chloro-1-methyl-6-pentafluoroethyl-2,4(1H,3H)-pyrimidinedione, 5-chloro-3-(4-chloro-2-fluoro-5-isopropoxyphenyl)-1-methyl-6-pentafluoroethyl-2,4(1H,3H)-pyrimidinedione, 3-(4-chloro-2-fluoro-5-propargyloxyphenyl)-5-fluoro-1-methyl-6-pentafluoroethyl-2,4(1H,3H)-pyrimidinedione, 5-chloro-3-(4-chloro-2-fluoro-5-propargyloxyphenyl)-1-methyl-6-pentafluoroethyl-2,4(1H,3H)-pyrimidinedione, 3-(4-chloro-2-fluoro-5-isopropoxyphenyl)-1-formyl-6-trifluoromethyl-2,4(1H,3H)-pyrimidinedione, 1-acetyl-3-(4-chloro-2-fluoro-5-isopropoxyphenyl)-6-trifluoromethyl-2,4(1H,3H)-pyrimidinedione, 3-(4-chloro-2-fluoro-5-isopropoxyphenyl)-1-methoxycarbonyl-6-trifluoromethyl-2,4(1H,3H)-pyrimidinedione, 3-(4-Chloro-5-propargyloxyphenyl)-1-methyl-6-trifluoromethyl-2,4(1H,3H)-pyrimidinedione, 3-(5-ethoxy-4-chlorophenyl)-1-methyl-6-trifluoromethyl-2,4(1H,3H)-pyrimidinedione, 3-(4-chloro-5-isopropoxyphenyl)-1-methyl-6-trifluoromethyl-2,4(1H,3H)-pyrimidinedione, 3-(5-benzyloxy-4-chlorophenyl)-1-methyl-6-trifluoromethyl-2,4(1H,3H)-pyrimidinedione, 3-[4-chloro-2-fluoro-5-(2-fluoro-1-fluoromethylethoxy)phenyl]-1-methyl-6-trifluoromethyl-2,4(1H,3H)-pyrimidinedione, 3-(4-chloro-2-fluoro-5-pentafluoroethoxyphenyl)-1-methyl-6-trifluoromethyl-2,4(1H,3H)-pyrimidinedione and 3-(4-chloro-2-fluoro-5-trifluoromethoxyphenyl)-1-methyl-6-trifluoromethyl-2,4(1H,3H)-pyrimidinedione.

The process in accordance with the invention for the manufacture of the compounds of formula I and their salts comprises (a) subjecting a compound of the formula

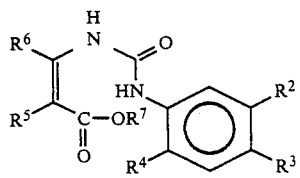

wherein
$R^2$, $R^3$, $R^4$, $R^5$ and $R^6$ are as described above and
$R^7$ is lower alkyl, preferably $C_{1-4}$-alkyl,
to a cyclization under basic conditions and, if desired, either converting the thus-obtained salt of the formula

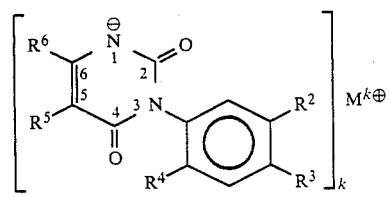

wherein
$R^2$, $R^3$, $R^4$, $R^5$ and $R^6$ are as described above, and
$M^{k\oplus}$ is a cation and
k is the valency of the cation,
into the corresponding acid form ($R^1$=hydrogen) or N-substituting the thus-obtained salt with the desired residue $R^1$, and, if desired, halogenating a thus-obtained 5-unsubstituted compound of formula I ($R^5$=hydrogen), or (b) replacing the hydroxy group in a compound of the formula

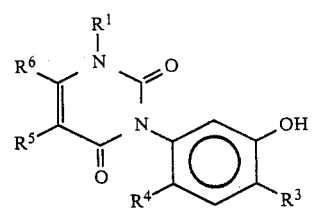

wherein $R^1$, $R^3$, $R^4$, $R^5$ and $R^6$ are as described above, by the substituents $R^2$ in a manner known per se and, if desired, halogenating a thus-obained 5-unsubstituted compound of formula I ($R^5$=hydrogen).

The cyclization according to process variant a) can be carried out conveniently by treating the compound of formula II in an inert protic organic solvent such as an alcohol, e.g. methanol, ethanol or isopropanol; an inert aprotic organic solvent such as an aliphatic or cyclic ether, e.g. 1,2-dimethoxyethane, tetrahydrofuran or dioxan, or an aromatic, e.g. benzene or toluene; an inert aprotic, polar organic solvent, e.g. dimethylformamide or dimethyl sulphoxide, whereby such solvents can be optionally used in a two-phase mixture with a hydrocarbon, e.g. n-hexane; or water with a base at temperatures between room temperature and the reflux temperature of the reaction mixture. As bases there preferably come into consideration sodium alcoholates, alkali metal hydroxides, especially sodium hydroxide and potassium hydroxide, alkali metal carbonates, especially sodium carbonate and potassium carbonate, and sodium hydride. When the last-named base is used, the solvent is preferably an aliphatic or cyclic ether, dimethylformamide or dimethyl sulphoxide.

This process is especially suitable for the manufacture of the compounds in accordance with the invention in which $R^2$ of formula I is a base-stable residue. Among the residues $R^2$ referred to above the following in particular are regarded as being base-stable: alkoxy, cycloalkoxy, alkenoxy, alkynoxy, cycloalkylalkoxy, optionally substituted phenylalkoxy, cyanoalkoxy, alkoxyalkoxy, cycloalkoxyalkoxy, alkenoxy- alkoxy, alkoxyalkenoxy, alkynoxyalkoxy, alkoxyalkynoxy, optionally substituted phenoxyalkoxy, optionally substituted phenoxyalkynoxy, optionally substituted benzyloxyalkoxy, alkoxyalkoxyalkoxy, dialkoxyalkoxy, alkylthioalkoxy, cycloalkylthioalkoxy, alkenylthioalkoxy, alkylthioalkenoxy, alkynylthioalkoxy, alkylthioalkynoxy, optionally substituted phenylthioalkoxy, N,N-dialkyl-β-aminoethoxy and trialkylsilylalkoxy.

For the illustration of this process there serves as a typical example the cyclization of a compound of formula II wherein $R^2$ is $C_{1-8}$-alkoxy. For this there are used as solvents polar, aprotic solvents such as dimethylformamide and alcohols, e.g. ethanol, especially dimethylformamide, and as bases sodium hydride and alkali metal alcoholates, especially sodium ethylate and the reaction is conveniently carried out at temperatures between $-30°$ C. and $30°$ C., preferably at room temperature.

After completion of the cyclization the product is present in the form of the corresponding metal salt of formula I' depending on the nature of the base which is used, for example in the form of the corresponding alkali metal salt in the case of the above-mentioned bases. This salt can be isolated and purified in a manner known per se.

Where a compound of formula I wherein $R^1$ is hydrogen is subsequently desired, the mixture which results after the cyclization can be acidified in order to convert the salt I' into the corresponding acid form of the compound I ($R^1$ = hydrogen). For this purpose there is preferably used a mineral acid such as hydrochloric acid or a strong organic acid such as acetic acid or p-toluenesulphonic acid, Also in this case the product can be isolated and purified in a manner known per se.

Alternatively, the salt of formula I' can be converted by alkylation or acylation into the corresponding N-substituted compound of formula I. The term "alkylation" or "acylation" stands here for the introduction of a $C_{1-4}$-alkyl or $C_{1-4}$-haloalkyl group or a formyl or $C_{2-6}$-alkanoyl group, respectively, on the unsubstituted nitrogen atom of the uracil nucleus. As the alkylating agent there is conveniently used a $C_{1-4}$-alkyl, or $C_{1-4}$-haloalkyl, halide, especially the respective chloride or bromide, or sulphate. As the acylating agent there comes into consideration especially a mixture of acetic anhydride and formic acid or a $C_{2-6}$-alkanecarboxylic acid halide, with the respective chloride or bromide being the preferred halide.

The alkylation is conveniently carried out in the presence of an inert, protic organic solvent such as a lower alkanol, e.g. ethanol, optionally in admixture with water; an inert, aprotic organic solvent such as an aliphatic or cyclic ether, e.g, 1,2-dimethoxyethane, tetrahydrofuran or dioxan, or an aliphatic ketone, e.g. acetone; or an inert, aprotic, polar organic solvent, e.g. dimethylformamide or dimethyl sulphoxide, at temperatures between $0°$ C. and about $50°$ C., preferably at room temperature. In a preferred embodiment the salt of formula I' is treated in the same solvent in which it has been prepared by cyclization of the compound of formula II, so that excess base, as in the case of the reaction of the sodium salt of formula I' ($M^{k\oplus} = Na^{\oplus}$) sodium hydride, a sodium alcoholate or sodium carbonate, is still present in the reaction mixture. The acylation with a halide can be effected in a similar manner, although in this case it is carried out, in particular, in an aprotic solvent and in the presence of sodium hydride.

In the case of the manufacture of those compounds of formula I wherein $R^1$ is $C_{2-6}$-alkanoyl the acid form of the compound of formula I ($R^1$ = hydrogen) can be acylated in place of the salt, namely with the corresponding alkanecarboxylic acid anhydride, suitably without a base, in a manner known per se.

For the manufacture of those compounds of formula I wherein $R^5$ is chlorine, bromine or iodine, a uracil derivative of formula I wherein $R^5$ is hydrogen, namely the 5-unsubstituted compound of formula I obtained in the above manner, can be chlorinated, brominated or iodinated, respectively.

The chlorination or bromination is conveniently carried out by means of elementary chlorine or sulphuryl chloride or elementary bromine or sulphuryl bromide, respectively, in the presence of an inert organic solvent such as an aliphatic carboxylic acid, e,g acetic acid, or a chlorinated aliphatic hydrocarbon, e.g. methylene chloride, chloroform or carbon tetrachloride, and in a temperature range of $0°$ C. to $60°$ C., preferably at room temperature. Moreover, the reaction can be effected with the aid of an acid-binding agent, for which purpose sodium acetate and tertiary amines such as triethylamine, dimethylamine and pyridine are especially preferred acid-binding agents.

The iodination is conveniently effected using elementary iodine as the iodinating agent and a low-boiling aliphatic carboxylic acid such as acetic acid as the solvent and at temperatures between about $0°$ C. and about $110°$ C., preferably at room temperature. Moreover, it has been found to be convenient to carry out the reaction in the presence of an acid such as fuming nitric acid. In order to remove excess iodine, saturated aqueous sodium bisulphite solution can be added after the completion of the reaction.

Depending on the nature of the residue $R^2$, process variant (b) is an ether formation, an acylation or a sulphonylation, which can be carried out in a manner known per se. Further reaction steps and/or different substitution or addition reactions at the hydroxy group are, of course, not to be excluded from this process variant upon substituting the hydroxy group by the substituents $R^2$.

As a typical example of an ether formation, a compound of formula III is converted into a compound of formula I wherein $R^2$ is $C_{3-6}$-alkynoxy, e.g. propargyloxy. This is conveniently carried out by treating the compound III in an inert aprotic, polar solvent such as, for example, dimethylformamide, dimethyl sulphoxide or acetonitrile, with a base, e.g. sodium hydride or potassium carbonate and reacting the resulting salt with a $C_{3-6}$-alkynyl halide, especially the chloride or bromide, at temperatures between room temperature and about $80°$ C., conveniently in the same solvent. The reaction is preferably carried out in dimethylformamide in the presence of sodium hydride at room temperature.

The manufacture of those compounds I wherein $R^2$ is $C_{2-8}$-alkoxycarbonyloxy, e.g. methoxycarbonyloxy, serves as a typical example for the conversion of a compound of formula III into a compound of formula I wherein $R^2$ is a residue containing a (thio)carbonyloxy group. The reaction is conveniently carried out by treating the compound III in an inert aprotic solvent such as dimethylformamide, dimethyl sulphoxide, acetonitrile, an aliphatic ether, e.g. 1,2-dimethoxyethane, or a chlorinated, aliphatic hydrocarbon, e.g. methylene chloride, with a base such as, for example, sodium hydride, triethylamine or pyridine and subsequently treating with a $C_{2-8}$-alkoxycarbonyl halide in the same solvent at temperatures between room temperature and about $80°$ C. The reaction is preferably carried out in methylene chloride in the presence of triethylamine or pyridine at room temperature, and methyl chloroformate is subsequently added, also at room temperature.

The manufacture of those compounds I wherein $R^2$ is N-monosubstituted or N,N-disubstituted sulphamoyloxy, e.g. N,N-dimethylsuphamoyloxy, serves for the illustration of the conversion of a compound of formula III into a compound of formula I wherein $R^2$ is a residue containing sulphonyloxy group. The reaction is conveniently effected under approximately the same reaction conditions as described above for the reaction with a $C_{2-8}$-alkoxycarbonyl halide.

This process is especially suitable for the manufacture of the compounds of formula I in accordance with the invention wherein $R^1$ is an acid-stable residue. These are especially alkyl and haloalkyl.

Starting from those products of process variant (b) wherein $R^5$ is hydrogen the corresponding 5-chloro-, 5-bromo- or 5-iodouracils ($R^5$=chlorine, bromine or iodine) can, if desired, be manufactured by halogenation as described in more detail above.

As mentioned above, a thus-manufactured compound of formula I can be converted in a subsequent reaction step into a further compound I which differs from its precursor by the substituent $R^2$. For example, the hydroxy group in a compound of the formula

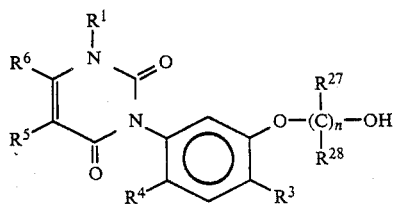

I'' wherein $R^1$, $R^3$, $R^4$, $R^5$ and $R^6$ are as described above and (each) $R^{27}$ and (each) $R^{28}$ each independently is hydrogen or lower alkyl, especially $C_{1-4}$-alkyl, and n is 2-5, is replaced by a different substituent in a manner known per se, e.g. by esterification. As a typical example of such an esterification, a compound of formula I'', e.g. one wherein $-O(CR^{27}R^{28})_n-OH$ is 2-hydroxyethyl, is acylated, e.g. with acetyl chloride. The acylation is conveniently effected in an inert aprotic diluent such as an aliphatic or cyclic ether, e.g. diethyl ether, 1,2-dimethoxyethane or tetrahydrofuran, or a chlorinated aliphatic hydrocarbon, e.g. methylene chloride, using a base, e.g. triethylamine or pyridine, at temperatures between 0° C. and 50° C., preferably at room temperature. The esterification can also be carried out, for example, by treating a compound of formula I'' with an isocyanate, whereby the corresponding carbamate is manufactured. The manufacture of the methyl carbamate serves for the illustration of this process: the compound of formula I'' is treated with methyl isocyanate under similar reaction conditions to those described above in connection with the acylation of the compound I'', whereby in the case of the reaction with the isocyanate only a catalytic amount of base is used.

A further example of the above-mentioned subsequent reaction step is the oxidation of a compound of the formula

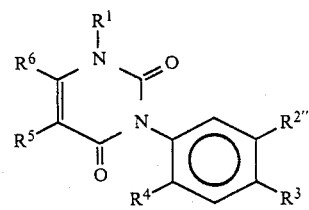

I''' wherein $R^1$, $R^3$, $R^4$, $R^5$ and $R^6$ are as described above and $R^{2''}$ is $C_{2-8}$-alkylthioalkoxy or optionally substituted phenylthio-$C_{1-4}$-alkoxy, to the corresponding sulphoxide or sulphone compound, i.e. $R^2$ in formula I is $C_{2-8}$-alkylsulphinylalkoxy or $C_{2-8}$-alkylsulphonylalkoxy or optionally substituted phenylsulphinyl- or phenylsulphonyl-$C_{1-4}$-alkoxy. In this process a customary oxidation of the sulphide I''' to the corresponding sulphoxide or sulphone depends on the nature and amount of the oxidizing agent which is used and on the other reaction conditions which are used. This is carried out, for example, in the case of a compound of formula I''' wherein $R^{2''}$ is $C_{2-8}$-alkylthioalkoxy by treating the compound I''' in a inert aprotic diluent such as an aliphatic chlorinated hydrocarbon, e.g. methylene chloride, carbon tetrachloride or 1,2-dichloroethane, with a peracid, e.g. 3-chloroperbenzoic acid, at temperatures between $-10°$ C. and $30°$ C., preferably at $0°$ C. The product is the corresponding sulphone.

For the further illustration of the above-mentioned subsequent reaction step, the amino group in a compound of the formula

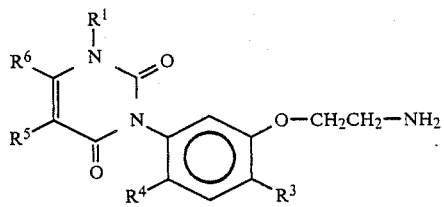

I'''' wherein $R^1$, $R^3$, $R^4$, $R^5$ and $R^6$ are as described above, is converted into a mono- or disubstituted amino group in a manner known per se. This can be, inter alia, an alkylation, an amide formation or a carbamate formation. For the alkylation the compound I'''' or a salt thereof is treated, for example, with a mixture of 36% formaldehyde and formic acid at temperatures between 50° C. and the reflux temperature of the reaction mixture, preferably at about 100° C. A formylation of the compound I'''' or a salt thereof is usually effected using formic acid as the formylating agent at the reflux temperature of the reaction mixture, while an acylation of the compound I'''' is generally undertaken in an inert aprotic diluent such as an aliphatic chlorinated hydrocarbon, e.g. methylene chloride, or an aliphatic or cyclic ether, e.g. diethyl ether, 1,2-dimethoxyethane or tetrahydrofuran, in the presence of a base, e.g. triethylamine or pyridine, at temperatures between $-10°$ C. and 50° C., preferably at room temperature. Typical acylating agents are the respective acid chlorides, e.g. acetyl chloride, and acid anhydrides, e.g. acetic anhydride.

Additional subsequent reaction steps, which lead to other compounds of formula I starting frm certain compounds of formula I, come into consideration.

Insofar as they are not manufactured directly by the above-described cyclization carried out under basic conditions according to process variant (a), the desired salts of the compounds of formula I wherein $R^1$ is hydrogen can also be manufactured from these compounds I in a manner known per se such as, for example, by dissolving the compound of formula I in a solution of the respective inorganic or organic base. The salt formation is usually effected within a short time at room temperature. In one embodiment the sodium salt is manufactured by dissolving the uracil derivative I in aqueous sodium hydroxide solution at room temperature, with equivalent amounts of the uracil derivative and of sodium hydroxide being used. The solid salt can be isolated by precipitation with a suitable inert solvent or by evaporation of the solvent. A further embodiment comprises introducing an aqueous solution of an alkali metal salt of the uracil derivative I into an aqueous solution of a salt which has a metal cation other than an alkali metal cation, whereby the second metal salt of the uracil derivative is manufactured. This embodiment serves, in general, for the manufacture of uracil metal salts which are insoluble in water.

The compounds of formula I obtained as well as their salts can be isolated and purified according to methods known per se.

Where the product results as a mixture of two or more isomers. The isomers can be separated according to methods known per se. If desired, pure optically active isomers can be manufactured, for example, by synthesis from corresponding optically active starting materials.

The starting materials of formula II, which are novel, can be produced in a manner known per se, for example in accordance with the following Reaction Scheme [methods (aa), (bb), (cc) and (dd)]:

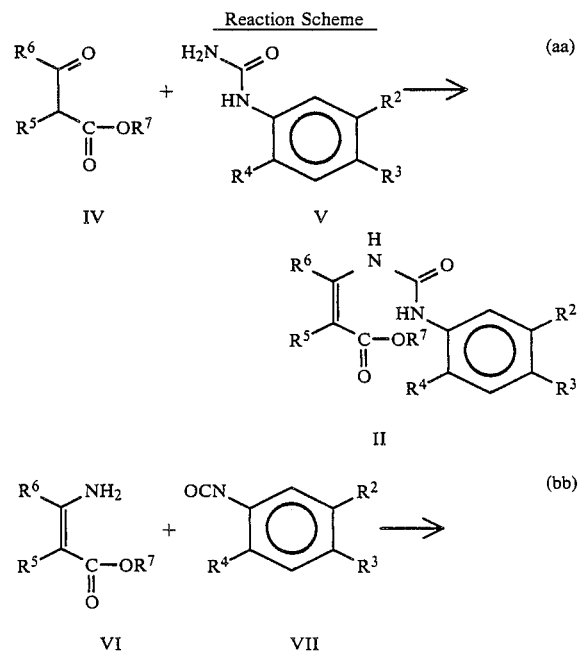

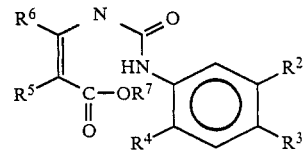

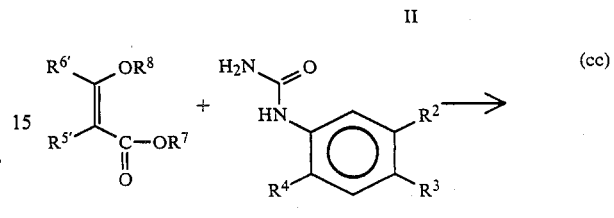

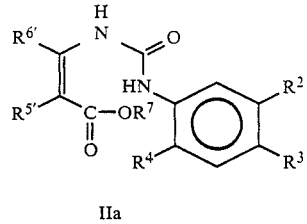

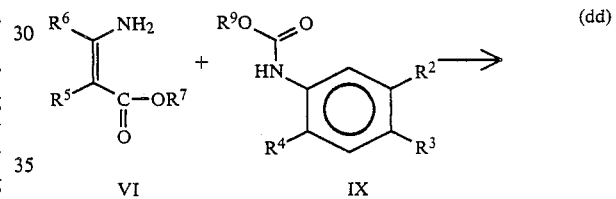

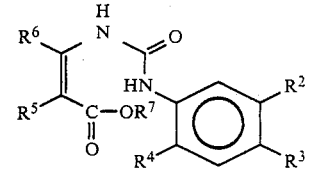

In the above Reaction Scheme $R^2$, $R^3$, $R^4$, $R^5$, $R^6$ and $R^7$ are as described above, $R^{5'}$ is hydrogen or $C_{1-4}$-alkyl; $R^{6'}$ is $C_{1-4}$-alkyl; and $R^8$ and $R^9$ each is lower alkyl, preferably $C_{1-4}$-alkyl;

Method (aa) is conveniently carried out by reacting the compounds of formulae IV and V with each other in an essentially anhydrous diluent and in the presence of an acidic catalyst at an elevated temperature. As diluents there come into consideration especially organic solvents which form azeotropes with water, such as aromatics, e.g. benzene, toluene and xylenes; halogenated hydrocarbons such as methylene chloride, chloroform, carbon tetrachloride and chlorobenzene; aliphatic and cyclic ethers such as 1,2-dimethoxyethane, tetrahydrofuran and dioxan; and cyclohexane, and as acidic catalysts there come into consideration especially strong mineral acids such as sulphuric acid and hydrochloric acid; organic acids such as p-toluenesulphonic acid, phosphorus-containing acids such as orthophosphoric acid and polyphosphoric acid; and acidic cation exchangers such as "Amberlyst 15" (Fluka). The reaction is generally carried out in a temperature range of about 70° C. to 120° C., preferably at the reflux temperature of the reaction mixture. Under these reaction conditions the desired rapid removal of the water which is formed in the reaction is achieved.

The reaction according to method (bb) is conveniently effected in the presence of an essentially anhydrous aprotic organic solvent such as an aliphatic or cyclic ether, e.g. diethyl ether, 1,2-dimethoxyethane, tetrahydrofuran or dioxan, an aliphatic or aromatic hydrocarbon, e.g. n-hexane, benzene, toluene or a xylene; or a halogenated, aliphatic hydrocarbon, e.g. methylene chloride, chloroform, carbon tetrachloride or 1,2-dichloroethane; an aprotic, polar solvent such as dimethylformamide, hexamethylphosphoric acid triamide or dimethyl sulphoxide; or a mixture of two or more of the mentioned solvents, as well as optionally in the presence of an organic tertiary base such as triethylamine or pyridine, whereby the latter can serve not only as the solvent but also as the base, or a metal hydride base such as sodium hydride or potassium hydride. The reaction temperatures are preferably in the range of about −70° C. to 50° C., with the reaction being carried out particularly at temperatures between −30° C. and room temperature, The reaction according to method (cc) is conveniently carried out in an inert, water-miscible, organic solvent such as an aliphatic or cyclic ether, e.g. 1,2-dimethoxyethane, tetrahydrofuran or dioxan, or a lower alkanol such as ethanol at temperature between 50° C. and 100° C., preferably at the reflux temperature of the reaction mixture, or in an aromatic solvent such as benzene, toluene or a xylene in the presence of an acidic catalyst such as hydrochloric acid or p-toluenesulphonic acid at temperatures between 50° C. and 100° C., preferably 60° C. to 80° C.

The reaction according to method (dd) is conveniently effected in an aprotic polar diluent such as dimethylformamide, 2-butanone, dimethyl sulphoxide or acetonitrile in the presence of a base such as an alkali metal or alkaline earth metal alcoholate or carbonate, especially a sodium alkanolate or carbonate, or a metal hydride, especially lithium or sodium hydride, at temperatures between 80° C. and 180° C., preferably at the reflux temperature of the reaction mixture. Where an alcoholate is used as the base, the alcohol which is liberated in the course of the reaction is conveniently distilled off continuously. In this method (dd) the thus-produced compound of formula II is generally produced in situ, since the reaction conditions which are used favour the cyclization of the compound II to a salt of formula I' given above, namely according to process variant (a), The starting materials of formula III which are required in process variant (b) are also novel and can be produced by the acid-catalyzed hydrolysis of the corresponding protected phenols of the formula

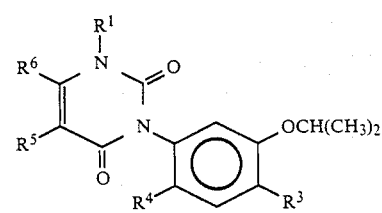

wherein $R^1$, $R^3$, $R^4$, $R^5$ and $R^6$ are as described above. This hydrolysis is conveniently effected in the presence of sulphuric acid as the acid catalyst, in a chlorinated aliphatic hydrocarbon, preferably methylene chloride, as the solvent and at temperatures between −30° C., and 30° C., preferably at room temperature. Without added solvent excess sulphuric acid itself can serve as solvent.

The hydrolysis is especially suitable for the production of those compounds of formula III wherein $R^1$ is different from hydrogen and moreover, is an acid-stable residue. Among the $R^1$ residues which are considered to be acid-stable are, in particular, $C_{1-4}$-alkyl and $C_{1-4}$-haloalkyl.

Those starting materials of formula III wherein $R^1$ is $C_{1-4}$-alkyl or $C_{1-4}$-haloalkyl can also be produced in accordance with the following Reaction Scheme:

Reaction Scheme

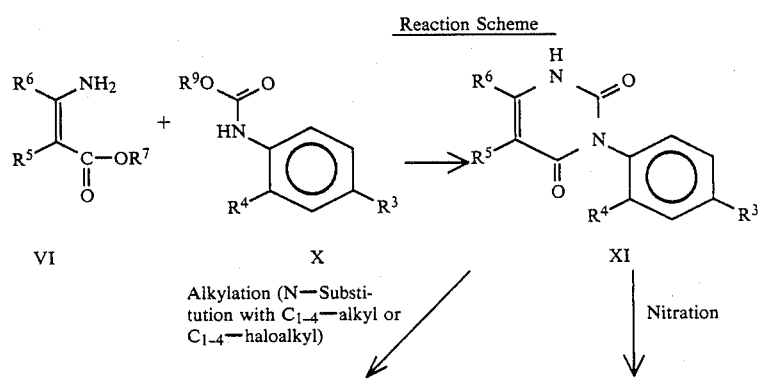

-continued
Reaction Scheme

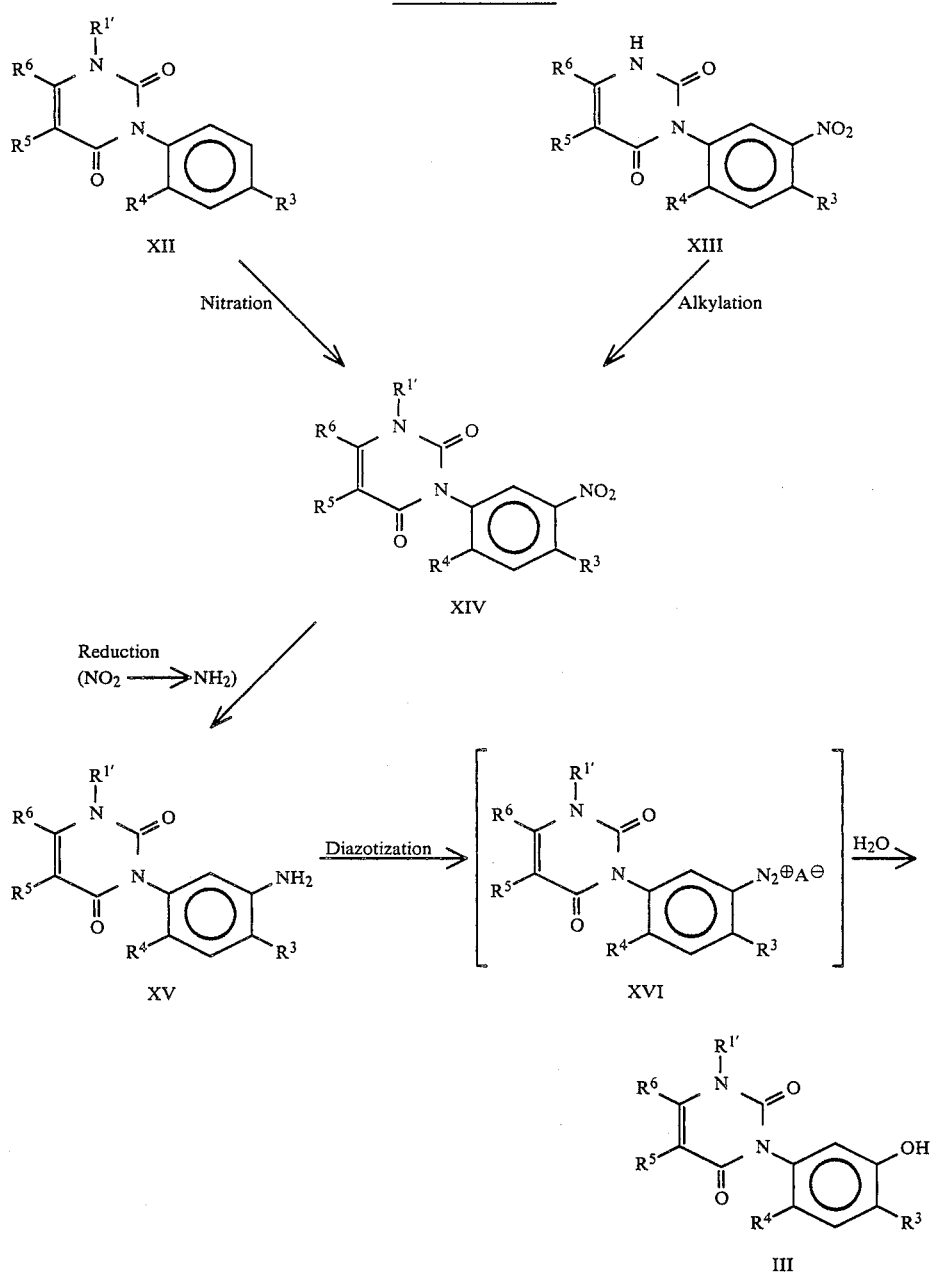

In the above Reaction Scheme $R^3$, $R^4$, $R^{5,}$ $R^6$, $R^7$ and $R^9$ are as described above; $R^{1'}$ is $C_{1-4}$-alkyl or $C_{1-4}$-haloalkyl and $A^\oplus$ is an anion, e.g. halide, hydrogen sulphate or tetrafluoroborate.

The reaction of the compounds of formulae VI and X and the alkylation are conveniently effected under the reaction conditions described above in connection with method (dd) and process variant (a), respectively, while the nitration, the reduction, the diazotization and the hydrolysis can be carried out according to methods which are known per se for these reactions taking place on a benzene ring (see, for example, Houben-Weyl, Methoden der organischen Chemie, vol, 6/1c, pages 247-265 for the diazotization and subsequent hydrolysis).

The intermediates of formulae XI, XII, XIII, XIV, XV and XVI are novel.

The above starting materials of formula I''''' are a sub-group of compounds of formula I whose preparation is described herein. The remaining starting materials or reagents which are involved in process variants (a) and (b), in the Reaction Scheme [methods (aa)–(dd)] and in the first step of the Reaction Scheme appearing subsequently (starting materials VI and X) are either known or can be produced according to methods known per se.

The compounds of formula I in accordance with the invention (including the salts) possess herbicidal properties and are suitable for the control of weeds, including weed grasses, especially *Setaria faberii, Digitaria sanguinalis, poa annua, Chenopodium album, Amaranthus re-*

*troflexus, Abutilon theopharasti, Sinapsis alba* and *Datura stramonium* in diverse crop cultivatious, especially in cotton and soya cultivations. Moreover, the compounds are not only pre-emergence, but also post-emergence herbicides, and, accordingly, can be used in a conventional manner as pre-emergence or post-emergence herbicides.

Certain compounds of formulae III and XI–XVI also possess herbicidal properties and can be used in a similar manner to the compounds I for the control of weed grasses and weeds, especially the above-mentioned. The novel compounds form a further object of the present invention. On the basis of its especially pronounced herbicidal activity 3-(4-chloro-2-fluoro-5-hydroxyphenyl)-1-methyl-6-trifluoromethyl-2,4(1H,3H)-pyrimidinedione represents a preferred compound of formula III.

A concentration of 0.0005–6.0 kg of active substance of formula I or III, XI, XII, XIII, XIV, XV or XVI/ha, preferably 0.005–2.0 kg of active substance of formula I or III, XI, XIII, XIV, XV or XVI/ha, is usually sufficient to achieve the desired herbicidal effect, with the compounds of formula I being generally significantly more active than the herbicidally active compounds of formula III or XI–XVI. The concentration range 0.01–1.5 kg of active substance of formula I or III, XI–XVI/ha is especially preferred.

The weed control composition in accordance with the invention contains an effective amount of at least one compound of formula I (including the salts) or III, XI, XII, XIII, XIV, XV or XVI, as defined above, as well as formulation adjuvants. The composition conveniently contains at least one of the following formulation adjuvants: solid carrier substances; solvents or dispersion media; tensides (wetting and emulsifying agents); dispersing agents (without tenside action); and stabilizers. With the use of these and other adjuvants these compounds, namely the herbicidally active substances, can be converted into the usual formulations such as dusts, powders, granulates, solutions, emulsions, suspensions emulsifiable concentrates, pastes and the like.

The compounds of formula I and III, XI, XII, XIII, XIV, XV or XVI [referred to hereinafter simply as the 5 active substance(s)] are generally insoluble in water and can be formulated according to methods which are usual for water-insoluble compounds using the respective formulation adjuvants. The manufacture of the compositions can be carried out in a manner known per se, e.g. by mixing the particular active substance with solid carrier substances, by dissolution or suspension in suitable solvents or dispersion media, if necessary using tensides as wetting or emulsifying agents and/or dispersing agents, by diluting pre-prepared emulsifiable concentrates with solvents or dispersion media etc.

As solid carrier substances there essentially come into consideration: natural mineral substances such as chalk, dolomite, limestone, aluminas and silicic acid and salts thereof (for example siliceous earth, kaolin, bentonite, talc, attapulgite and montmorillonite); synthetic mineral substances such as highly dispersible silicic acid, aluminium oxide and silicates; organic substances such as cellulose, starch, urea and synthetic resins; and fertilizers such as phosphates and nitrates, whereby such carrier substances can be present e.g. as powders or as granulates.

As solvents or dispersion media there essentially come into consideration: aromatics such as benzene, toluene, xylenes and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, e.g. petroleum fractions; alcohols such as butanol and glycol, as well as their ethers and esters; ketones such as acetone, methyl ethyl ketone, methyl isobutyl ketone and cyclohexanone; and strongly polar solvents or dispersion media such as dimethylformamide, N-methylpyrrolidone and dimethyl sulphoxide, such solvents preferably having flash points of at least 30° C. and boiling points of at least 50° C., and water. Among the solvents or dispersion media there also come into consideration so-called liquified gaseous extenders or carrier substances, which are those products which are gaseous at room temperature and under normal pressure. Examples of such products are especially aerosol propellants such as halogenated hydrocarbons, e.g. dichlorodifluoromethane, If the weed control composition in accordance with the invention is present in the form of a pressurized pack, then a solvent is conveniently used in addition to the propellant.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

The tensides can also be anionic compounds such as soaps; fatty sulphate esters, e.g. dodecyl sodium sulphate, octadecyl sodium sulphate and cetyl sodium sulphate; alkyl sulphonates, aryl sulphonates and fatty-aromatic sulphonates such as alkylbenzene sulphonates, e.g. calcium dodecylbenzenesulphonate, and butylnaphthalene sulphonates; and more complex fatty sulphonates, e.g. the amide condensation products of oleic acid and N-methyltaurine and the sodium sulphonate of dioctyl succinate.

Finally, the tensides can be catiohic comounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there essentially come into consideration; lignin, sodium and ammonium salts of lignin sulphonic acids, sodium salts of maleic anhydride-diisobutylene copolymers, sodium and ammonium salts of sulphonated polycondensation products of naphthalene and formaldehyde, and sulphite lyes.

As dispersing agents, which are especially suitable as thickening or anti-settling agents, there can be used e.g. methylcellulose, carboxymethylcellulose, hydroxyethylcellulose, polyvinyl alcohol, alginates, caseinates and blood albumin.

Examples of suitable stabilizers are acid-binding agents, e.g. epichlorohydrin, phenyl glycidyl ether and soya epoxides: antioxidants, e.g. gallic acid esters and butylhydroxytoluene; UV-absorbers, e.g. substituted benzophenones, diphenylacrylonitrile acid esters and cinnamic acid esters; and deactivators, e.g. salts of ethylenediaminotetraacetic acid and polyglycols.

The weed control compositions in accordance with the invention can contain, in addition to the active substances in accordance with the invention, synergists and other active substances, e.g. insecticides, acaricides, fungicides, plant growth regulators and fertilizers. Such combination compositions are suitable for intensifying the activity or for broadening the spectrum of activity.

The weed control compositions in accordance with the invention generally contain between 0.01 and 95 weight percent, preferably between 0.5 and 75 weight percent, of one or more active substances in accordance with the invention. They can be present e.g. in a form which is suitable for storage and transport. In such formulations, e.g. emulsifiable concentrates, the active substance concentration is normally in the higher range, preferably between 1 and 50 weight percent, especially between 10 and 20 weiqht percent. These formulations can be diluted, e.g. with the same or different inert substances, to give active substance concentrations which are suitable for practical use, i.e. preferably about 0.01 to 10 weight percent, especially about 0.5 to 5 weight percent. The active substance concentrations can, however, also be smaller or greater.

As mentioned above, the manufacture of the weed control compositions in accordance with the invention can be carried out in a manner known per se.

For the manufacture of pulverous preparations the active substance, i.e. at least one compound of formula I, III, XI, XII, XIII, XIV, XV or XVI, can be mixed with a solid carrier substance, e.g. by grinding together; or the solid carrier substance can be impregnated with a solution or suspension of the active substance and then the solvent or dispersion medium can be removed by evaporation, heating or sucking-off under reduced pressure. By adding tensides or dispersing agents such pulverous preparations can be made readily wettable with water, so that they can be converted into aqueous suspensions which are suitable e.g. as spray compositions.

The active substance can also be mixed with a tenside and a solid carrier substance to form a wettable powder which is dispersible in water, or it can be mixed with a solid pre-granulated carrier substance to form a product in the form of a granulate.

When desired, the active substance can be dissolved in a water-immiscible solvent such as, for example, a high-boiling hydrocarbon, which conveniently contains dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner there are obtained emulsifiable concentrates or ready-for-use emulsions.

The use of the weed control compositions in accordance with the invention, which forms a further object of the present invention, can be carried out according to usual application methods such as sprinkling, spraying, dusting, watering or scattering. The method in accordance with the invention for the control of weeds comprises treating the locus to be protected against weeds and/or the weeds with an active substance in accordance with the invention or with a weed control composition in accordance with the invention.

The following Examples illustrate the invention in more detail.

I. Manufacture of the compounds of formula I

EXAMPLE 1

A solution of 1.0 g of ethyl 3-amino-4,4,4-trifluorocrotonate in 10 ml of absolute toluene is added dropwise while stirring at 0° C. during 15 minutes to a suspension of 0.24 g of a 55% sodium hydride dispersion in 20 ml of absolute dimethylformamide and the mixture is stirred at 0° C. for 15 minutes. The reaction mixture is subsequently cooled to −30° C. and treated with a solution of 1.26 g of 4-chloro-2-fluoro-5-isopropoxyphenyl isocyanate in 10 ml of absolute toluene. The temperature rises rapidly to −10° C. and the reaction mixture is thereafter stirred at room temperature for 2 hours. The reaction mixture is poured into a solution of 3 ml of 2N hydrochloric acid and 500 ml of water and the aqueous mixture is extracted twice with 100 ml of ethyl acetate each time, and the organic phases are washed twice with 50 ml of water each time, dried over anhydrous sodium sulphate and evaporated to dryness under reduced pressure. The residue is recrystallized from diethyl ether/n-hexane. Via ethyl 3-[3-(4-chloro-2-fluoro-5 -isopropoxyphenyl)ureido]-4,4,4-trifluorocrotonate (m.p. 144°–146° C.), which is not isolated, there is obtained 3-(4-chloro-2-fluoro-5-isopropoxyphenyl)-6 -trifluoromethyl-2,4(1H,3H)-pyrimidinedione, m.p. 195°–197° C.

In an analogous manner, using ethyl 3-amino-4,4,4-trifluorocrotonate and:

4-chloro-2-fluoro-5-methoxyphenyl isocyanate there is obtained 3-(4-chloro-2-fluoro-5-methoxyphenyl)-6-trifluoromethyl-2,4(1H,3H)-pyrimidinedione, m.p 172°–174° C.; 4-chloro-2-fluoro-5-propoxyphenyl isocyanate there is obtained 3-(4-chloro-2-fluoro-5-propoxyphenyl)-6-trifluoromethyl-2,4(1H,3H)-pyrimidinedione, m.p. 164°–166° C.

5-butoxy-4-chloro-2-fluorophenyl isocyanate there is obtained 3-(5-butoxy-4-chloro-2-fluorophenyl)-6-trifluoromethyl-2,4(1H,3H)-pyrimidinedione, m.p. 153°–155° C.:

5-ethoxy-4-chloro-2-fluorophenyl isocyanate there is obtained 3-(5-ethoxy-4-chloro-2-fluorophenyl)-6-trifluoromethyl-2,4(1H,3H)-pyrimidinedione, m.p. 162°–165° C.;

ethyl 2-(2-chloro-4-fluoro-5-isocyanatophenoxy)propionate there is obtained ethyl 2-[2-chloro-5-(3,6-dihydro-2,6-dioxo-4-trifluoromethyl-1(2H)-pyrimidinyl)-4-fluorophenoxy]-propionate, m.p. 144°–146° C.;

5-allyloxy-4-chloro-2-fluorophenyl isocyanate there is obtained 3-(5-allyloxy-4-chloro-2 -fluorophenyl)-6-trifluoromethyl-2,4(1H,3H)-pyrimidinedione, m p. 119°–122° C.;

4-chloro-2-fluoro-5-propargyloxyphenyl isocyanate there is obtained 3-(4-chloro-2-fluoro-5-propargyloxyphenyl)-6-trifluoromethyl-2,4(1H,3H)-pyrimidinedione, m.p. 137°–140° C.;

4-bromo-2-fluoro-5-isopropoxyphenyl isocyanate there is obtained 3-(4-bromo-2-fluoro-5-isopropoxyphenyl)-6-trifluoromethyl-2,4(1H,3H)-pyrimidinedione, m.p. 182° C.

In an analogous manner:

using ethyl 3-amino-2,4-difluorocrotonate and 4-chloro-2-fluoro-5-isopropoxyphenyl isocyanate there is obtained 3-(4-chloro-2-fluoro-5-isopropoxyphenyl)-5-fluoro-6-fluoromethyl-2,4(1H,3H)-pyrimidinedione, m.p. 152°–154° C.;

using ethyl 3-amino-4,4,5,5,5-pentafluoro-2-pentenoate and 4-chloro-2-fluoro-5-isopropoxyphenyl isocyanate there is obtained 3- 4-chloro-2-fluoro-5-isopropoxyphenyl)-6-pentafluoroethyl-2,4(1H,3H)-pyrimidinedione, m.p. 141°-143° C.;

using ethyl 3-amino-2,4,4,5,5,5-hexafluoro-2-pentenoate and 4-chloro-2-fluoro-5-isopropoxyphenyl isocyanate there is obtained 3-(4-chloro-2-fluoro-5-isopropoxyphenyl)-5 -fluoro-6-pentafluoroethyl-2,4(1H,3H)-pyrimidinedione, m.p. 160°-162° C.;

using ethyl 3-amino-2,4,4,4-tetrafluorocrotonate and 4-chloro-2-fluoro-5-isopropoxyphenyl isocyanate there is obtained 3-(4-chloro-2-fluoro-5-isopropoxyphenyl)-5-fluoro-6-trifluoromethyl-2,4(1H,3H)-pyrimidinedione, m.p. 133°-135° C.

EXAMPLE 2

7.00 g of 4-chloro-2-fluoro-5-isopropoxyphenylurea and 4.44 g of ethyl cyclopentanone-2-carboxylate are heated at reflux temperature for 1.5 hours with 0.3 g of toluene-4-sulphonic acid monohydrate in 150 ml of benzene. The water which forms is removed with a water separator. The reaction mixture is subsequently evaporated to dryness and the residue is purified by chromatography on a silica gel column using methylene chloride as the eluent and recrystallized from diethyl ether/n-hexane. There is obtained ethyl 2-[3-(4-chloro-2-fluoro-5 -isopropoxyphenyl)-ureido]-1-cyclopentenecarboxylate, m.p. 166°-169° C.

A suspension of 6.0 g of ethyl 2-[3-(4-chloro-2-fluoro-5-isopropoxyphenyl)ureido]-1-cyclopentenecarboxylate in 100 ml of absolute methanol is treated while stirring at room temperature with 7.8 ml of 2N sodium methylate solution and the reaction mixture is stirred for 2 hours. The solution is treated with 7.8 ml of 2N hydrochloric acid and evaporated to dryness. The residue is dissolved in 200 ml of ethyl acetate and the solution is washed with water, dried over anhydrous sodium sulphate and evaporated to dryness under reduced pressure. The residue is recrystallized from methylene chloride/diethyl ether. There is obtained 3-(4-chloro-2-fluoro-5-isopropoxyphenyl)-1,5,6,7-tetrahydro-2H-cyclopenta[d]pyrimidine-2,4(3H)-dione, m.p. 215°-217° C.

In an analogous manner:

from 4-chloro-2-fluoro-5-isopropoxyphenylurea and ethyl acetoacetate using finely powdered Amberlyst ®-15 (an organic, polymeric resin having free sulphonyl groups) as the catalyst there is obtained ethyl 3-[3-(4-chloro-2-fluoro-5-isopropoxyphenyl)ureido]crotonate, m.p. 142°-144° C. and from this intermediate in dimethylformamide with sodium hydride there is obtained 3-(4-chloro-2-fluoro-5-isopropoxyphenyl)-6 -methyl-2,4(1H,3H)-pyrimidinedione, m.p. 228°-230° C.;

from 4-chloro-2-fluoro-5-isopropoxyphenylurea and ethyl 2-acetylpropionate using finely powdered Amberlyst ®-15 as the catalyst there is obtained ethyl 3-[3-(4-chloro-2-fluoro-5-isopropoxyphenyl)ureido]-2-methyl-crotonate and from this intermediate in dimethylformamide with sodium hydride there is obtained 3-(4-chloro-2-fluoro-5-isopropoxyphenyl)-5,6-dimethyl-2,4(1H,3H)pyrimidinedione, m.p. 125°-127° C.;

from 4-chloro-2-fluoro-5-isopropoxyphenylurea and ethyl 3-oxopentanoate using finely powdered Amberlyst ®-15 as the catalyst in cyclohexane there is obtained ethyl 3-[3-(4-chloro-2-fluoro-5-isopropoxyphenyl)ureido]-2-pentenoate, m.p. 118°-120° C. and from this intermediate with sodium hydride in dimethylformamide there is obtained 6-ethyl-3-(4-chloro-2-fluoro-5-isopropoxyphenyl)-2,4(1H,3H)-pyrimidinedione, m.p. 177°-179° C.:

from 4-chloro-2-fluoro 5-isopropoxyphenylurea and ethyl 3-oxohexanoate using finely powdered Amberlyst ®-15 as the catalyst in cyclohexane there is obtained ethyl 3-[3-(4-chloro-2-fluoro-5-isopropoxyphenyl)ureido]-2-hexenoate, m.p. 103°-105° C., and from this intermediate with sodium hydride in dimethylformamide there is obtained 3(4-chloro-2-fluoro-5 -isopropoxyphenyl)-6-propyl-O 2,4(1H,3H)-pyrimidinedione, m.p. 199°-200° C.;

from 4-chloro-2-fluoro-5-isopropoxyphenylurea and ethyl cyclohexanone-2-carboxylate using finely powdered Amberlyst ®-15 as the catalyst in cyclohexane there is 15 obtained ethyl 2-[3-(4-chloro-2-fluoro-5-isopropoxyphenyl)ureido]-1-cyclohexenecarboxylate, m.p. 133°-135° C., and from this intermediate with sodium hydride in methylformamide there is obtained 3-(4-chloro-2-fluoro-5-isopropoxyphenyl)-5,6,7,8-tetrahydro-2,4(1H,3H)-quinazolinedione, m.p. 201°-203° C.

EXAMPLE 3

A solution of 6.00 g of 4-chloro-2-fluoro-5-isopropoxyphenyl isocyanate in 100 ml of absolute diethyl ether is added dropwise while stirring at room temperature during 1 hour to a solution of 4.00 g of ethyl 3-amino-2-fluorocrotonate and the reaction mixture is stirred for 16 hours. The mixture is then evaporated to dryness under reduced pressure, the residue is dissolved in 50 ml of absolute dimethylformamide and the solution is added while stirring at room temperature to a solution of 1.31 g of a 55% sodium hydride dispersion in 50 ml of dimethylformamide and 100 ml of isopropyl alcohol. The mixture is subsequently stirred at room temperature for 4 hours, adjusted to pH ~4 with concentrated acetic acid and concentrated under reduced pressure. The residue is poured into 1 l of water and extracted twice with 200 ml of ethyl acetate each time, and the organic phases are washed with water, dried over anhydrous sodium sulphate and evaporated to dryness under reduced pressure. The residue is purified by chromatography on a silica gel column using ethyl acetate/n-hexane as the eluent and subsequently recrystallized from ethyl acetate/diethyl ether. There is obtained 3-(4-chloro-2-fluoro-5-isopropoxyphenyl)-5 -fluoro-6-methyl-2,4(1H,3H)-pyrimidinedione, m.p. 162°-164° C.

In an analogous manner:

using 4-chloro-2-fluoro-5-isopropoxyphenyl isocyanate in diethyl ether with ethyl 3-amino-2-methyl-2-pentenoate there is obtained ethyl 3-[3-(4-chloro-2-fluoro-5-isopropoxyphenyl)ureido]-2-methyl-2-pentenoate, m.p. 104°-106° C., and from this intermediate with sodium hydride in dimethylformamide there is obtained 6-ethyl-3-(4-chloro-2-fluoro-5-isopropoxyphenyl)-5 -methyl-2,4(1H,3H)-pyrimidinedione, m.p. 196°-198° C.:

using 4-chloro-2-fluoro-5-isopropoxyphenyl isocyanate in dimethylformamide with ethyl 3-amino-2-ethylcrotonate there is obtained ethyl 2-ethyl-3-[3-(4-chloro-2-fluoro-5-isopropoxyphenyl)ureido]-crotonate, m.p. 112°-114° C. and from this intermediate with sodium hydride in dimethylformamide there is obtained 5-ethyl-3-(4-chloro-2-fluoro-5-isopropoxyphenyl)-6-methyl-2,4(1H,3H)-pyrimidinedione, m.p. 128°-130° C.

EXAMPLE 4

A solution of 10.5 g of ethyl 3-amino-4,4,4-trifluorocrotonate in 25 ml of absolute dimethylformamide is added dropwise while stirring at 0° C. during 5 minutes to a suspension of 2.5 g of a 55% sodium hydride dispersion in 25 ml of absolute dimethylformamide. The temperature rises to 20° C. The mixture is subsequently stirred at this temperature for 30 minutes. Thereafter, 14.4 g of 4-chloro-2-fluoro-5-isopropoxyphenyl ethyl carbamate are added thereto, the mixture is stirred at room temperature for 30 minutes and heated to 150° C. (bath temperature) for 2.5 hours. The reaction mixture is cooled to 50° C., neutralized with 3.5 ml of concentrated acetic acid and largely concentrated at 60° C. under reduced pressure. The residue is poured into a solution of 200 ml of water and 30 ml of 2N hydrochloric acid and the aqueous mixture is extracted twice with 150 ml of diethyl ether each time, and the organic phases are washed twice with 50 ml of water each time, dried over anhydrous sodium sulphate and evaporated to dryness under reduced pressure. The residue is recrystallized from diethyl ether/n-hexane. There is obtained 3-(4-chloro-2-fluoro-5-isopropoxyphenyl)-6-trifluoromethyl-2,4(1H,3H)-pyrimidinedione, m.p. 195°–197° C.

EXAMPLE 5

A solution of 9.00 g of ethyl 3-[3-(4-chloro-2-fluoro-5-isopropoxyphenyl)ureido]-crotonate in 100 ml of anhydrous dimethylformamide is added dropwise at room temperature while stirring to a solution of 1.10 g of a 55% sodium hydride dispersion in 100 ml of isopropanol/dimethylformamide (1:1) and stirred for 1 hour. The reaction mixture is subsequently treated with 4.70 g of dimethYl sulphate and stirred at room temperature for 2 hours. The solvent is largely distilled off under reduced pressure and the residue is poured into 500 ml of water and extracted twice with 200 ml of ethyl acetate each time. The organic phases are washed with water, dried over anhydrous sodium sulphate and evaporated to dryness under reduced pressure. The residue is recrystallized from diethyl ether/n-hexane. There is obtained 3-(4-chloro-2-fluoro-5-isopropoxyphenyl)-1,6 -dimethyl-2,4(1H,3H)-pyrimidinedione, m.p. 149°–151° C.

EXAMPLE 6

8.0 g of 3-(4-chloro-2-fluoro-5-propargyloxyphenyl)-6-trifluoromethyl-2,4(1H,3H)-pyrimidinedione are added while stirring at 25° C. to a suspension of 0.96 g of a 55% sodium hydride dispersion in 25 ml of absolute dimethylformamide, After the hydrogen evolution has finished the reaction mixture is treated with 4.16 g of dimethyl sulphate, and the temperature rises to 30° C. during 15 minutes. The mixture is subsequently stirred at room temperature for 2 hours. The reaction mixture is poured into 800 ml of water and extracted twice with 100 ml of ethyl acetate each time, and the organic phases are washed twice with 50 ml of water each time and dried over anhydrous sodium sulphate. The solution is evaporated to dryness under reduced pressure and the residue is purified by chromatography on a silica gel column using diethyl ether/n-hexane (1:1) as the eluent. There is obtained 3-(4-chloro-2-fluoro-5-propargyloxyphenyl)-1-methyl-6-trifluoromethyl-2,4(1,3H)-pyrimidinedione, m.p. 87°–90° C.

In an analogous manner:

using 3-(4-chloro-2-fluoro-5-isopropoxyphenyl)-6-trifluoromethyl-2,4(1H,3H)-pyrimidinedione and dimethyl sulphate there is obtained 3-(4-chloro-2-fluoro-5-isopropoxyphenyl)-1-methyl-6-trifluoromethyl-2,4(1H,3H)-pyrimidinedione, m.p. 90°–93° C.;

using 3-(5-ethoxy-4-chloro-2-fluorophenyl)-6-trifluoromethyl- 2,4(1H,3H)-pyrimidinedione and dimethyl sulphate there is obtained 3-(5-ethoxy-4-chloro-2-fluorophenyl)-1-methyl-6 -trifluoromethyl-2,4(1H,3H)-pyrimidinedione, m.p. 118°–121° C.;

using 3-(4-chloro-2-fluoro-5-methoxyphenyl)-6-trifluoromethyl-2,4(1H,3H)-pyrimidinedione and dimethyl sulphate there is obtained 3-(4-chloro-2-fluoro-5-methoxyphenyl)-1-methyl-6-trifluoromethyl-2,4-(1H,3H)-pyrimidinedione, m.p. 128°–130° C.;

using ethyl 2-[2-chloro-5-(3,6-dihydro-2,6-dioxo-4-trifluoromethyl-1(2H)-pyrimidinyl)-4-fluorophenoxy]-propionate and dimethyl sulphate there is obtained ethyl 2-[2-chloro-5-(3,6-dihydro-2,6-dioxo-3-methyl-4-trifluoromethyl-1(2H)-pyrimidinyl)-4-fluorophenoxy]-propionate, $^1$H-NMR (CDCl$_3$, 400 MHz): 7.32 ppm (d,1H), 6.83 ppm (d,0.5H), 6.81 ppm (d,0.5H), 6.34 ppm (2s,1H), 4.53–4.72 ppm (m,1H), 4.13–4.27 ppm (m,2H), 3.50–3.59 ppm (m,3H), 1.67 ppm (d,3H), 1.18–1.28 ppm (m.3H):

using 3-(5-butoxy-4-chloro-2-fluorophenyl)-6-trifluoromethyl-2,4(1,3H)-pyrimidinedione and dimethyl sulphate there is obtained 3-(5-butoxy-4-chloro-2-fluorophenyl)-1-methyl-6 -trifluoromethyl-2,4(1,3H)-pyrimidinedione, m.p. 72°–74° C.;

using 3-(4-chloro-2-fluoro-5-propoxyphenyl)-6-trifluoromethyl-2,4(1,3H)-pyrimidinedione and dimethyl sulphate there is obtained 3-(4-chloro-2-fluoro-5-propoxyphenyl)-1-methyl-6-trifluoromethyl-2,4(1H,3H)-pyrimidinedione, m.p. 103°–104° C.;

using 3-(5-allyloxy-4-chloro-2-fluorophenyl)-6-trifluoromethyl-2,4(1H,3H)-pyrimidinedione and dimethyl sulphate there is obtained 3-(5-allyloxy-4-chloro-2-fluorophenyl)- 1-methyl-6-trifluoromethyl-2,4(1,3H)pyrimidinedione, m.p. 108°–110° C.:

using 3-(4-chloro-2-fluoro-5-isopropoxyphenyl)-1,5,6,7-tetrahydro-2H-cyclopenta[d]pyrimidine-2,4(3H)dione in sodium methylate/methanol with methyl iodide there is obtained 3-(4-chloro-2-fluoro-5-isopropoxyphenyl)-1,5,6,7-tetrahydro-1-methyl-2H-cyclopenta[d]-pyrimidine-2,4(3H)-dione, m.p. 125°–127° C.;

using 3-(4-chloro-2-fluoro-5-isopropoxyphenyl)-5,6-dimethyl-2,4(1H,3H)-pyrimidinedione and dimethyl sulphate there is obtained 3-(4-chloro-2-fluoro-5-isopropoxyphenyl)-1,5,6-trimethyl-2,4(1,3H)-pyrimidinedione, m.p. 105°–107° C.;

using 3-(4-chloro-2-fluoro-5-isopropoxyphenyl)-5-fluoro-6-fluoromethyl-2,4(1,3H)-pyrimidinedione and dimethyl sulphate there is obtained 3-(4-chloro-2-fluoro-5-isopropoxyphenyl)-5-fluoro-6-fluoromethyl-1-methyl-2,4(1H,3H)-pyrimidinedione, m.p. 88°–90° C.;

using 3-(4-chloro-2-fluoro-5-isopropoxyphenyl)-6-pentafluoroethyl-2,4(1,3H)-pyrimidinedione in acetone with sodium bicarbonate and dimethyl sulphate there is obtained 3-(4-chloro-2-fluoro-5-isopropoxyphenyl)-1-methyl-6-pentafluoroethyl-2,4(1,3H)-pyrimidinedione, m.p. 79°–81° C.;

using 3-(4-chloro-2-fluoro-5-isopropoxyphenyl)-5-fluoro-6-pentafluoroethyl-2,4(1H,3H)-pyrimidinedione in acetone with sodium bicarbonate and dimethyl sulphate there is obtained 3-(4-chloro-2-fluoro-5-isopropoxyphenyl)-5-fluoro-1-methyl-6-pentafluoroethyl-2,4(1H,3H)-pyrimidinedione, m.p. 107°–109° C.;

using 3-(4-chloro-2-fluoro-5-isopropoxyphenyl) 5-fluoro-6-trifluoromethyl-2,4(1,3H)-pyrimidinedione and dimethyl sulphate there is obtained 3-(4-chloro-2-fluoro-5-isopropoxyphenyl)-5-fluoro-1-methyl-6-trifluoromethyl-2,4(1H,3H)-pyrimidinedione, m.p. 104°–107° C.;

using 3-(4-chloro-2-fluoro-5-isopropoxyphenyl)-5-fluoro-6 methyl-2,4(1H,3H)-pyrimidinedione and dimethyl sulphate there is obtained 3-(4-chloro-2-fluoro-5-isopropoxyphenyl)-1,6-dimethyl-5-fluoro-2,4(1H,3H)pyrimidinedione, m.p. 139°–141° C.;

using 6-ethyl-3-(4-chloro-2-fluoro-5-isopropoxyphenyl)-2,4 (1H,3H)-pyrimidinedione and dimethyl sulphate there is obtained 6-ethyl-3-(4-chloro-2-fluoro-5-isopropoxyphenyl)-1-methyl-2,4(1H,3H)-pyrimidinedione, m.p. 72°–74° C.;

using 6-ethyl-3-(4-chloro-2-fluoro-5-isopropoxyphenyl)-5-methyl-2,4(1H,3H)-pyrimidinedione and dimethyl sulphate there is obtained 6-ethyl-3-(4-chloro-2-fluoro-5-isopropoxyphenyl)-1,5-dimethyl-2,4(1H,3H)-pyrimidinedione, m.p. 88°–91° C.;

using 5-ethyl-3-(4-chloro-2-fluoro-5-isopropoxyphenyl)-6-methyl-2,4(1H,3H)-pyrimidinedione and dimethyl sulphate there is obtained 5-ethyl-3-(4-chloro-2-fluoro-5-isopropoxyphenyl)-1,6-dimethyl-2,4(1H,3H)-pyrimidinedione, m.p. 124°–125° C.;

using 3-(4-chloro-2-fluoro-5-isopropoxyphenyl)-6-propyl-2,4 1,3H)-pyrimidinedione and dimethyl sulphate there is obtained 3-(4-chloro-2-fluoro-5-isopropoxyphenyl)-1-methyl-6-propyl-2,4(1H,3H)-pyrimidinedione, m.p. 115°–117° C.;

using 3-(4-bromo-2-fluoro-5-isopropoxyphenyl)-6-trifluoromethyl-2,4(1H,3H)-pyrimidinedione with potassium carbonate and methyl iodide in acetonitrile there is obtained 3-(4-bromo-2-fluoro-5-isopropoxyphenyl)-1-methyl-6-trifluoromethyl-2,4(1H,3H)-pyrimidinedione, m.p. 79° C.;

using 3-(4-chloro-2-fluoro-5-isopropoxyphenyl)-6-trifluoromethyl-2,4(1H,3H)-pyrimidinedione with potassium carbonate and ethyl chloroformate in acetone there is obtained 1-ethoxycarbonyl-3-(4-chloro-2-fluoro-5-isopropoxyphenyl)-6-trifluoromethyl-2,4(1H,3H)-pyrimidinedione, $^1$H-NMR (CDCl$_3$, 400 MHz): 7.30 ppm (d,1H), 6.83 ppm (d,1H), 6.37 ppm (s,1H), 4.51 ppm (q,2H), 4.45 ppm (m,1H), 1.42 ppm (t,3H), 1.37 ppm (d,6H);

using allyl bromide and sodium hydride in dimethylformamide there is obtained 1-allyl-3-(4-chloro-2-fluoro-5-isopropoxyphenyl)-6-trifluoromethyl-2,4(1H,3H)-pyrimidinedione, $^1$H-NMR (CDCl$_3$, 400 MHz): 7.29 ppm (d,1H), 6.81 ppm (d,1H), 6.37 ppm (s,1H), 5.2 ppm (m,1H), 5.25–5.34 ppm (m,2H), 4.56 ppm (m,2H), 4.45 ppm (m,1H), 1.37 ppm (d,6H):

using chloromethyl methyl ether and sodium hydride in dimethylformamide there is obtained 3-(4-chloro-2-fluoro-5-isopropoxyphenyl)-1-methoxymethyl-6-trifluoromethyl-2,4(1H,3H)-pyrimidinedione $^1$H-NMR (CDCl$_3$, 400 MHz): 7.30 ppm (d,1H), 6.82 ppm (d,1H), 6.40 ppm (s,1H), 5.37 ppm (q,2H), 4.45 ppm (m,1H), 3.49 ppm (s,3H), 1.37 ppm (d,6H):

using 3-bromo-1-propyne and sodium hydride in dimethylformamide there is obtained 3-(4-chloro-2-fluoro-5-isopropoxyphenyl)-1-(2-propynyl)-6-trifluoromethyl-2,4(1H,3H)-pyrimidinedione, $^1$H-NMR (CDCl$_3$, 400 MHz): 7.30 ppm (d,1H), 6.84 ppm (d,1H), 6.40 ppm (s,1H), 4.72 ppm (m,2H), 4.46 ppm (m,1H), 2.36 ppm (t,1H), 1.38 ppm (d,3H), 1.37 ppm (d,3H):

using 3-(4-chloro-2-fluoro-5-isopropoxyphenyl)-5,6,7,8-tetrahydro-2,4(1H,3H)-quinazolinedione with dimethyl sulphate and sodium hydride in dimethylformamide there is obtained 3-(4-chloro-2-fluoro-5-isopropoxyphenyl)-1-methyl-5,6,7,8-tetrahydro-2,4(1H,3H)-quinazolinedione, m.p. 143°–145° C.

EXAMPLE 7

A solution of 2.00 g of 3-(4-chloro-2-fluoro-5-isopropoxyphenyl)-6-methyl-2,4(1H,3H)-pyrimidinedione in 20 ml dimethylformamide is added dropwise at room temperature while stirring within 30 minutes to a suspension of 0.28 g of a 55% sodium hydride dispersion in 10 ml of dimethylformamide. The mixture is subsequently stirred for 30 minutes and thereafter 5.26 g of chlorodifluoromethane are introduced at 55° C. while stirring during 18 hours. The reaction mixture is cooled, poured into a solution of 20 ml of 2N hydrochloric acid in 300 ml of water and extracted with 150 ml of ethyl acetate. The organic phase is washed twice with 100 ml of water each time, dried over anhydrous sodium sulphate and evaporated to dryness under reduced pressure. The residue is dissolved in 100 ml of diethyl ether and the solution is treated with active carbon and filtered. The filtrate is evaporated to dryness and the residue is recrystallized from diethyl ether/n-hexane. There is obtained 3-(4-chloro-2-fluoro-5-isopropoxyphenyl)-1-difluoromethyl-6-methyl-2,4(1H,3H)-pyrimidinedione, m.p. 97°–99° C.

EXAMPLE 8

A solution of 2.00 g of 3-(4-chloro-2-fluoro-5-hydroxyphenyl)-1-methyl-6-trifluoromethyl-2,4(1H,3H)-pyrimidinedione in 20 ml of dimethylformamide is added to a suspension of 0.26 g of a 55% sodium hydride dispersion in 20 ml of absolute dimethylformamide and the mixture is stirred at room temperature until the hydrogen evolution has finished. Subsequently, 0.57 g of chlorodimethyl ether is added and the mixture is stirred at room temperature for 2 hours. The reaction mixture is evaporated to dryness under reduced pressure, the residue is taken up in 100 ml of ethyl acetate and the solution is washed twice with water, dried over anhydrous sodium sulphate and evaporated to dryness under reduced pressure. The residue is purified by chromatography on a silica gel column using diethyl ether/n-hexane as the eluent. There is obtained 3-(4-chloro-2-fluoro-5-methoxymethoxy-phenyl)-1-methyl-6-trifluoromethyl-2,4(1H,3H)-pyrimidinedione, $^1$H-NMR (CDCl$_3$, 400 MHz): 7.31 ppm (d,1H), 7.12 ppm (d,1H), 6.36 ppm (s,1H), 5.22 ppm (d,1H), 5.19 ppm (d,1H), 3.55 ppm (d,3H), 3.51 ppm (s,3H).

In an analogous manner:

using methyl chloroformate with pyridine in methylene chloride there is obtained [2-chloro-5-(3,6-dihydro-3-methyl-4-trifluoromethyl-2,6-dioxo-1(2H)-pyrimidinyl)-4-fluorophenyl]methyl carbonate, $^1$H-NMR (CDCl$_3$, 400 MHz): 7.38 ppm (d,1H), 7.24 ppm (d,1H), 6.36 ppm (s,1H), 3.93 ppm (s,3H), 3.55 ppm (d,3H);

using butyl chloroformate with pyridine in methylene chloride there is obtained butyl [2-chloro-5-(3,6-dihydro-3-methyl-4-trifluoromethyl-2,6-dioxo-1(2H)-pyrimidinyl)-4-fluorophenyl] carbonate, $^1$H-NMR (CDCl$_3$, 400 MHz): 7.37 ppm (d,1H), 7.24 ppm (d,1H), 6.35 ppm (s,1H), 4.29 ppm (t,2H), 3.55 ppm (d,3H), 1.73 ppm (m,2H), 1.45 ppm (m,2H), 0.97 ppm t,3H);

using isopropyl chloroformate with pyridine in methylene chloride there is obtained 2-chloro-5-(3,5-dihydro-3-methyl-4-trifluoromethyl-2,6-dioxo-1(2H)-pyrimidinyl-4-fluorophenyl isopropyl carbonate, $^1$H-NMR (CDCl$_3$, 400 MHz): 7.37 ppm (d,1H), 7.24 ppm (d,1H), 6.35 ppm (s,1H), 4.99 ppm (m,1H), 3.55 ppm (d,3H), 1.38 ppm (d,6H);

using vinyl chloroformate with pyridine in methylene chloride there is obtained 2-chloro-5-(3,6-dihydro-3-methyl-4-trifluoromethyl-2,6-dioxo-1(2H)-pyrimidinyl)-4-fluorophenyl vinyl carbonate, $^1$H-NMR (CDCl$_3$, 400 MHz): 7.40 ppm (d,1H), 7.28 ppm (d,1H), 7.11 ppm (q,1H), 6.36 ppm (s,1H), 5.08 ppm (q,1H), 4.73 ppm (q,1H), 3.55 ppm (d,3H);

using cyclohexyl chloroformate with pyridine in methylene chloride there is obtained 2-chloro-5-(3,6-dihydro-3-methyl-4-trifluoromethyl-2,6-dioxo-1(2H)-pyrimidinyl)-4-fluorophenyl cyclohexyl carbonate, $^1$H-NMR (CDCl$_3$, 400 MHz): 7.37 ppm (d,1H), 7.24 ppm (d,1H), 6.36 ppm (s,1H), 4.69-4.79 ppm (m,1H), 3.56 ppm (d,3H), 1.22-2.04 ppm (4m,10H);

usinq allyl chloroformate with pyridine in methylene chloride there is obtained allyl [2-chloro-5-(3,6-dihydro-3-methyl-4-trifluoromethyl-2,6-dioxo-1(2H)-pyrimidinyl)-4-fluorophenyl] carbonate, $^1$H-NMR (CDCl$_3$, 400 MHz): 7.38 ppm (d,1H), 7.25 ppm (d,1H), 6.36 ppm (s,1H), 5.93-6.05 ppm (m,1H), 5.40-5.48 ppm (m,1H), 5.32-5.38 ppm (m,1H), 4.73-4.79 ppm (m,2H), 3.55 ppm (d,3H);

using 2-propynyl chloroformate with pyridine in methylene chloride there is obtained 2-chloro-5-(3,6-dihydro-3-methyl-4-trifluoromethyl-2,6-dioxo-1(2H)-pyrimidinyl-4-fluorophenyl 2-propynyl carbonate, $^1$H-NMR (CDCl$_3$, 400 MHz): 7.39 ppm (d,1H), 7.27 ppm (d,1H), 6.36 ppm (s,1H), 4.86 ppm (d,2H), 3.55 ppm (d,3H), 2.60 ppm (t,1H);

using acetyl chloride with pyridine in methylene chloride there is obtained 2-chloro-5-[3,6-dihydro-3-methyl-4-trifluoromethyl-2,6-dioxo-1(2H)-pyrimidinyl]-4-fluorophenyl acetate, m.p. 99°-101° C.;

using isobutyryl chloride with pyridine in methylene chloride there is obtained 2-chloro-5-[3,6-dihydro-3-methyl-4-trifluoromethyl-2,6-dioxo-1(2H)-pyrimidinyl]-4-fluorophenyl isobutyrate, $^1$H-NMR (CDCl$_3$, 60 MHz): 7.35 ppm (d,1H), 7.13 ppm (d,1H), 6.34 ppm (s,1H), 3.56 ppm (d,3H), 2.50-3.20 ppm (m,1H), 1.34 ppm (d,6H);

using 2,4-dichlorbenzoyl chloride with pyridine in methylene chloride there is obtained 2-chloro-5-[3,6-dihydro-3-methyl-4-trifluoromethyl-2,6-dioxo-1(2H)-pyrimidinyl]-4-fluorophenyl 2,4-dichlorobenzoate. $^1$H-NMR (CDCl$_3$, 400 MHz): 8.11 ppm (d,1H), 7.57 ppm (d,1H), 7.43 ppm (d,1H), 7.41 ppm (q,1H), 7.33 ppm (d,1H), 6.37 ppm (s,1H), 3.57 ppm (d,3H);

using acryloyl chloride with sodium hydride in dimethylformamide there is obtained 2-chloro-5-[3,6-dihydro-3-methyl-4-trifluoromethyl-2,6-dioxo-1(2H)-pyrimidinyl]-4fluorophenyl acrylate, $^1$H-NMR (CDCl$_3$, 400 MHz): 7.39 ppm (d,1H), 7.22 ppm (d,1H), 6.67 ppm q,1H), 6 36 ppm (s,1H), 6.33 ppm (q,1H), 6.09 ppm (q,1H), 3.55 ppm (d,3H);

using 1,2-dibromoethene with sodium hydride in dimethylformamide there is obtained 3-[5-(2-bromoethoxy)-4-chloro-2-fluorophenyl]-1-methyl -6-trifluoromethyl-2,4(1H,3H)-pyrimidinedione, m.p. 125°-127° C.;

using 1-bromo-3,3-dichloro-2-propene with sodium hydride in dimethylformamide there is obtained 3-[4-chloro-5-(3,3-dichloro-2-propenyloxy)-2 -fluorophenyl]-1-methyl-6-trifluoromethyl-2,4(1H,3H) -pyrimidinedione, m.p. 126°-127° C.;

using 2-(2,2-dichlorovinyloxy)ethyl bromide with sodium hydride in dimethylformamide there is obtained 3-{4-chloro-5-[2-(2,2 -dichlorovinyloxy)ethoxy]-2-fluorophenyl}-1-methyl-6 -trifluoromethyl-2,4(1H,3H)-pyrimidinedione, m.p. 97°-99° C.;

using 2-(2-methoxyethoxy)ethyl bromide with sodium hydride in dimethylformamide there is obtained 3-{4-chloro-2-fluoro-5-[2-(2-methoxyethoxy)ethoxy]-phenyl}-1-methyl-6-trifluoromethyl-2,4(1H,3H)-pyrimidinedione, $^1$H-NMR (CDCl$_3$, 400 MHz): 7.30 ppm (d,1H), 6.86 ppm (d,1H), 6.36 ppm (s,1H), 4.17 ppm (t,2H), 3.89 ppm (t,2H), 3.72-3.78 ppm (m,2H), 3.53-3.59 ppm (m,5H), 3.39 ppm (s,3H);

using 2-vinyloxyethyl chloride with sodium hydride in dimethylformamide there is obtained 3-{4-chloro-2-fluoro-5-[2-(vinyloxy)ethoxy]-phenyl}-1-methyl-6-trifluoromethyl-2,4(1H,3H)-pyrimidinedione, $^1$H-NMR (CDCl$_3$, 400 MHz): 7.32 ppm (d,1H), 6.85 ppm (d,1H), 6.53 ppm (q,1H), 6.37 ppm (s,1H), 4.19-4.29 ppm (m,3H), 4.03-4.10 ppm (m,3H), 3.56 ppm (d,3H):

using chloroacetone with sodium hydride in dimethylformamide there is obtained 3-(5-acetonyloxy-4-chloro-2-fluorophenyl)- 1-methyl-6-trifluoromethyl-2,4(1H,3H)pyrimidinedione, m.p. 164°-166° C.;

using chlorodimethyl sulphide with sodium hydride in dimethylformamide there is obtained 3-[4-chloro-2-fluoro-5-(methylthiomethoxy)-phenyl]-1-methyl-6-trifluoromethyl-2,4(1H,3H)-pyrimidinedione, $^1$H-NMR (CDCl$_3$, 400 MHz): 7.32 ppm (d,1H), 6.93 ppm (d,1H), 6.36 ppm (s,1H), 5.18 ppm (s,2H), 3.56 ppm (d,3H), 2.27 ppm (s,3H):

using 2-methoxyethyl bromide with sodium hydride in dimethylformamide there is obtained 3-[4-chloro-2-fluoro-5-(2-methoxyethoxy)-phenyl]-1-methyl-6-trifluoromethyl-2,4(1H,3H)-pyrimidinedione, m.p. 84°-87° C.;

using 2-ethoxyethyl bromide with sodium hydride in dimethylformamide there is obtained 3-[5-(2-ethoxyethoxy)-4-chloro-2-fluorophenyl]-1-methyl-6-trifluoromethyl-2,4(1H,3H)-pyrimidinedione, $^1$H-NMR (CDCl$_3$, 400 MHz): 7.30 ppm (d,1H), 6.86 ppm (d,1H), 6.36 ppm (s,1H), 4.14 ppm (t,2H), 3.81 ppm (t,2H), 3.61 ppm (q,2H), 3.55 ppm (d,3H), 1.22 ppm (t,3H);

using 4-chlorophenoxymethyl chloride with sodium hydride in dimethylformamide there is obtained 3-[4-chloro-5-(4-chlorophenoxymethoxy)-2-fluorophenyl]-1-methyl-6-trifluoromethyl-2,4(1H,3H)-pyrimidinedione, m.p. 120°-122° C.;

using benzyl bromide with sodium hydride in dimethylformamide there is obtained 3-(5-benzyloxy-4-chloro-2-fluorophenyl)-1-methyl -6-trifluoromethyl-2,4(1H,3H)-pyrimidinedione, m.p. 129°-131° C.;

using 4-phenoxy-2-butynyl bromide with sodium hydride in dimethylformamide there is obtained 3-[4-chloro-2-fluoro- 5-(4-phenoxy-2-butynyloxy)-phenyl]-1-methyl-6-trifluoromethyl-2,4(1H,3H)-pyrimidinedione, m.p. 142°-144° C.;

using N,N-dimethylchloroacetamide with sodium hydride in dimethylformamidethere is obtained 3-[4-chloro-5-(dimethylaminocarbonylmethocy)-2-fluorophenyl]-1-methyl-6-trifluoromethyl-2,4(1H,3H)-pyrimidinedione, m.p. 178°-180° C.;

using dimethylcarbamoyl chloride and pyridine in methylene chloride there is obtained 2-chloro-5-[3,6-dihydro-3-methyl-4-trifluoromethyl-2,6-dioxo-1(2H)-pyrimidinyl]-4-fluorophenyl dimethylcarbamate, $^1$H-NMR (CDCl$_3$, 400 MHz): 7.34 ppm (d,1H), 7.27 ppm (d,1H), 6.34 ppm (s,1H), 3.54 ppm (d,3H), 3.13 ppm (s,3H), 3.02 ppm (s,3H);

using 4-chlorobenzenesulphonyl chloride and triethylamine in methylene chloride there is obtained 2-chloro-5-[3,6-dihydro-3-methyl-4-trifluoromethyl-2,6-dioxo-1(2H)-pyrimidinyl]-4-fluorophenyl 4-chlorobenzenesulphonate, m.p. 152°–154° C.;

using dimethylsulphamoyl chloride and triethylamine in methylene chloride there is obtained 2-chloro-5-[3,6-dihydro-3-methyl-4-trifluoromethyl-2,6-dioxo-1(2H)-pyrimidinyl]-4-fluorophenyl dimethylsulphamate, m.p. 118°–120° C.;

using methanesulphonyl chloride and pyridine in methylene chloride there is obtained 2-chloro-5-[3,6-dihydro-3-methyl-4-trifluoromethyl-2,6-dioxo-1(2H)-pyrimidinyl]-4-fluorophenyl methanesulphonate, m.p. 176°–178° C.;

using chlorodifluoromethane and sodium hydride in dimethylformamide there is obtained 3-(4-chloro-5-difluoromethoxy-2-fluorophenyl)-1-methyl-6-trifluoromethyl-2,4(1H,3H)-pyrimidinedione, $^1$H-NMR (CDCl$_3$, 400 MHz); 7.39 ppm (d,1H), 7.21 ppm (d,1H), 6.52 ppm (t,b 1H), 6.37 ppm (s,1H), 3.56 ppm (d,3H);

using 5-chloro-1-methyl-3-trifluoromethyl-1H-1,2,4-triazole with sodium hydride in dimethylformamide there is obtained 3-[4-chloro-2-fluoro-5-[(1-methyl-3-trifluoromethyl-1H -1,2,4-triazol-5-yl)oxy]-phenoxy}-1-methyl-6 -trifluoromethyl-2,4(1H,3H)-pyrimidinedione, m.p. 138°–140° C.;

using 1,4-dichloro-2-butene with sodium hydride in dimethylformamide there is obtained 3-{4-chloro-5-[(E/Z)-4-chloro-2-butenyl)oxy]-2 -fluoro-phenyl}-1-methyl-6 -trifluoromethyl-2,4(1H,3H)-pyrimidinedione, $^1$H-NMR (CDCl$_3$, 400 MHz): 7.32 ppm (2d, 1H), 6 82 ppm, 6.78 ppm (2d,1H), 6.37 ppm (s,1H), 5.96–6.07 ppm (m,1H), 5.85–5.96 ppm (m,1H), 4.65–4.70 ppm (m,1H), 4.54–4.59 ppm (m,1H), 4.07–4.18 ppm (m,2H), 3.56 ppm (m,3H);

using cyclopropylmethyl chloroformate with pyridine in methylene bhloride there is obtained 2-chloro-5-[3,6-dihydro-2,6-dioxo-3-methyl-4-trifluoromethyl-1(2H)-pyrimidinyl]-4 -fluoro-phenyl cyclopropylmethyl carbonate, $^1$H-NMR (CDCl$_3$, 400 MHz): 7.38 ppm (d,1H), 7.26 ppm (d,1H), 6.36 ppm (s,1H), 4.12 ppm (m,2H), 3.55 ppm (m,3H), 0.30–0.44 ppm (m,2H);

using 2,2,2-trichloroethyl chloroformate with pyridine in methylene chloride there is obtained 2-chloro-5-[3,6-dihydro-2,6-dioxo-3-methyl-4 -trifluoromethyl-1(2H)-pyrimidinyl]-4-fluorophenyl 2,2,2-trichloroethyl carbonate, m.p. 140°–142° C.;

using 2-chloroethyl chloroformate with pyridine in methylene chloride there is obtained 2-chloroethyl 2-chloro-5-[3,6-dihydro-2,6 -dioxo-3-methyl-4-trifluoromethyl-1(2H)-pyrimidinyl]-4-fluorophenyl carbonate, $^1$H-NMR (CDCl$_3$, 400 MHz): 7.39 ppm (d,1H), 7.26 ppm (d,1H), 6.36 ppm (s,1H), 4.52 ppm (t,2H), 3.78 ppm (t,2H), 3.55 ppm (d,3H);

using benzyl chloroformate with pyridine in methylene chloride there is obtained benzyl 2-chloro-5-[3,6-dihydro-2,6-dioxo-3-methyl-4-trifluoromethyl-1(2H)-pyrimidinyl]-4-fluorophenyl carbonate, $^1$H-NMR (CDCl$_3$, 400 MHz): 7.33–7.46 ppm (m,6H), 7.25 ppm (d,1H), 6.35 ppm (s,1H), 5.29 ppm (s,2H), 3.55 ppm (d,3H);

using N-chloromethylsuccinimide with sodium hydride in dimethylformamide there is obtained N-[[2-chloro-5-(3,6-dihydro-2,6-dioxo-3-methyl-4-trifluoromethyl-1(2H)-pyrimidinyl)-4-fluorophenoxy]methyl}-succinimide, m.p. 212°–214° C.;

using cyclohexylmethyl chloroformate with pyridine in methylene chloride there is obtained 2-chloro-5-[3,6-dihydro-2,6-dioxo-3-methyl-4 -trifluoromethyl-1(2H)-pyrimidinyl]-4-fluoro-phenyl cyclohexylmethyl carbonate, $^1$H-NMR (CDCl$_3$, 60 MHz): 7.37 ppm (d,1H), 7.24 ppm (d,1H), 6.35 ppm (s,1H), 4.09 ppm (d,2H), 3.57 ppm (d,3H), 0.5–2.2 ppm (m,11H);

using ethyl dithiochloroformate with sodium hydride in dimethylformamide there is obtained O-[2-chloro-5-[3,6-dihydro-2,6-dioxo-3-methyl-4 -trifluoromethyl-1(2H)-pyrimidinyl]-4 -fluorophenyl-S-ethyldithiocarbonate, $^1$H-NMR (CDCl$_3$, 400 MHz): 7.38 ppm (d,1H), 7.13 ppm (d,1H), 6.36 ppm (s,1H), 3 55 ppm (d,3H), 3.24 ppm (q,2H), 1.43 ppm (t,3H);

using ethyl 2-chloroethylcarbamate with sodium hydride in dimethylformamide there is obtained ethyl [2-{2-chloro-5-[3,6-dihydro-2,6 -dioxo-3-methyl-4-trifluoromethyl-1(2H)-pyrimidinyl]-4 -fluorophenoxy}-ethyl]carbamate, $^1$H-NMR (CDCl$_3$, 400 MHz): 7.31 ppm (d,1H), 6.79 ppm (d,1H), 6.36 ppm (s,1H), 5.20 ppm (t,1H), 4.13 ppm q,2H), 4.04 ppm (t,22H), 3.60 ppm (q,2H), 3.55 ppm (d,3H), 1.25 ppm (t,3H);

using ethyl N-(2-chloroethyl)-N-methylcarbamate with sodium hydride in dimethylformamide there is obtained ethyl N-[2-{2-chloro-5[3,6-dihydro-2,6-dioxo-3-methyl-4-trifluoromethyl-1(2H)-pyrimidinyl]-4 -fluorophenoxy}-ethyl]-N-methylcarbamate, $^1$H-NMR (CDCl$_3$, 400 MHz): 7.32 ppm (d,1H), 6.77 ppm (d,1H), 6.36 ppm (s,1H), 4.01–4.20 ppm (m,4H), 3.68 ppm (t,2H), 3.56 ppm (d,3H), 3.09 ppm (s,3H), 1.26 ppm (t,3H);

using ethyl chlorosulphate in toluene there is obtained 2-chloro-5-[3,6-dihydro-2,6 -dioxo-3-methyl-4-trifluoromethyl-1(2H)-pyrimidinyl]-4 -fluorophenyl ethyl sulphate, $^1$H-NMR (CDCl$_3$, 400 MHz): 7.48 ppm (d,1H), 7.41 ppm (d,1H), 6.36 ppm (s,1H), 4.60 ppm (q,2H), 3.55 ppm (d,3H), 1.47 ppm (t,3H);

using dimethylthiocarbamoyl chloride with sodium hydride in dimethylformamide there is obtained O-{2-chloro-5-[3,6-dihydro-2,6-dioxo-3-methyl-4 -trifluoromethyl-1(2H)-pyrimidinyl]-4 -fluorophenyl}-dimethylthiocarbamate, $^1$H-NMR (CDCl$_3$, 400 MHz): 7.35 ppm (d,1H), 7.13 ppm (d,1H), 6.35 ppm (s,1H), 3.56 ppm (d,3H), 3.45 ppm (s,3H), 3.37 ppm (s,3H);

using S-ethyl thiochloroformate with pyridine in methylene chloride there is obtained O-{2-chloro-5-[3,6-dihydro-2,6-dioxo-3-methyl-4 -trifluoromethyl-1(2H)-pyrimidinyl]-4 -fluorophenyl}-S-ethylthiocarbonate, $^1$H-NMR (CDCl$_3$, 400 MHz): 7.38 ppm (d,1H). 7.23 ppm (d,1H). 6.36 ppm (s,1H), 3.56 ppm (d,3H), 2.97 ppm (q,2H), 1.38 ppm (t,3H):

using isopropanesulphochloride with pyridine in methylene chloride there is obtained 2-chloro-5-[3,6-dihydro-2,6-dioxo-3-methyl-4 -trifluoromethyl-1(2H)-pyrimidinyl]-4-fluorophenyl isopropanesulphonate, $^1$H-NMR (CDCl$_3$, 400 MHz): 7.46 ppm (d,1H). 7.39 ppm (d,1H). 6.36 ppm (s,1H), 3.58 ppm (septet,1H). 3.55 ppm (d,3H). 1.60 ppm (2d,6H);

using cyclohexanoyl chloride with pyridine in methylene chloride there is obtained 2-chloro-5-[3,6-dihydro-2,6-dioxo-3-methyl-4 -trifluoromethyl-1(2H)- pyrimidinyl]-4-fluorophenyl cyclohexanecarboxylate, m.p. 97°–101° C.;

using O-ethyl thiochloroformate with pyridine in methylene chloride there is obtained O-{2-chloro-5-[3,6-dihydro-2,6-dioxo-3-methyl-4 -trifluoromethyl-1(2H)-pyrimidinyl]-4 -fluorophenyl}-O-ethylthiocarbonate, m p. 101°–102° C.;

using 2-methoxyethyl chloroformate with pyridine in methylene chloride there is obtained 2-chloro-5-[3,6-dihydro-2,6-dioxo-3-methyl-4 -trifluoromethyl-1(2H)-pyrimidinyl]-4-fluorophenyl 2-methoxyethyl carbonate, $^1$H-NMR (CDCl$_3$, 250 MHz); 7.38 ppm (d,1H), 7.25 ppm (d,1H), 6.35 ppm s,1H), 4.42 ppm (quintet,2H), 3.68 ppm (quintet,2H), 3.54 ppm (d,3H), 3.41 ppm (s,3H);

using cyclopropanoyl chloride with pyridine in methylene chloride there is obtained 2-chloro-5-[3,6-dihydro-2,6-dioxo-3-methyl-4 -trifluoromethyl-1(2H)-pyrimidinyl]-4 -fluorophenyl cyclopropanecarboxylate, $^1$H-NMR (CDCl$_3$, 250 MHz): 7.35 ppm (d,1H), 7.16 ppm (d,1H), 6.35 ppm (s,1H), 3.54 ppm (d,3H), 1.84–1.90 ppm (m,1H), 1.04–1.23 ppm (m,4H);

using thiophene-2-carbonyl chloride with pyridine in methylene chloride there is obtained 2-chloro-5-[3,6-dihydro-2,6-dioxo-3-methyl-4-trifluoromethyl-1(2H)-pyrimidinyl]-4 -fluorophenyl 2-thiophenecarboxylate, $^1$H-NMR (CDCl$_3$, 250 MHz): 8.02 ppm (q,1H), 7.71 ppm (q,1H), 7.41 ppm (d,1H), 7.32 ppm (d,1H), 7.20 ppm (q,1H), 6.36 ppm (s,1H), 3.56 ppm (d,3H);

using phenyl chloroformate with pyridine in methylene chloride there is obtained 2-chloro-5-[3,6-dihydro-2,6-dioxo-3-methyl-4 -trifluoromethyl-1(2H)-pyrimidinyl]-4-fluorophenyl phenyl carbonate, m.p. 112°–115° C.:

using monomethyl oxalyl chloride with pyridine in methylene chloride there is obtained 2-chloro-5-[3,6-dihydro-2,6-dioxo-3-methyl-4-trifluoromethyl-1(2H)-pyrimidinyl]-4-fluorophenyl methyl oxalate, m.p. 103°–105° C.;

using bromoacetaldehyde dimethyl acetal with sodium hydride in dimethylformamide there is obtained 1-[4-chloro-5-(2,2-dimethoxyethoxy)-2-fluorophenyl]-3-methyl-4-trifluoromethyl-2,6(1H,3H)-pyrimidinedione, $^1$H-NMR (CDCl$_3$, 250 MHz): 7.31 ppm (d,1H), 6.84 ppm (d,1H), 6.36 ppm (s,1H), 4.71 ppm (t,1H), 4.01 ppm (d,2H), 3.55 ppm (d,3H), 3.47 ppm (2s,6H);

using 2-bromomethyl-1H,3-dioxolan with sodium hydride in dimethylformamide there is obtained 1-{4-chloro-5-[(1,3-dioxolan-2-yl)methoxy]-2 -fluorophenyl}-3-methyl-4-trifluoromethyl-2,6(1H,3H)-pyrimidinedione $^1$-NMR (CDCl$_3$, 250 MHz): 7 31 ppm (d,1H) 6 84 ppm (d,1H), 6.36 ppm (s,1H), 5.33 ppm (t,1H), 3.92–4.20 ppm (m,6H), 3.55 ppm (d,3H);

using benzyl chloromethyl ether with sodium hydride in dimethylformamide there is obtained 1-{5-[(benzyloxy)methoxy]-4-chloro-2-fluorophenyl}-3-methyl-4-trifluoromethyl-2,6(1H,3H)-pyrimidinedione, $^1$H-NMR (CDCl$_3$, 250 MHz): 7.24–7.40 ppm (m,5H), 7.27 ppm (d,1H), 7.20 ppm (d,1H), 6.34 ppm (s,1H), 5.33 ppm (s,2H), 4.74 ppm (s,2H), 3.54 ppm (d,3H);

using chloromethyl propargyl ether with sodium hydride in dimethylformamide there is obtained 1-[4-chloro-2-fluoro-5-[(2 -propynyloxy)methoxy]-phenyl}-3-methyl-4 -trifluoromethyl-2,6(1H,3H)-pyrimidinedione, $^1$-NMR (CDCl$_3$, 250 MHz): 7.31 ppm (d,1H) 7.13 ppm (d,1H), 6.36 ppm (s,1H), 5.35 ppm (s,2H), 4.36 ppm (d,2H), 3.55 ppm (d,3H), 2.48 ppm (t,1H);

using bromomethylcyclohexane with sodium hydride in dimethylformamide there is obtained 1-(4-chloro-5-cyclohexylmethoxy-2-fluorophenyl)-3-methyl-4 -trifluoromethyl-2,6(1H,3H)-pyrimidinedione, $^1$H-NMR (CDCl$_3$, 250 MHz): 7.29 ppm (d,1H), 6.75 ppm (d,1H), 6.36 ppm (s,1H), 3.74 ppm (d,2H), 3.55 ppm (d,3H), 1.61–1.91 ppm (m,6H), 0.93–1.42 ppm (m,5H);

using allyl chloromethyl ether with sodium hydride in dimethylformamide there is obtained 1-{5-[(allyloxy)methoxy]-4-chloro-2-fluorophenyl}-3-methyl-4-trifluoromethyl-2,6(1H,3H)-pyrimidinedione, $^1$H-NMR (CDCl$_3$, 250 MHz): 7.30 ppm (d,1H), 7.15 ppm (d,1H), 6.35 ppm (s,1H), 5.79–6.00 ppm (m,1H), 5.27 ppm (s,2H), 5.16–5.32 ppm (m,2H), 4.23 ppm (sextet,2H), 3.55 ppm (t,3H);

using chloromethyl 4-chlorphenyl sulphide with sodium hydride in dimethylformamide there is obtained 1-[4-chloro-5-{[(p-chlorophenyl)thio]methoxy}-2 -fluorophenyl]-3-methyl-4-trifluoromethyl-2,6(1H,3H)-pyrimidinedione, m.p. 141°–142° C.;

using bromocyclopentane with sodium hydride in dimethylformamide there is obtained 1-(4-chloro-5-cyclopentyloxy-2-fluorophenyl)-3-methyl-4 -trifluoromethyl-2,6(1H,3H)-pyrimidinedione, m.p. 135°–137° C.;

using 1,4-dichloro-2-butyne with sodium hydride in dimethylformamide there is obtained 3-{4-chloro-5-[(4-chlor-2-butynyl)oxy]-2-fluorophenyl}-1 -methyl-6-trifluoromethyl-2,4(1H,3H)-pyrimidinedione. m.p. 118°–120° C.;

using 1-chloro-4-methoxy-2-butene with sodium hydride in dimethylformamide there is obtained 3-[4-chloro-2-fluoro-5-{[(E/Z)-4-methoxy-2 -butenyl]oxy}phenyl]-1-methyl-6 -trifluoromethyl-2,4(1H,3H)-pyrimidinedione m.p. 78°–83° C.:

using bromomethylcyclopropane with sodium hydride in dimethylformamide there is obtained 3-(4-chloro-5-cyclopropylmethoxy-2 -fluorophenyl)-1-methyl-6 -trifluoromethyl-2,4(1H,3H)-pyrimidindione. $^1$H-NMR (CDCl$_3$, 250 MHz): 7.31 ppm (d,1H), 6.77 ppm (d,1H), 6.36 ppm (s,1H), 3.83 ppm (d,2H), 3.55 ppm (d,3H), 1.29 ppm (m,1H), 0.64 ppm (m,2H), 0.35 ppm (m,2H);

using chloromethyl phenyl sulphide with sodium hydride in dimethylformamide there is obtained 3-[4-chloro-2-fluoro-5-[(phenylthio)methoxy]phenyl}-1 -methyl-6 -trifluoromethyl-2,4(1H,3H)-pyrimidinedione m.p. 91°–94° C.;

using chloromethyl cyclopentyl ether with sodium hydride in dimethylformamide there is obtained 3-{4-chloro-5-[(cyclopentyloxy)methoxy]-2 -fluorophenyl}-1-methyl-6-trifluoromethyl-2,4(1H,3H) -pyrimidinedione. $^1$-NMR (CDCl$_3$, 250 MHz) 7.30 ppm (d,1H), 7.13 ppm (d,1H), 6.36 ppm (s,1H), 5.27 ppm (s,2H), 4.33 ppm (m,1H), 3.55 ppm (d,3H), 1.41–1.88 ppm (m,8H);

using 2-bromomethyltetrahydropyran with sodium hydride in dimethylformamide there is obtained 3-{4-chloro-2-fluoro-5-[(tetrahydro-2H -pyran-2-yl)methoxy]phenyl}-1-methyl-6-trifluoromethyl)-2,4(1H,3H)-pyrimidinedione, $^1$-NMR (CDCl$_3$, 250 MHz): 7.29 ppm (d,1H), 6.83 ppm (d,1H), 6.36 ppm (s,1H), 3.40–4.10 ppm (m,5H), 3.55 ppm (d,3H), 1.28–2.00 ppm (m,6H);

using furan-2-carbonyl chloride with pyridine in methylenechloride there is obtained 2-chloro-5-[3,6-dihydro-2,6-dioxo-3-methyl-4-trifluoromethyl-1(2H)-pyrimidinyl]-4 -fluorophenyl 2-furoate, 3 $^1$H-NMR (CDCl$_3$, 250 MHz); 7.70 ppm (q,1H), 7.36–7.50 ppm (m,2H), 7.30 ppm (d,1H), 6.61 ppm (q,1H), 6.36 ppm (s,1H), 3.55 ppm (d,3H);

using 2-chloro-4,6-dimethoxy-s-triazine with sodium hydride in dimethylformamide there is obtained 3-[4-chloro-5-[(4,6-dimethoxy-s-triazin-2-yl)oxy]-2-fluoro-phenyl}-1-methyl-6 -trifluoromethyl-2,4(1H,3H)-pyrimidinedione, 1-NMR (CDCl3, 250 MHz): 7.40 ppm (d,1H), 7.20 ppm (d,1H), 6.36 ppm (s,1H), 3.99 ppm (s,6H), 3.56 ppm (d,3H);

using 2-chloropyrimidine with sodium hydride in dimethylformamide there is obtained 3-[4-chloro-2-fluoro-5 -(2-pyrimidinyloxy)-phenyl]-1-methyl-6 -trifluoromethyl-2,4(1H,3H)-pyrimidinedione m.p. 192°–194° C.;

using 2-chloro-3-nitropyridine with sodium hydride in formamide there is obtained 3-{4-chloro-2-fluoro-5-[(3-nitro-2-pyridyl)oxy]-phenyl}-1-methyl-6-trifluoromethyl-2,4(1H,3H)-pyrimidinedione, m.p. 177°–179° C.;

using epibromohydrin with sodium hydride in dimethylformamide there is obtained 3-[4-chloro-5-(2,3-epoxypropoxy)-2-fluorophenyl]-1 -methyl-6-trifluoromethyl-2,4(1H,3H)-pyrimidinedione, m.p. 93°–96° C.;

using chloromethyl trimethylsilane with sodium hydride in dimethylformamide there is obtained 3-{4-chloro-2-fluoro-5-[(trimethylsilyl)methoxy]-phenyl}-1-methyl--trifluoromethyl-2,4(1H,3H)-pyrimidinedione, m.p. 91°–93° C.;

using 5-chloromethyl-1-methyltetrazole with sodium -chloro-2-fluoro-5-[(1-methyl-1H-tetrazol-5-yl)methoxy]-phenyl}-1-methyl-6 -trifluoromethyl-2,4(1H,3H)-pyrimidinedione, m.p. 169°–171° C.;

using 2,2,2-trifluoroethyl methanesulphonate with sodium hydride in dimethylformamide there is obtained 3-[4-chloro-2-fluoro-5 -(2,2,2-trifluoroethoxy)-phenyl]-1-methyl-6 -trifluoromethyl-2,4(1H,3H)-pyrimidinedione, m.p. 136°–138° C.;

using 2-bromo-4-methylpentane with sodium hydride in dimethylformamide there is obtained 3-[4-chloro-5-(1H,3-dimethylbutoxy)-2-fluorophenyl]-1-methyl-6-trifluoromethyl- -2,4(1H,3H)-pyrimidinedione. m.p. 169°–171° C.;

using 1-iodohexane with sodium hydride in dimethylformamide there is obtained 3-[4-chloro-5-(n-hexyloxy)-2-fluorophenyl]-1-methyl-6 -trifluoromethyl-2,4(1H,3H)- -pyrimidinedione. m.p. 60°–63° C.;

using 1-iodo-2-methylpropane with sodium carbonate in acetonitrile there is obtained 3-(4-chloro-2-fluoro-5-iso-butoxyphenyl)-1-methyl-6 -trifluoromethyl-2,4(1H,3H)-pyrimidinedione, 1-NMR (CDCl3, 400 MHz); 7.30 ppm (d,1H). 6.76 ppm (d,1H). 6.36 ppm s,1H). 3.72 ppm (d,2H), 3.55 ppm (d,3H). 2.14 ppm (m,1H). 1.03 ppm (d,6H):

using 1-iodo-3-methylbutane with sodium hydride in dimethylformamide there is obtained 3-[4-chloro-2-fluoro-5-(1-isopentoxy)-phenyl]-1-methyl-6 -trifluoromethyl-2,4(1H,3H)-pyrimidinedione. 1H-NMR (CDCl3. 400 MHz): 7.30 ppm (d,1H). 6.77 ppm (d,1H). 6.37 ppm (s,1H). 3.99 ppm (t.2H). 3.56 ppm (d,3H). 1.86 ppm (m,1H). 1.72 ppm (q.2H). 0.96 ppm (d,6H):

using 1-iodo-pentane with sodium hydride in dimethylformamide there is obtained 3-(4-chloro-2-fluoro-5-pentoxy-phenyl)-1-methyl-6 -trifluoromethyl-2,4(1H,3H)-pyrimidinedione. m.p. 64°–66° C.;

using 2-bromo-pentane with sodium hydride in dimethylformamide there is obtained 3-[4-chloro-2-fluoro-5-(1-methylbutoxy)-phenyl]-1-methyl-6-trifluoromethyl-2,4(1H,3H)-pyrimidinedione, m.p. 94°–97° C.;

using 2-iodo-butane with sodium carbonate in acetonitrile there is obtained 3-[4-chloro-2-fluoro-5-(1-methylpropoxy)-phenyl]-1-methyl-6 -trifluoromethyl-2,4(1H,3H)-pyrimidinedione. 1H-NMR (CDCl3. 400 MHz): 7.29 ppm (d,1H). 6.78 ppm (d,1H). 6.36 ppm (s,1H). 4.22 ppm (sextet,1H). 3.56 ppm (d,3H), 1.60°–1.85 ppm (m.2H). 1.31 ppm (d,3H). 0.99 ppm t,3H):

using 1-iodo-octane with sodium hydride in dimethylformamide there is obtained 3-(4-chloro-2-fluoro-5-octyloxy-phenyl)-1-methyl-6 -trifluoromethyl-2,4(1H,3H)-pyrimidinedione, m.p. 60°–63° C.;

using 1-iodo-2,2-dimethylpropane with sodium hydride in dimethylformamide there is obtained 3-[4-chloro-5-(2,2-dimethylpropoxy)-2-fluorophenyl]-1 -methyl-6-trifluoromethyl-2,4(1H,3H)-pyrimidinedione, m.p. 122°–124° C.;

using 2-chloroethyl methanesulphonate with sodium hydride in dimethylformamide there is obtained 3-[4-chloro-5-(2-chloro-ethoxy)-2-fluorophenyl]-1-methyl-6-trifluoromethyl-2,4(1H,3H)-pyrimidinedione, m.p. 100°–103° C.;

using diethyl (mesyloxy)methanephosphonate and potassium carbonate in acetonitrile there is obtained diethyl {2-chloro-5-[3,6-dihydro-2,6-dioxo-3-methyl-4-trifluoromethyl-1(2H)-pyrimidinyl]-4-fluorophenoxy}methanephosphonate. m.p. 87°–88° C.;

using diethyl 1-(tosyloxy)ethanephosphonate and potassium carbonate in acetonitrile there is obtained diethyl 1-{2-chloro-5-[3,6-dihydro-2,6 -dioxo-3-methyl-4-trifluoromethyl-1(2H)-pyrimidinyl]-4 -fluorophenoxy}ethanephosphonate. 1H-NMR (CDCl3, 60 MHz): 7.36 ppm (d,1H). 7.31 ppm (d,1H). 6.40 ppm (s,1H). 3.90°–4.90 ppm (m.5H). 3.60 ppm s,3H). 1.10°–2.00 (m.9H):

using 2-[(isopropylideneamino)oxy]ethyl toluene-4-sulphonate and potassium carbonate in acetonitrile there is obrained 3-[4-chloro-2-fluoro-5-{2-[(isopropylideneamino)oxy]ethoxy}-phenyl]-1 -methyl-6-trifluoromethyl-2,4(1H,3H)-pyrimidinedione, m.p. 103° C.;

using N,N-diethyl-N -[(isopropylideneamino)oxy]-methyl-N-methyl-ammonium hydroxide in toluene there is 3-[4-chloro-2-fluoro-5{[(isopropylidenamino)-oxy]methoxy}-phenyl]-1-methyl-6 -trifluoromethyl-2,4(1H,3H)-pyrimidinedione, m.p. 118° C.;

using 3-(4-bromo-2-fluoro-5-hydroxyphenyl)-1-methyl-6-trifluoromethyl-2,4(1H,3H)-pyrimidinedione with potassium carbonate and methyl iodide in acetonitrile there is obtained 3-(4-bromo-2-fluoro-5-methoxy-phenyl)-1-methyl-6-trifluoromethyl-2,4(1H,3H)-pyrimidinedione. m.p. 154° C.;

using ethyl iodide and potassium carbonate in acetonitrile there is obtained 3-(5-ethoxy-4-bromo-2-fluorophenyl)-1-methyl-6-trifluoromethyl-2,4(1H,3H) -pyrimidinedione, m.p. 128° C.;

using propyl iodide und potassium carbonate in acetotrile there is obtained 3-(4-bromo-2-fluoro-5-propoxyphenyl)-1-methyl-6 -trifluoromethyl-2,4(1H,3H)-pyrimidinedione, m.p. 119° C.;

using butyl iodide and potassium carbonate in acetonitrile there is obtained 3-(4-bromo-5-butoxy-2-fluorophenyl)-1-methyl-6-trifluoromethyl-2,4(1H,3H) -pyrimidinedione, m.p. 73° C.;

using isobutyl iodide and potassium carbonate in acetonitrile there is obtained 3-(4-bromo-2-fluoro-5-isobutoxyphenyl)-1-methyl-6-trifluoromethyl-2,4(1H,3H)-pyrimidinedione, $^1$H-NMR (CDCl$_3$, 400 MHz): 7.55 ppm (d,1H). 6.79 ppm (d,1H). 6.43 ppm (s,1H). 3.76 ppm (d,2H), 3.58 ppm (d,3H), 2.17 ppm (m,1H), 1.05 ppm (d,6H);

using allyl bromide and potassium carbonate in acetonitrile there is obtained 3-(5-allyloxy-4-bromo-2-fluorophenyl)-1-methyl-6-trifluoromethyl-2,4(1H,3H)-pyrimidinedione, m.p. 120° C.;

using propargyl bromide and potassium carbonate in acetonitrile there is obtained 3-[4-bromo-2-fluoro-5 (2-propynyloxy)-phenyl]-1-methyl-6-trifluoromethyl-2,4(1H,3H)-pyrimidinedione. m.p. 134° C.;

using N,N-diethyl-N-[(isopropylideneamino)oxy]-methyl-N-methyl-ammonium hydroxide in toluene there is obtained 3-[4-bromo-2-fluoro-5-{[(isopropylideneamino)oxy]methoxy}-phenyl]-1-methyl-6-trifluoromethyl-2,4(1H,3H)-pyrimidinedione, m.p. 121° C.;

using chlorodimethyl ether and potassium carbonate in acetonitrile there is obtained 3-[4-bromo-2-fluoro-5-(methoxymethoxy)-phenyl]-1-methyl-6-trifluoromethyl-2,4(1H,3H)-pyrimidinedione, $^1$H-NMR (CDCl$_3$, 400 MHz): 7.46 ppm (d,1H), 7.08 ppm (d,1H), 6.35 ppm (s,1H). 5.22 ppm s,2H). 3.56 ppm (d,3H), 3.52 ppm (s,3H);

using 2-[(isopropylideneamino)oxy]-ethyl toluene-4-sulphonate and potassium carbonate in acetonitrile there is obtained 3-[4-bromo-2-fluoro-5-{2-[isopropylideneamino)oxy]ethoxy}-phenyl]-1-methyl-6-trifluoromethyl-2,4(1H,3H)-pyrimidinedione, m.p. 115° C.;

using 3-(4-chloro-2-fluoro-5-hydroxyphenyl)-1-methyl-6-trifluoromethyl-2,4(1H,3H)-pyrimidinedione with α-bromoacetophenone and sodium hydride in dimethylformamide there is obtained 3-[4-chloro-2-fluoro-5-(phenacyloxy)-phenyl]-1-methyl-6-trifluoromethyl-2,4(1H,3H)-pyrimidinedione, m.p. 152°–153° C.;

using 2-chloroacetamide and sodium hydride in dimethylformamide there is obtained 2-[2-chloro-5-[3,6-dihydro-2,6-dioxo-3-methyl-4-trifluoromethyl-1(2H)-pyrimidinyl]-4-fluorophenoxy}-acetamide, m.p. 203°–205° C.;

using 4-bromobutyronitrile and sodium hydride in dihydro-2,6-dioxo-3-methyl-4-trifluoromethyl-1(2H)-pyrimidinyl]-4-fluorophenoxy}-butyronitrile, m.p. 104°–106° C.:

using N-methyl-2-chloroacetamide and sodium hydride in dimethylformamide there is obtained 2-[2-chloro-5-[3,6-dihydro-2,6-dioxo-3-methyl-4-trifluoromethyl-1(2H)-pyrimidinyl]-4-fluorophenoxy]-N-methylacetamide, m.p. 190°–192° C.;

using 2-chloromethyl-4,6-dimethylpyrimidine and sodium hydride in dimethylformamide there is obtained 3-{4-chloro-5-[(4,6-dimethyl-2-pyrimidinyl)methoxy]-2-fluorophenyl}-1-methyl-6-trifluoromethyl-2,4(1H,3H)-pyrimidinedione, 1-NMR (CDCl$_3$, 400 MHz): 7.30 ppm (d,1H), 6.99 ppm (d,1H), 6.96 ppm s,1H). 6.33 ppm (s,1H), 5.24 ppm (q,2H), 3.54 ppm (d,3H). 2.48 ppm (s,6H);

using 4-ethoxy-2-chloromethyl-6-methylpyrimidine and sodium hydride in dimethylformamide there is obtained 3-{5-[(4-ethoxy-6-methyl-2-pyrimidinyl)methoxy]-4-chloro-2-fluorophenyl}-1-methyl-6-trifluoromethyl-2,4(1H,3H)-pyrimidinedione, 1-NMR (CDCl$_3$, 400 MHz): 7.31 ppm (d,1H), 6.92 ppm (d,1H), 6.44 ppm (d,1H). 6.33 ppm (s,1H). 5.20 ppm (q,2H), 4.31 ppm (q,2H), 3.54 ppm (d,3H). 2.42 ppm s,3H). 1.30 ppm (t.3H);

using 2-bromoethanol and sodium methylate in methanol there is obtained 3-[4-chloro-2-fluoro-5-(2-hydroxyethoxy)-phenyl]-1-methyl-6-trifluoromethyl-2,4(1H,3H)-pyrimidinedione, $^1$-NMR (CDCl$_3$, 60 MHz): 7.31 ppm (d,1H). 6.84 ppm (d,1H). 6.37 ppm (s,1H). 3.80°–4.25 ppm (m,4H). 3.56 ppm (d,3H). 2.53 ppm s,1H);

using 2-chloromethyl-4,7-dimethoxypyrimidine and sodium hydride in dimethylformamide there is obtained 3-{4-chloro-5-[(4,6-dimethoxy-2-pyrimidinyl)methoxy]-2-fluorophenyl}-1-methyl-6-trifluoromethyl-2,4(1H,3H)-pyrimidinedione, $^1$-NMR (CDCl$_3$, 400 MHz): 7.33 ppm (d,1H), 6.87 ppm (d,1H). 6.33 ppm s,1H). 5.93 ppm (s,1H). 5.17 ppm (q,2H), 3.86 ppm s,6H), 3.53 ppm (d,3H)

using 2-chlorodiethyl ether and sodium hydride in dimethylformamide there is obtained 3-[4-chloro-5-[2-(2-chloroethoxy)-ethoxy]-2-fluorophenyl]-1-methyl-6-trifluoromethyl-2,4(1H,3H)-pyrimidinedione, $^1$H-NMR (CDCl$_3$, 400 MHz): 7.31 ppm (d,1H), 6.92 ppm (d,1H). 6.36 ppm (s,1H). 4.18 ppm (m,2H). 3.90 ppm (m,2H), 3.85 ppm (m,2H), 3.65 ppm (m,2H), 3.55 ppm (d,3H);

using 5-chloro-1H,3-dimethyl-4-nitropyrazole and sodium hydride in dimethylformamide there is obtained 3-{4-chloro-5-[(1H,3-dimethyl-4-nitropyrazol-5-yl)oxy]-2-fluorophenyl}-1-methyl-6-trifluoromethyl-2,4(1H,3H)-pyrimidinedione, m.p. 191°–193° C.;

using chloroacetonitrile and sodium hydride in dimethylformamide there is obained {2-chloro-5-[3,6-dihydro-2,6-dioxo-3-methyl-4-trifluoromethyl-1(2H)-pyrimidinyl]-4-fluorophenoxy}-acetonitrile. m.p. 158°–159° C.;

using N-chloroacetylpiperidine and sodium hydride in dimethylformamide there is obtained N-[{2-chloro-5-[3,6-dihydro-2,6-dioxo-3-methyl-4-trifluoromethyl-1(2H)-pyrimidinyl]-4-fluorophenoxy}acetyl]-piperidine, $^1$H-NMR (CDCl$_3$, 400 MHz): 7.32 ppm (d,1H), 6.98 ppm (d,1H), 6.35 ppm s,1H), 4.72 ppm (s,2H), 3.48°–3.58 ppm (m,7H), 1.46°–1.70 ppm (m,6H);

using allyl chloromethyl sulphide and sodium hydride in dimethylformamide there is obtained 3-{5-[(allylthio)methoxy]-4-chloro-2-fluorophenyl}-1-methyl-6-trifluoromethyl-2,4(1H,3H)-pyrimidinedione, $^1$H-NMR (CDCl$_3$, 400 MHz): 7.32 ppm (d,1H), 6.93 ppm (d,1H), 6.36 ppm (s,1H), 5.73°–5.85 ppm (m,1H), 5.13°–5.24 ppm (m,4H), 3 55 ppm (d,3H), 3.29 ppm (m,2H):

using chloromethyl cyclohexyl sulphide and sodium ride in dimethylformamide there is obtained 3-{4-chloro-5-[(cyclohexylthio)methoxy]-2-fluorophenyl}-1-methyl-6-trifluoromethyl-2,4(1H,3H)-pyrimidinedione, $^1$H-NMR (CDCl$_3$, 400 MHz)! 7.32 ppm (d,1H) 6.90 ppm (d,1H), 6 36 ppm s,1H), 5.24 ppm (t,2H), 3.56 ppm (d,3H), 2.89°–2.99 ppm (m,1H), 1 99°–2.08 ppm (m,2H), 1.71°–1.81 ppm (m,2H), 1.56°–1.66 ppm (m,1H), 1.18°–1.47 ppm (m,5H):

using 3-[4-chloro-2-fluoro-5-(2-hydroxyethoxy)-phenyl]-1-methyl-6-trifluoromethyl-2,4(1H,3H)-pyrimidinedione and acetyl chloride with pyridine in diethyl ether there is obtained 2-{2-chloro-5-[3,6-dihydro-2,6-dioxo-3-methyl-4-trifluoromethyl-1(2H)-pyrimidinyl]-4-fluorophenoxy}-ethyl acetate, m.p. 88°–90° C.;

using 3-[4-chloro-2-fluoro-5-(2-hydroxyethoxy)-phenyl]-1-methyl-6-trifluoromethyl-2,4(1H,3H)- pyrimidinedione and chloroacetyl chloride with pyridine in diethyl ether there is obtained 2-{2-chloro-5-[3,6-dihydro-2,6-dioxo-3-methyl-4 -trifluoromethyl-1(2H)-pyrimidinyl]-4 -fluorophenoxy}-ethylchloroacetate, m.p. 96°–99° C.;

using 3-[4-chloro-2-fluoro-5-(2-hydroxyethoxy)-phenyl]-1-methyl-6 -trifluoromethyl-2,4(1H,3H)-pyrimidinedione and ethyl chloroformate with pyridine in diethyl ether there is obtained 2-[2-chloro-5-(3,6-dihydro-2,6-dioxo-3-methyl-4-trifluoromethyl-1(2H)-pyrimidinyl]-4-fluorophenoxy]-ethyl ethyl carbonate, $^1$H-NMR (CDCl$_3$, 400 MHz): 7.32 ppm (d,1H), 6.81 ppm (d,1H), 6.36 ppm (s,1H), 4.47°–4.54 ppm (m,2H), 4.16°–4.27 ppm (m,4H), 3.56 ppm (d,3H), 1.32 ppm (t,3H);

using 3-(4-chloro-2-fluoro-5-hydroxyphenyl)-1-methyl-6-trifluoromethyl-2,4(1H,3H)-pyrimidinedione with N-chlorocarbonyl-piperidine and sodium hydride in dimethylformamide there is obtained {2-chloro-5-[3,6-dihydro-2,6-dioxo-3-methyl-4-trifluoromethyl-1(2H) -pyrimidinyl]-4-fluorophenyl}-1-piperidinecarboxylate, $^1$-NMR (CDCl$_3$, 400 MHz): 7.33 ppm (d,1H), 7.25 ppm (d,1H), 6.34 ppm (s,1H), 3.57°–3.69 ppm (m,2H), 3.53 ppm (d,3H), 3.44°–3.56 ppm (m,2H), 1.56°–1.70 ppm (m,6H);

using 3-[4-chloro-2-fluoro-5-(2-hydroxyethoxy)-phenyl]-1-methyl-6 -trifluoromethyl-2,4(1H,3H)-pyrimidinedione with N-chlorocarbonyl-piperidine and triethylamine in toluene there is obtained 2-{2-chloro-5-[3,6-dihydro-2,6-dioxo-3-methyl-4 -trifluoromethyl-1(2H)-pyrimidinyl]-4 -fluorophenoxy}-ethyl]-1-piperidinecarboxylate, $^1$H-NMR (CDCl$_3$, 400 MHz): 7.32 ppm (d,$^1$H), 6.82 ppm (d,1H), 6.37 ppm (s,1H), 4.44 ppm (m,2H), 4.19 ppm (m,2H), 3.56 ppm (d,3H), 3.36°–3.46 ppm (m,4H), 1.45°–1.63 ppm (m,6H):

using 3-(4-chloro-2-fluoro-5-hydroxyphenyl)-1-methyl-6-trifluoromethyl-2,4(1H,3H)-pyrimidinedione with phenylacetyl chloride and pyridine in diethyl ether there is obtained {2-chloro-5-[3,6-dihydro-2,6-dioxo-3-methyl-4-trifluoromethyl-1(2H)-pyrimidinyl]-4 -fluorophenyl}-phenyl acetate, $^1$H-NMR (CDCl$_3$, 400 MHz): 7.27–7.40 ppm (m,6H), 7.10 ppm (d,1H), 6.33 ppm (s,1H), 3.89 ppm (s,2H), 3.53 ppm (d,3H);

using phenylmethane sulphochloride and triethylamine in diethyl ether there is obtained 2-chloro-5-[3,6-dihydro-2,6-dioxo-3-methyl-4-trifluoromethyl-1(2H) -pyrimidinyl]-4-fluorophenyl phenylmethansulphonate, $^1$H-NMR (CDCl$_3$, 400 MHz): 7.37°–7.50 ppm m,5H), 7.37 ppm (d,1H), 7.23 ppm (d,1H), 6.34 ppm (s,1H), 4.61 ppm (s,2H), 3.54 ppm (d,3H):

using cyclohexylacetyl chloride and pyridine in diethyl ether there is obtained 2-chloro-5-[3,6-dihydro-2,6-dioxo-3-methyl-4-trifluoromethyl-1(2H) -pyrimidinyl]-4-fluorophenyl cyclohexylacetate, $^1$H-NMR (CDCl$_3$, 400 MHz): 7.36 ppm (d,1H), 7.13 ppm (d,1H), 6.35 ppm (s,1H), 3.55 ppm (d,3H), 2.47 ppm (d,2H), 1.60°–2.00 ppm (m,6H), 0.99°–1.37 ppm (m,5H);

using nicotinoyl chloride hydrochloride and pyridine in diethyl ether there is obtained 2-chloro-5-[3,6-dihydro-2,6-dioxo-3-methyl-4-trifluoromethyl-1(2H) -pyrimidinyl]-4-fluorophenyl 3-pyridinecarboxylate, $^1$-NMR (CDCl$_3$, 400 MHz): 9.41 ppm (s,1H), 8.89 ppm (d,1H), 8.46 ppm (d,1H), 7.50 ppm (q,1H), 7.44 ppm (d,1H), 7.35 ppm (d,1H), 6.37 ppm (s,1H), 3.57 ppm (d,3H):

using 2-phenylethyl bromide and sodium carbonate in dimethylformamide there is obtained 3-[4-chloro-2-fluoro-5-(2-phenylethoxy)-phenyl]-1-methyl-6 -trifluoromethyl-2,4(1H,3H)-pyrimidinedione, $^1$H-NMR (CDCl$_3$, 400 MHz): 7.20°–7.34 ppm (m,6H), 6.74 ppm (d,1H), 6.34 ppm (s,1H), 4.15 ppm (t,2H), 3.54 ppm (d,3H), 3.14 ppm (t,2H);

using 2-thienylacetyl chloride and pyridine in methylene chloride there is obtained 2-chloro-5-[3,6-dihydro-2,6-dioxo-3-methyl-4 -trifluoromethyl-1(2H)-pyrimidinyl]-4-fluorophenyl 2-thienylacetate, 1-NMR (CDCl$_3$, 400 MHz): 7.36 ppm (d,1H), 7.26 ppm (q,1H), 7.15 ppm (d,1H), 7.03°–7.07 ppm (m,1H), 6.99 ppm (q,1H), 6.34 ppm (s,1H), 4.12 ppm (d,2H), 3.54 ppm (d,3H):

using 3-[4-chloro-2-fluoro-5-(2-hydroxyethoxy)-phenyl]-1-methyl-6 -trifluoromethyl-2,4(1H,3H)-pyrimidinedione with N,N-dimethylcarbamoyl chloride and triethylamine in toluene there is obtained 2-[2-chloro-5-[3,6-dihydro-2,6 -dioxo-3-methyl-4-trifluoromethyl-1(2H)-pyrimidinyl]-4 -fluorophenoxy]-ethyl N,N-dimethylcarbamate, $^1$H-NMR (CDCl$_3$, 400 MHz): 7.31 ppm (d,1H), 6.81 ppm (d,1H), 6.36 ppm (s,1H), 4.40°–4.47 ppm (m,2H), 4.16°–4.22 ppm (m,2H), 3.56 ppm (d,3H), 2.92 ppm (s,3H), 2.89 ppm (s,3H);

using 3-(4-chloro-2-fluoro-5-hydroxyphenyl)-1-methyl-6-trifluoromethyl-2,4(1H,3H)-pyrimidinedione with 3-phenylpropyl bromide and sodium carbonate in dimethylformamide there is obtained 3-[4-chloro-2-fluoro-5-(3-phenylpropoxy)-phenyl]-1-methyl-6 -trifluoromethyl-2,4(1H,3H)-pyrimidinedione, $^1$H-NMR (CDCl$_3$, 400 MHZ): 7.15°–7.34 ppm (m,6H), 6.71 ppm (d,1H), 6.36 ppm (s,1H), 3.96 ppm (t,2H), 3.55 ppm (d,3H), 2.83 ppm (t,2H), 2.10°–2.20 ppm (m,2H):

using 1-chlorosulphonylpiperidine with sodium hydride in dimethylformamide there is obtained 2-chloro-5-[3,6-dihydro-2,6-dioxo-3-methyl-4 -trifluoromethyl-1(2H)-pyrimidinyl]-4-fluorophenyl 1-piperidinesulphonate, $^1$H-NMR (CDCl$_3$, 400 MHz): 7.51 ppm (d,1H), 7.37 ppm (d,1H), 6.35 ppm (s,1H), 3.55 ppm (d,3H), 3.40°–3.48 ppm (m,4H), 1.52°–1.72 ppm (m,6H);

using N-ethyl-N-cyclohexylsulphamoyl chloride and sodium hydride in dimethylformamide there is obtained 2-chloro-5-[3,6-dihydro-2,6 -dioxo-3-methyl-4-trifluoromethyl-1(2H)-pyrimidinyl]-4 -fluorophenyl N-ethyl-N-cyclohexylsulphamate, 1-NMR (CDCl$_3$, 400 MHz): 7.52 ppm (d,1H), 6.36 ppm (s,1H), 3.71°–3.81 ppm (m,1H), 3.56 ppm (d,3H), 3.40 ppm (q,2H), 1.94°–2.04 ppm (m,2H), 1.79°–1.89 ppm (m,2H), 1.61°–1.71 ppm (m,1H), 1.43°–1.55 ppm (m,2H), 1.28°–1.41 ppm m,2H), 1.29 ppm (t,3H), 1.03°–1.16 ppm (m,1H);

using 3-chlorocarbonyl-1-methylpiperidine hydrochloride and sodium hydride in dimethylformamide there is obtained 2-chloro-5-[3,6-dihydro-2,6 -dioxo-3-methyl-4-trifluoromethyl-1(2H)-pyrimidinyl]-4 -fluorophenyl 1-methyl-3-piperidinecarboxylate, $^1$H-NMR (CDCl$_3$, 400 MHz): 7.36 ppm (d,1H), 7.15 ppm (d,1H), 6.35 ppm (s,1H), 3.55 ppm (d,3H), 3.05°–3.13 ppm (m,1H), 2.86°–2.96 ppm (m,1H), 2.71°–2.80 ppm (m,1H), 2.24°–2.36 ppm (m,4H), 1.98°–2.15 ppm (m,2H), 1.76°–1.86 ppm (m,1H), 1.51°–1.74 ppm (m,2H);

using ethyl bromoacetate and sodium hydride in dimethylformamide there is obtained ethyl {2-chloro-5-[3,6-dihydro-2,6-dioxo-3-methyl-4 -trifluoromethyl-1(2H)-pyrimidinyl]-4-fluorophenoxy}acetate, m.p. 98°–101° C.;

using chloroacetyl chloride and sodium hydride in dimethylformamide there is obtained 2-chloro-5-[3,6-dihydro-2,6-dioxo-3-methyl-4 -trifluoromethyl-1(2H)- pyrimidinyl]-4-fluorophenyl chloroacetate, m.p. 89°–92° C.;

using cyanoacetyl chloride in benzene there is obtained 2-chloro-5-[3,6-dihydro-2,6-dioxo-3-methyl-4-trifluoromethyl-1(2H)-pyrimidinyl]-4-fluorophenyl cyanoacetate, m.p. 157°–160° C.;

using 4-chloro-2-oxo-1,3-dioxolane and sodiumhydride in dimethylformamide there is obtained 3-{4-chloro-2-fluoro-5-[(2-oxo-1,3-dioxolan-4-yl)oxy]-phenyl}-1-methyl-6-trifluoromethyl-2,4(1H,3H)-pyrimidinedione, m.p. 165°–167° C.;

using 4-chloromethyl-3,5-dimethylisoxazole and sodium hydride in dimethylformamide there is obtained 3-{4-chloro-5-[(3,5-dimethyl-4-isoxazolyl)methoxy]-2-fluorophenyl}-1-methyl-6-trifluoromethyl-2,4(1H,3H)-pyrimidinedione, m.p. 120°–123° C.;

using 2-bromomethylthiophene and sodium hydride in dimethylformamide there is obtained 3-{4-chloro-2-fluoro-5-[(2-thienyl)methoxy]phenyl}-1-methyl-6-trifluoromethyl-2,4(1H,3H)-pyrimidinedione, m.p. 156°–158° C.;

using 4-chloromethyl-2,6-diethoxypyrimidine and sodium hydride in dimethylformamide there is obtained 3-{4-chloro-5-[(2,6-diethoxy-4-pyrimidinyl)methoxy]-2-fluorophenyl}-1-methyl-6-trifluoromethyl-2,4(1H,3H)-pyrimidinedione, 1-NMR (CDCl$_3$, 400 MHz): 7.36 ppm (d,1H), 6.81 ppm (d,1H), 6.66 ppm (s,1H), 6.36 ppm (s,1H), 4.99 ppm (d,2H), 4.42 ppm (q,2H), 4.38 ppm (q,2H), 3.55 ppm (d,3H), 1.41 ppm (t,3H), 1.40 ppm (t,3H);

using 2-bromomethylfuran and sodium hydride in dimethylformamide there is obtained 3-[4-chloro-2-fluoro-5-(2-furfuryl)-phenyl]-1-methyl-6-trifluoromethyl-2,4(1H,3H)-pyrimidinedione, m.p. 145°–147° C.;

using 4-chloromethyl-2-methylthiazole hydrochloride and sodium hydride in dimethylformamide there is obtained 3-{4-chloro-2-fluoro-5-[(2-methyl-4-thiazolyl)methoxy]-phenyl}-1-methyl-6-trifluoromethyl-2,4(1H,3H)-pyrimidinedione, m.p. 145°–147° C.;

using 2-bromom-γ-butyrolactone and sodium hydride in dimethylformamide is obtained 3-{4-chloro-2-fluoro-5-[(tetrahydro-2-oxo-3-furyl)oxy]-phenyl}-1-methyl-6-trifluoromethyl-2,4(1H,3H)-pyrimidinedione, m.p. 174°–176° C., using 3-(4-chloro-2-fluoro-5-hydroxyphenyl)-1-methyl-6-trifluoromethyl-2,4(1H,3H)-pyrimidinedione with diallylcarbamoyl chloride and sodium hydride in dimethylformamide there is obtained 2-chloro-5-[3,6-dihydro-2,6-dioxo-3-methyl-4-trifluoromethyl-1(2H)-pyrimidinyl]-4-fluorophenyl-N,N-diallylcarbamate, H-NMR (CDCl$_3$, 400 MHz): 7.34 ppm (d,1H), 7.27 ppm (d,1H), 6.34 ppm (s,1H), 5.75°–5.94 ppm (m,2H), 5.17°–5.27 ppm (m,4H), 4.04 ppm (d,2H), 3.96 ppm (d,2H), 3.54 ppm (d,3H);

using o-methylbenzyl chloride and sodium hydride in dimethylformamide there is obtained 3-{4-chloro-2-fluoro-5-[(o-methylbenzyl)oxy]-phenyl}-1-methyl-6-trifluoromethyl-2,4(1H,3H)-pyrimidinedione, $^1$H-NMR (CDCl$_3$, 400 MHz): 7.40°–7.45 ppm (m,1H), 7.33 ppm (d,1H), 7.19°–7.30 ppm (m,3H), 6.90 ppm (d,1H), 6.37 ppm s,1H), 5.03 ppm s,2H), 3.56 ppm (d,3H), 2.37 ppm (s,3H);

using monomethyl succinate chloride and pyridine in methylene chloride there is obtained 2-chloro-5-[3,6-dihydro-2,6-dioxo-3-methyl-4-trifluoromethyl-1(2H)pyrimidinyl]-4-fluorophenyl methylsuccinate, $^1$H-NMR (CDCl$_3$, 400 MHz): 7,36 ppm (d,1H), 7.17 ppm (d,1H), 6.35 ppm (s,1H), 3.72 ppm (s,3H), 3.55 ppm (d,3H), 2.94 ppm (q,2H), 2.76 ppm (q,2H);

using p-tert.butylbenzyl bromide and sodium hydride in dimethylformamide there is obtained 3-{5-[(p-tert.butylbenzyl)oxy]-4-chloro-2-fluorophenyl}-1-methyl-6-trifluoromethyl-2,4(1H,3H)-pyrimidinedione, m.p. 156°–158° C.;

using 2-(2-bromoethyl)-1,3-dioxolane and sodium hydride in dimethylformamide there is obtained 3-{4-chloro-5-[2-(1,3-dioxolan-2-yl)-ethoxy]-2-fluorophenyl}-1-methyl-6-trifluoromethyl-2,4(1H.3H)-pyrimidinedione. m.p. 125°–127° C.;

using 2-(2-bromoethyl)-1,3-dioxan and sodium hydride in dimethylformamide there is obtained 3-{4-chloro-5-[2-(1.3-dioxan-2-yl)-ethoxy]-2-fluorophenyl}-1-methyl-6-trifluoromethyl-2,4(1H,3H)-pyrimidinedione, m.p. 128°–130° C.;

using o-fluorobenzyl chloride and sodium hydride in dimethylformamide there is obtained 3-{4-chloro-5-[(o-fluorobenzyl)oxy]-2-fluorophenyl}-1-methyl-6-trifluoromethyl-2,4(1H,3H)-pyrimidinedione, m.p. 126°–128° C.;

using 2.6-dichlorobenzyl bromide and sodium hydride in dimethylformamide there is obtained 3-{4-chloro-5-[(2,6-dichlorbenzyl)oxy]-2-fluorophenyl}-1-methyl-6-trifluoromethyl-2,4(1H,3H)-pyrimidinedione, $^1$H-NMR (CDCl$_3$ 400 MHz): 7.23–7.40 ppm (m,4H). 7.01 ppm (d.1H), 6.38 ppm (s.1H), 5.29 ppm (s,2H). 3.58 ppm (d.3H);

using 2,3,4,5,6-pentafluorobenzyl bromide and sodium hydride in dimethylformamide there is obtained 3-{4-chloro-2-fluoro-5-[(2,3,4,5,6-pentafluorobenzyl)oxy]phenyl}-1-methyl-6-trifluoromethyl-2,4(1H,3H)-pyrimidinedione, $^1$H-NMR (CDCl$_3$ 400 MHz): 7.33 ppm (d.1H). 6.94 ppm (d.1H), 6.38 ppm (s.1H), 5.14 ppm (t,2H), 3.57 ppm (d,3H):

using 3,4-dichlorbenzyl chloride and sodium hydride in dimethylformamide there is obtained 3-{4-chloro-5-[(3,4-dichlorobenzyl)oxy]-2-fluorophenyl}-1-methyl-6-trifluoromethyl-2,4(1H,3H)-pyrimidinedione. m.p.

using o-chlorobenzyl chloride and sodium hydride in dimethylformamide there is obtained 3-{4-chloro-5-[(o-chlorobenzyl)oxy]-2-fluorophenyl}-1-methyl-6-trifluoromethyl-2,4(1H,3H)-pyrimidinedione. m.p. 126°–129° C.;

using p-nitrobenzyl bromide and sodium hydride in dimethylformamide there is obtained 3-{4-chloro-2-fluoromethylformamide-5-[(4-nitrobenzyl)oxy]phenyl}-1-methyl-6-trifluoromethyl-2,4(1H,3H)-pyrimidinedione, m.p. 147°–149° C.;

using 2,4-dichlorbenzyl chloride and sodium hydride in dimethylformamide there is obtained 3-[4-chloro-5-[(2,4-dichlorobenzyl)oxy]-2-fluorophenyl]-1-methyl-6-trifluoromethyl-2,4(1H,3H)-pyrimidinedione. m.p. 112°–120° C.;

using m-fluorobenzyl chloride and sodium hydride in dimethylformamide there is obtained 3-{4-chloro-5-[(m-fluorobenzyl)oxy]-2-fluorophenyl}-1-methyl-6-trifluoromethyl-2,4(1H,3H)-pyrimidinedione. m.p. 135°–137° C.;

using p-fluorobenzyl chloride and sodium hydride in dimethylformamide there is obtained 3-{4-chloro-5-[(p-fluorobenzyl)oxy]-2-fluorophenyl}-1-methyl-6-trifluoromethyl-2,4(1H,3H)-pyrimidinedione, m.p. 174°–177° C.;

using p-trifluoromethyl-benzyl bromide and sodium in dimethylformamide there is obtained 3-[4-chloro-2-fluoro-5-(p-trifluoromethyl-benzyloxy)-phenyl]-1- methyl-6-trifluoromethyl-2,4 1H,3H)-pyrimidinedione, m.p. 158°-159° C.;

using 1-bromo-2-[2-(2-methoxyethoxy)-ethoxy]-ethane and sodium hydride in dimethylformamide there is obtained 3-[4-chloro-2-fluoro-5-{2-[2-(2 -methoxyethoxy)-ethoxy]-ethoxy}-phenyl]-1-methy -2.4(1H.3H)-pyrimidinedione. $^1$H-NMR (CDCl$_3$, 400 MHz): 7.30 ppm d.1H), 6.84 ppm (d.1H), 6.36 ppm (s.1H). 4.12–4.17 ppm (m,2H), 3.85–3.90 ppm (m,2H), 3.73–3.78 ppm (m,2H), 3.62–3.69 ppm (m,4H), 3.52–3.58 ppm (m,5H), 3.37 ppm (s,3H):

using 1-bromo-2-isopropoxyethane and sodium hydride in dimethylformamide there is obtained 3-{4-chloro-2-fluoro-5-[2-(isopropoxy)-ethoxy]-phenyl}-1-methyl-6-trifluoromethyl-2,4(1H,3H)-pyrimidinedione, $^1$H-NMR (CDCl$_3$. 400 MHz): 7.30 ppm (d,1H), 6.86 ppm (d.1H), 6.36 ppm (s,1H), 4.12 ppm (t,2H), 3.80 ppm (m,2H), 3.71 ppm (m,1H), 3.56 ppm (d,3H), 1.18 ppm (d,6H):

2-bromo-1-methoxypropane and sodium hydride in using delformamide there is obtained 3-[4-chloro-2-fluoro -5-(2-methoxy-1-methylethoxy)-phenyl]-1 -methyl-6-trifluoromethyl-2,4(1H,3H)-pyrimidinedione, m.p. 80°-82° C.;

using merhoxyacetyl chloride and pyridine in methylene chloride there is obtained 2-chloro-5-[3,6-dihydro-2,6-dioxo-3-methyl-4 -trifluoromethyl-1(2H)-pyrimidinyl]-4-fluorophenyl methoxyacetate, m.p. 101°-103° C.

EXAMPLE 9

A solution of 0.68 g of propiolic acid in 5 ml of methylene chloride is added dropwise at 0° C. while stirring during 5 minutes to a solution of 2.18 g of N,N'-dicyclohexylcarbodiimide in 10 ml of methylene chloride and the mixture is stirred at 0° C. for 15 minutes. solution of 1.5 g of 3-(4-chloro-2-fluoro-5-hydroxyphenyl)-1-methyl-6 -trifluoromethyl-2,4(1H,3H)-pyrimidinedione in 10 ml of methylene chloride is added dropwise while stirring during 20 minutes and the mixture is stirred at 0° C. for 2 hours. Insoluble constituents are filtered off under suction and the filtrate is evaporated to dryness under reduced pressure. The residue is purified by chromatography on a silica gel column using ethyl acetate/n-hexane (1:7) as the eluent. There is obtained 2-chloro-5-[3,6-dihydro-2,6-dioxo-3-methyl -4-trifluoromethyl-1(2H)-pyrimidinyl]-4-fluorophenyl propiolate. $^1$H-NMR (CDCl$_3$. 400 MHz: 7.40 ppm (d,1H), 7.21 ppm 1(d,1H), 6.36 ppm (s,1H), 3.56 ppm (d,3H). 3.15 ppm (s,1H), In an analogous manner:

using 3-(4-chloro-2-fluoro-5-hydroxyphenyl)-1-methyl-6-trifluoromethyl-2,4(1H,3H)-pyrimidinedione and 3-[piperidino(carbonyl)]-propionic acid with N,N'-dicyclohexylcarbodiimide and 4-dimethylaminopyridine as the catalyst in methylene chloride there is obtained 2-chloro-5-[3,6-dihydro-2,6-dioxo-3-methyl-4-trifluoromethyl-1(2H)-pyrimidinyl]-4 -fluorophenyl 3-[piperidino(carbonyl)]propionate. $^1$H-NMR (CDC$_3$, 400 MHz): 7.35 ppm (d,1H), 7.20 ppm (d,1H), 6.36 ppm (s,1H), 3.50–3.60 ppm (m,5H), 3.42 ppm (t,2H). 2.94 ppm (t,2H), 2.74 ppm (t,2H), 1.49°–1.70 ppm (m.6H);

using 3-(4-chloro-2-fluoro-5-hydroxyphenyl)-1-methyl-6-trifluoromethyl-2,4(1H,3H)-pyrimidinedione and dithiopropionic acid with N,N'-dicyclohexylcarbodiimide and 4-dimethylaminopyridine as the catalyst in methylene chloride there is obtained 3-[4-chloro-2-fluoro-5-(thio-propionyloxy)-phenyl]-1-methyl-6 -trifluoromethyl-$^1$H-NMR-2,4(1H,3H)-pyrimidinedione, $^1$-NHR (CDCl$_3$, 400 MHz): -2,4($^1$H,3H)-pyrimidinedione, 7.39 ppm (d,1H), 7.05 ppm (d,1H), 6.36 ppm (s,1H), 3.56 ppm (d.3H), 2.95 ppm (q,2H), 1.4 ppm (t,3H);

using 3-(4-chloro-2-fluoro-5-hydroxyphenyl)-1-methyl-6-trifluoromethyl-2,4(1H,3H)-pyrimidinedione and mono (2-chloroethyl) succinate with N,N'-dicyclohexylcarbodiimide and 4-dimethylaminopyridine as the catalyst in methylene chloride there is obtained 2-chloro-5-[3,6-dihydro-2,6-dioxo-3-methyl-4-trifluoromethyl-1(2H) -pyrimidinyl]-4-fluorophenyl 2-chloroethyl succinate. m.p. 94°-96° C.;

using 3-(4-chloro-2-fluoro-5-hydroxyphenyl)-1-methyl-6-trifluoromethyl-2,4(1H,3H)-pyrimidinedione and 3-(diethylcarbamoyl)-propionic acid with N,N'-dicyclohexylcarbodiimide and 4-pyrrolidino-pyridine as the catalyst in methylene chloride there is obtained 2-chloro-5-[3,6-dihydro-2,6-dioxo-3-methyl-4-trifluoromethyl-1(2H)-pyrimidinyl]-4-fluorophenyl 3-(diethylcarbamoyl)propionate, m.p. 91°-93° C.

EXAMPLE 10

0.51 g of methyl isocyanate and subsequently one drop of triethylamine are added at room temperature while stirring to a solution of 2.00 g of 3-(4-chloro-2-fluoro-5-hydroxyphenyl)-1-methyl-6-trifluoromethyl-2,4(1H,3H)-pyrimidinedione in 20 ml of methylene chloride. The reaction mixture is stirred for one hour and evaporated to dryness under reduced pressure. The residue is purified by chromatography on a silica gel column using diethyl ether-n-hexane (2:1) as the eluent. There is obtained 2-chloro-5-[3,6-dihydro-2,6-dioxo-3-methyl-4-trifluoromethyl-1(2H)-pyrimidinyl]-4-fluorophenyl methylcarbamate, $^1$H-NMR (CDCl$_3$, 400 MHz): 7.33 ppm (d,1H), 7.24 ppm (d,1H), 6.34 ppm (s,1H), 5.21 ppm (q,1H), 3.54 ppm (d,3H), 2.88 ppm (d,3H).

In an analogous manner:

using isopropyl isocyanate with triethylamine in methylene chloride there is obtained 2-chloro-5-[3,6-dihydro-2,6-dioxo-3-methyl-4-trifluoromethyl-1(2H) -pyrimidinyl]-4-fluorophenyl isopropylcarbamate. $^1$H-NMR (CDCl$_3$, 400 MHz): 7 33 ppm (d,1H), 7.25 ppm (d,1H), 6.35 ppm (s,1H), 5.04 ppm (d,1H), 3.88 ppm (m,1H), 3.54 ppm (d,3H), 1.23 ppm (d,6H);

using tert.butyl isocyanate with triethylamine in methylene chloride there is obtained 2-chloro-5-[3,6-dihydro-2,6-dioxo-3-methyl-4-trifluoromethyl-1(2H) -pyrimidinyl]-4-fluorophenyl tert.butylcarbamate, $^1$H-NMR (CDCl$_3$, 400 MHz): 7.33 ppm (d,1H), 7.25 ppm (d,1H), 6.34 ppm (s,1H). 5.16 ppm (s,1H), 3.44 ppm (d,3H), 1.38 ppm (s,9H);

using cyclohexyl isocyanate with triethylamine in methylene chloride there is obtained 2-chloro-5-[3,6-dihydro-2,6-dioxo-3-methyl-4-trifluoromethyl-1(2H) -pyrimidinyl]-4-fluorophenyl cyclohexylcarbamate, m.p. 171°-173° C.;

using allyl isocyanate with triethylamine in methylene chloride there is obtained 2-chloro-5-[3,6-dihydro -2,6-dioxo-3-methyl-4-trifluoromethyl-1(2H)-pyrimidinyl]-4-fluorophenyl allylcarbamate, m.p. 98°-100° C.;

using 3-trifluoromethylphenyl isocyanate with triethylamine in methylene chloride there is obtained 2-chloro-5-[3,6-dihydro-2,6-dioxo-3-methyl-4-trifluoromethyl-1(2H)-pyrimidinyl]-4 -fluorophenyl 3-trifluoromethylphenylcarbamate, m.p. 153°-155° C.;

using propargyl isocyanate with triethylamine in methylene chloride there is obtained 2-chloro-4-fluoro-5-[3,6-dihydro-2,6 -dioxo-3-methyl-4-trifluoromethyl-1(2H) -pyrimidinyl]phenyl 2-propynylcarbamate, m.p. 144°–146° C.;

using 3-[4-chloro-2-fluoro-5-(2-hydroxyethoxy -phenyl]-1-methyl-6 -trifluoromethyl-2,4(1H,3H)-pyrimidinedione and methyl isocyanate with pyridine in diethyl ether there is obtained 2-[2-chloro-5-(3,6-dihydro-2,6-dioxo-3-methyl-4 -trifluoromethyl-1(2H)-pyrimidinyl]-4-fluorophenoxy]-ethyl methylcarbamate, m.p. 173°–175° C.;

using 3-(4-chloro-2-fluoro-5-hydroxyphenyl)-1-methyl-6-trifluoromethyl-2,4(1H,3H)-pyrimidinedione with cyclohexylmethyl isocyanate and triethylamine in methylene chloride there is obtained 2-chloro-5-[3,6-dihydro-2,6-dioxo-3-methyl-4-trifluoromethyl-1(2H) -pyrimidinyl]-4-fluorophenyl cyclohexylmethylcarbamate, m.p. 132°–135° C.;

using benzyl isocyanate and triethylamine in diethyl ether there is obtained 2-chloro-5-[3,6-dihydro-2,6-dioxo-3-methyl-2-trifluoromethyl-1(2H) -pyrimidinyl]-4-fluorophenyl benzylcarbamate, m.p. 147°–150° C.

EXAMPLE 11

Analogously to Example 1, ethyl 3-amino-2-chlorocrotonate and 4-chloro-2-fluoro-5-isopropoxyphenyl isocyanate can be converted into 5-chloro-3-(4-chloro-2-fluoro-5-isopropoxyphenyl)-6-methyl-2,4(1H,3H) -pyrimidinedione.

By alkylation analogously to Example 6, from the above product with sodium hydride and dimethyl sulphate in dimethylformamide there is obtained 5-chloro-3-(4-chloro-2-fluoro-5-isopropoxyphenyl)-1,6-dimethyl-2,4(1H,3H)-pyrimidinedione, m.p. 182°–184° C.

The same product is also obtained from 3-(4-chloro-2 -fluoro-5-isopropoxyphenyl)-1,6-dimethyl-2,4(1H,3H)pyrimidinedione by chlorination with sulphuryl chloride in acetic acid.

EXAMPLE 12

A solution of 10.5 g of ethyl 3-amino-4,4,4-trifluorocrotonate in 25 ml of absolute dimethylformamide is added dropwise while stirring at 0° C. during 5 minutes to a suspension of 2.5 g of a 55% sodium hydride dispersion in 25 ml of absolute dimethylformamide. The temperature rises to 20° C. and the mixture is subsequently stirred at this temperature for 30 minutes. Thereafter, 14.4 g of ethyl N-(4-chloro-2-fluoro-5-isopropoxyphenyl)-carbamate are added, and the mixture is stirred at room temperature for 30 minutes and heated at 150° C. (bath temperature) for 2.5 hours. The reaction mixture is cooled to 50° C., neutralized with 3.5 ml of concentrated acetic acid and largely concentrated at 60° C. under reduced pressure. The residue is poured into a solution of 200 ml of water and 30 ml of 2N hydrochloric acid and the aqueous mixture is extracted twice with 150 ml of diethyl ether each time, and the organic phases are washed twice with 50 ml of water each time, dried over anhydrous sodium sulphate and evaporated to dryness under reduced pressure. The residue is recrystallized from diethyl ether-n-hexane. There is obtained 3-(4-chloro-2-fluoro-5-isopropoxyphenyl)-6-trifluoromethyl-2,4(1H,3H)-pyrimidinedione, m.p. 195°–197° C.

EXAMPLE 13

A solution of 1.0 g of 3-chloro-perbenzoic acid in 15 ml of metyylene chloride is added dropwise while stirring at 0° C. during 1 hour to a solution of 2.3 g of 1-[4-chloro-2-fluoro-5 -(methylthio)methoxy-phenyl]-3-methyl-4-trifluoromethyl-2,6-(1H,3H)-pyrimidinedione in 30 ml of methylene chloride. The reaction mixture is subsequently stirred at room temperature for 15 hours, washed with dilute aqueous sodium bicarbonate solution and then with water and dried over anhydrous sodium sulphate. The organic phase is evaporated to dryness under reduced pressure and the residue is purified by chromatography on a silica gel column using diethyl ether/ethyl acetate and thereafter ethyl acetate alone as the eluent. There is obtained 1-[4-chloro-2-fluoro-5-(methylsulphinyl) methoxy-phenyl]-3-methyl-4-trifluoromethyl-2,6(1H,3H)pyrimidinedione, $^1$H-NMR (CDCl$_3$, 400 MHz): 7.33 ppm (d.1H). 7.27 ppm (2d,1H), 6.34 ppm (2s,1H). 4.91–5.05 ppm (m,2H), 3.54 ppm (d,3H), 2.72 ppm (s,3H).

In an analogous manner:
using 1-[4-chloro-2-fluoro-5-(methylthio)methoxyphenyl]-3-methyl-4 -trifluoromethyl-2,6(1H,3H)-pyrimidinedione with a 0.5 molar excess of 3-chloroperbenzoic acid there is obtained 1-[4-chloro-2-fluoro-5-(methylromethylsulphonyl)methoxy-phenyl]-3-methyl-4 -trifluomethyl-2,6(1H,3H)-pyrimidinedione, m.p. 178°–179° C.; using [4-chloro-2-fluoro-5-(phenylthio)-methoxyphenyl]-1-methyl-6 -trifluoromethyl-2,4(1H,3H)-pyrimidinedione with a 0.15 molar excess of 3-chloro-perbenzoic acid there is obtained 3-[4-chloro-2-fluoro-5-(phenylsulphinyl)methoxy-phenyl]-1-methyl-6-trifluoromethyl -2,4(1H,3H)-pyrimidinedione. $^1$H-NMR (CDCl$_3$, 250 MHz): 63–7.79 ppm (m,2H), 7.47°–7.63 ppm (m,3H). 7.20–7.38 ppm (m,2H), 6.34 ppm (2s,1H), 4.84–5.05 ppm (m,2H), 3.55 ppm (d,3H);

using 3-[4-chloro-2-fluoro-5-(phenylthio)methoxyphenyl]-1-methyl-6-trifluoromethyl-2,4(1H,3H)-pyrimidinedione with a 0.3 molar excess of 3-chloro-perbenzoic acid there is obtained 3-[4-chloro-2-fluoro-5-(phenylsulphonyl)methoxy-phenyl]-1-methyl-6-trifluoromethyl-2,4(1H,3H)-pyrimidinedione. $^1$H-NMR (CDCl$_3$, 250 MHz): 7.95–8.06 ppm (m,2H), 7.65–7.72 ppm (m,1H), 7.52–7.65 ppm (m,2H), 7.27 ppm (d,1H), 7.16 ppm (d,1H), 6.33 ppm (s,1H), 5.06 ppm (s,2H), 3.54 ppm (d,3H).

EXAMPLE 14

A solution of 0.51 g of acetic anhydride and 0.23 g of formic acid in 10 ml of methylene chloride is heated at reflux temperature for 2 hours. Subsequently, 2 μl of pyridine are added and the reaction mixture is stirred at room temperature for 1.5 hours with 1.5 g of 3-(4-chloro-2-fluoro-5-hydroxyphenyl)-1-methyl-6 -trifluoromethyl-2.4 (1H,3H)-pyrimidinedione. The reaction mixture is evaporated to dryness under reduced pressure and the residue is recrystallized from diethyl ether/n-hexane.

There is obtained 2-chloro-5-[3,6-dihydro-2,6-dioxo-3-methyl-4-trifluoromethyl-1(2H)-pyrimidinyl]-4 -fluorophenyl formate, m.p. 97°–99° C.

In an analogous manner:
using 3-[4-chloro-2-fluoro-5-(2-hydroxyethoxy)-phenyl]-1-methyl-6 -trifluoromethyl-2,4(1H,3H)pyrimidinedione with pyridine in diethyl ether there is obtained 2-{2-chloro-5-[3,6-dihydro-2,6-dioxo-3-methyl-4 -trifluoromethyl-1(2H)-pyrimidinyl]-4 -fluorophenoxy}-ethyl formate, $^1$H-NMR (CDCl$_3$, 400 MHz): 8.11 ppm (t,1H), 7.33 ppm (d,1H), 6.82 ppm (d,1H), 6.35 ppm (s,1H), 4.54 ppm (m,2H), 4.22 ppm (t,2H), 3.56 ppm (d,3H).

EXAMPLE 15

A solution of 10.16 g of 3-(4-chloro-2-fluoro-5-hydroxyphenyl)-1-methyl-6-trifluoromethyl-2,4 (1H,3H)-pyrimidinedione and 20.20 g of sulphuryl chloride in 100 ml of methylene chloride is treated with a solution of 3.56 g of pyridine in 10 ml of methylene chloride while stirring and cooling during 5 minutes. The temperature rises to 20° C. The reaction mixture is stirred at 20°-25° C. for 15 minutes, subsequently poured on to ice and stirred vigorously. The organic phase is washed throughly with water, dried over anhydrous sodium sulphate and evaporated to dryness under reduced pressure. The residue is recrystallized from diethyl ether/n-hexane. There is obtained 2-chloro-5-[3,6-dihydro-2,6-dioxo-3-methyl-4-trifluoromethyl-1(2H)-pyrimidinyl]-4-fluorophenyl chlorosulphate m.p. 133°-135° C.

A solution of 1.50 g of the product of the preceding step in 20 ml of methylene chloride is cooled to −70° C. while stirring, a solution of 0.41 g of isopropylamine in 10 ml of methylene chloride is added dropwise during 30 minutes and the mixture is subsequently stirred at 3-70° C. for 2 hours and thereafter 20° C. for 16 hours. The reaction mixture is evaporated to dryness under reduced pressure and the residue is purified by chromatography on a silica gel column using diethyl ether/n-hexane (1:1) as the eluent. The product is subsequently recrystallized from diethyl ether/n-hexane. There is obtained 2-chloro-5-[3,6-dihydro-2,6-dioxo-3-methyl-4-tridinyl]fluoromethyl-1(2H)-pyrimi]-4-fluorophenyl isopropylsulphamate, m.p. 145°-146° C.

EXAMPLE 16

A mixture of 1.70 g of 3-[5-(2-aminoethoxy)-4-chloro-2-fluorophenyl]-1-methyl-6-trifluoromethyl-2,4(1H,3H)-pyrimidinedione, 0.98 g of a 36% aqueous formaldehyde solution and 0.92 g of formic acid is heated to 100° C. for 3 hours while stirring. The reaction mixture is poured into 100 ml of 2% aqueous sodium bicarbonate solution, the oily precipitate is dissolved in ethyl acetate and the solution is washed with water and dried over anhydrous sodium sulphate. The solution is evaporated to dryness under reduced pressure and the resinous residue is purified by chromatography on an aluminium oxide column (neutral, Brockmann I) using ethyl acetate as the eluent. There is obtained 3-{4-chloro-5-[2-(dimethylamino)-ethoxy]-2-fluorophenyl}-1-methyl-6-trifluoromethyl-2,4(1H,3H)-pyrimidinedione, $^1$H-NMR (CDCl$_3$, 400 MHz): 7.31 ppm (d,1H), 6.80 ppm (d,1H), 6.36 ppm (s,1H), 4.09 ppm (d,2H), 3.56 ppm (d,3H), 2.79 ppm (t,2H), 2.35 ppm (s.6H).

EXAMPLE 17

A mixture of 20.3 g of 3-(4-chloro-2-fluoro-5-hydroxyphenyl)-1-methyl-6-trifluoromethyl-2,4(1H,3H)-pyrimidinedione and 8.9 g of 2-ethyl-2-oxazoline is heated at 140° C. for 3 hours. The reaction mixture is dissolved in 50 ml of ethyl acetate, 200 ml of diethyl ether are added, the mixture is extracted with water and the organic phase is dried over anhydrous sodium sulphate. The solution is evaporated to dryness under reduced pressure and the resinous residue is purified by chromatography on a silica gel column using diethyl ether/ethyl acetate (3:1) as the eluent. The product is subsequently recrystallized from diethyl ether. There is obtained N-[2-{2-chloro-5-3,6-dihydro-2,6-dioxo-3-methyl-4-trifluoromethyl-1(2H)-pyrimidinyl]-4-fluorophenoxy}-ethyl]-propionamide, m.p. 100°-103° C.

EXAMPLE 18

A mixture of 2.0 g of 3-[5-(2-aminoethoxy)-4-chloro-2-fluorophenyl]-1-methyl-6-trifluoromethyl-2,4(1H.3H)pyrimidinedione hydrochloride in 20 ml of formic acid are heated to boiling temperature for 20 hours with 0.47 g of triethylamine. The reaction mixture is subsequently evaporated to dryness under reduced pressure, the residue is dissolved in ethyl acetate and extracted with water and thereafter with aqueous sodium bicarbonate solution, and the organic phase is dried over anhydrous sodium sulphate. The solution is thereafter evaporated to dryness under reduced pressure, and the resinous residue is dissolved in ethyl acetate and largely concentrated by evaporation. The residue, still in the liquid state, is treated with diethyl ether until slightly turbid and is seeded. The crystals are filtered off under suction, washed with diethyl ether and dried. There is obtained N-[2-{2-chloro-5-[3,6-dihydro-2,6-dioxo-3-methyl-4-trifluoromethyl-1(2H)-pyrimidinyl]-4-fluorophenoxy}-ethyl]-formamide, m.p. 128°-131° C.

EXAMPLE 19

A solution of 17.0 g of N-[2-{2-chloro-5-[3,6-dihydro-2,6-dioxo-3-methyl-4-trifluoromethyl-1(2H)-pyrimidinyl]-4-fluorophenoxy}-ethyl]propionamide in 100 ml of ethanol is heated at reflux temperature for 5 hours with a solution of 75 ml of concentrated hydrochloric acid in 75 ml of water. The ethanol is subsequently distilled off at 50° C. and the clear aqueous solution is neutralized with sodium bicarbonate. The oily precipitate is dissolved in ethyl acetate and the solution is washed with water, dried over anhydrous sodium sulphate and evaporated to dryness under reduced pressure. The resinous residue is dissolved in 200 ml of 2N hydrochloric acid at 50° C., the mixture is extracted with a small amount of ethyl acetate and the aqueous phase is evaporated under reduced pressure until crystallization occurs. 50 ml of diethyl ether are subsequently added and the mixture is stirred. The crystals are filtered off under suction, washed with diethyl ether and dried at 50° C. in a vacuum. There is obtained 3-[5-(2-aminoethoxy)-4-chloro-2-fluorophenyl]-1-methyl-6-trifluoromethyl-2,4(1H,3H)-pyrimidinedione hydrochloride, m.p. 217°-227° C. (decomposition).

EXAMPLE 20

A solution of 2.0 g of 3-(4-chloro-2-fluoro-5-hydroxyphenyl)-1-methyl-6-trifluoromethyl-2,4(1H,3H)pyrimidinedione is treated with 0.25 g of potassium carbonate and the suspension is saturated with chlorotrifluoroethylene while stirring during 10 minutes. The reaction mixture is subsequently heated to 50° C. for 10 minutes, during which a slow stream of chlorotrifluoroethylene is conducted in. Thereafter, the reaction mixture is poured into a solution of 3 ml of 2N hydrochloric acid in 250 ml of water, and the whole is extracted with 100 ml of ethyl acetate. The organic phase is washed neutral with water, dried over anhydrous sodium sulphate and evaporated to dryness under reduced pressure. The resinous residue is purified by chromatography on a silica gel column using diethyl ether/n-hexane (1:3) as the eluent. There is obtained 3-[4-chloro-5-(2-chloro-1,1,2-trifluoroethoxy)-2-fluorophenyl]-1-methyl-6-trifluoromethyl-2,4(1H,3H)-pyrimidinedione, $^1$H-NMR (CDCl$_3$, 400 MHz : 7.40 ppm (d,1H), 7.32 ppm (m,1H), 6.37 ppm (s,1H), 6.33 ppm (m,1H), 3.57 ppm (d,3H).

II. Production of the compounds of formulae III, XI, XII, XIII, XIV, XV and XVI

EXAMPLE 21

25 ml of concentrated sulphuric acid are added dropwise at room temperature while stirring and cooling during 1 minute to a solution of 22.4 g of 3-(4-chloro-2-fluoro-5-isopropoxyphenyl)-1-methyl-6-trifluoromethyl-2,4(1H,3H)-pyrimidinedione in 50 ml of methylene chloride. The reaction mixture is stirred at room temperature for 2 hours and poured onto 100 g of ice. The organic phase is separated, washed twice with 50 ml of water each time and dried over anhydrous sodium sulphate and evaporated to dryness under reduced pressure. The residue is recrystallized from diethyl ether/n-hexane. There is obtained 3-(4-chloro-2-fluoro-5-hydroxyphenyl)-1-methyl-6-trifluoromethyl-2,4(1H,3H)-pyrimidinedione, m.p. 169°–171° C.

In an analogous manner:
using 3-(4-bromo-2-fluoro-5-isopropoxyphenyl)-1-methyl-6-trifluoromethyl-2,4(1H,3H)-pyrimidinedione there is obtained 3-(4-bromo-2-fluoro-5-hydroxyphenyl)-1-methyl-6-trifluoromethyl-2,4(1H,3H)-pyrimidinedione. m.p. 192° C.

EXAMPLE 22

A solution of 4.67 g of ethyl 3-amino-4,4,4-trifluorocrotonate in 15 ml of toluene is added dropwise while stirring at 0° C. during 20 minutes to a suspension of 1.11 g of a 55% sodium hydride dispersion in 30 ml of absolute dimethylformamide, and the mixture is stirred at 0° C. for 15 minutes. The reaction mixture is subsequently cooled to -40° C. and a solution of 6.24 g of 2-chloro-4-fluoro-5-isocyanatophenyl methyl carbonate in 30 ml of toluene is added dropwise during 5 minutes. The reaction mixture is stirred at room temperature for 1 hour and stirred for a further 30 minutes with a solution of 5.40 g of sodium carbonate in 100 ml of water. The aqueous phase is separated. extracted twice with 50 ml of diethyl ether each time and adjusted to pH 1 with 8 ml of 2N hydrochloric acid. The mixture is extracted twice with 100 ml of diethyl ether each time and the organic phases are washed with water. dried over anhydrous sodium sulphate and evaporated to dryness under reduced pressure. The residue is recrystallized from diethyl ether/n-hexane. There is obtained 3-(4-chloro-2-fluoro-5-hydroxyphenyl)-6-trifluoromethyl-2,4(1H,3H)-pyrimidinedione, m.p. 223°–225° C.

EXAMPLE 23

22.8 g of ethyl chloroformate are added dropwise to a solution of 22.2 g of o-fluoroaniline in 25 ml of pyridine and 80 ml of n-hexane at 0° C. in such a manner that the temperature of the reaction mixture does not exceed 5° C. After filtering off the pyridine hydrochloride which is formed the filtrate is concentrated and the residue is dried under reduced pressure. In this manner there is obtained ethyl o-fluorocarbanilate which is used in the next reaction step without purification.

| | Microanalysis: | | | |
|---|---|---|---|---|
| | C % | H % | N % | F % |
| Calculated | 59.01 | 5.50 | 7.65 | 10.37 |
| Found | 59.12 | 5.67 | 7.55 | 10.30 |

5.5 g of the above intermediate and 5.4 g of sodium acetate are suspended in 25 ml of glacial acetic acid. The suspension is treated at 50° C. with 4.8 ml of sulphuryl chloride and the reaction mixture is subsequently held at this temperature for 30 minutes. The mixture is then poured on to 200 ml of ice-water. whereby the desired ethyl 4-chloro-2-fluorocarbanilate crystallizes out. $^1$H-NMR (CDCl$_3$, 60 MHz): 8.1 ppm (t,1H), 7.1 ppm (d,2H), 6.8 ppm (broad s,1H), 4.25 ppm (q,2H), 1.3 ppm (t,3H). 51.0 g of ethyl 3-amino-4,4,4-trifluorocrotonate are added to a suspension of 15.6 g of sodium methylate in 150 ml of dimethylformamide in such a manner that the temperature of the reaction mixture does not exceed 30° C. 60.9 g of ethyl 4-chloro-2-fluorocarbanilate are added to the resulting yellow suspension and the mixture is heated at 130° C. for 2 hours while constantly distilling off methanol and ethanol. The mixture is then poured on to 800 ml of ice-water and washed three times with 100 ml of diethyl ether each time. The aqueous phase is acidified with concentrated hydrochloric acid and extracted three times with 250 ml of ethyl acetate each time. and the combined organic phases are subsequently washed in sequence with 5% aqueous sodium chloride solution and ethanol, dried over anhydrous sodium sulphate and evaporated. The oily crude product is crystallized from diethyl ether/n-hexane. There is obtained 3-(4-chloro-2-fluorophenyl)6-trifluoromethyl-2,4(1H,3H)-pyrimidinedione, m.p. 189° C.

In an analogous manner, using ethyl o-fluorocarbanilate and bromine there is obtained ethyl 4-bromo-2-fluorocarbanilate, m.p. 72°–73° C. and from this and ethyl 3-amino-4.4.4-trifluorocrotonate there is obtained 3-(4-bromo-2-fluorophenyl)-6-trifluoromethyl-2,4(1H,3H)-pyrimidinedione, m.p. 205° C.

In an analogous manner, starting from ethyl 4-chloro-2-fluorocarbanilate and ethyl 3-aminocrotonate there is obtained 3-(4-chloro-2-fluorophenyl)-6-methyl-2,4(1H,3H) -pyrimidinedione. m.p. >220° C.; mass spectrum (m/e): 254 (M+), 235, 219, 17, 143, 108, 83, 68, 42;

| | Microanalysis: | | | | |
|---|---|---|---|---|---|
| | C % | H % | N % | F % | Cl % |
| Calculated | 51.69 | 3.31 | 11.01 | 7.34 | 13.76 |
| Found | 51.88 | 3.17 | 11.00 | 7.46 | 13.92 |

EXAMPLE 24

A suspension of 6.17 g of 3-(4-chloro-2-tluorophenyl)-6-trifluoromethyl-2,4(1H 3H)-pyrimidinedione, 5.5 g of potassium carbonate and 2.9 ml of dimethyl sulphate in 40 ml of acetonitrile is stirred at 55° C. for 60 minutes and subsequently poured into 150 ml of water. The aqueous solution is extracted three times with 50 ml of ethyl acetate each time, and the combined organic phases are dried over anhydrous sodium sulphate and evaporated. The resulting oily residue is crystallized from diethyl ether/n-hexane. There is thus obtained 3-(4-chloro-2-fluorophenyl)-1-methyl-6-trifluoromethyl-2,4(1H,3H)-pyrimidinedione, m.p. 108° C.

9.7 g of the product of the preceding reaction step are added portionwise to a solution, cooled to −15° C., of 2.2 ml of nitric acid (60%) and 25 ml of sulphric acid. The reaction mixture is stirred at room temperature for 30 minutes and subsequently poured onto 150 ml of icewater. The product, 3-(4-chloro-2-fluoro-5-nitrophenyl)-1-methyl-6 -trifluoromethyl-2,4(1H,3H)-pyrimidinedione. crystallizes out and is filtered off. M.p. 124° C.

In place of the above-described methylation followed by the nitration, the nitration can be carried out as the first reaction step and the methylation as the second reaction step, namely as follows:

A nitrating solution consisting of 2.2 ml of nitric acid and 24 ml of sulphuric acid is pre-cooled to −15° C. 9.26 g of 3-(4-chloro-2-fluorophenyl)-6 -trifluoromethyl-2,4(1H,3H)-pyrimidinedione are added portion wise to the solution while stirring. The mixture is stirred at 15° C. for 30 minutes and subsequently at room temperature for 1 hour. Thereafter, the mixture is poured onto 150 ml of ice-water and the resulting crystalline precipitate is filtered off. In this manner there is obtained 3-(4-chloro-2-fluoro-5-nitrophenyl)-6 -trifluoromethyl-2,4(1H,3H)-pyrimidinedione. m.p. 204° C.

49.5 g of the product of the preceding reaction step are dissolved in 300 ml of acetonitrile. 38.7 g of potassium carbonate and 15.3 ml of dimethyl sulphate are then added thereto and the reaction mixture is stirred at 55° C. for 2.5 hours. The solvent is subsequently distilled off and the residual mixture is extracted three times with 100 ml of ethyl acetate each time. The combined organic phases are dried over anhydrous sodium sulphate. the solvent is distilled off and the oily residue is subjected to a chromatographic purification using 300 g of silica gel as well as n-hexane/ethyl acetate (4:1). The product, 3-(4-chloro-2-fluoro-5-nitrophenyl)-1-methyl-6-trifluoromethyl-2,4(1H,3H)-pyrimidinedione, crystallizes from n-hexane/ethyl acetate.

In an analogous manner:
using 3-(4-bromo-2-fluorophenyl)-6-trifluoromethyl-2,4(1H,3H)-pyrimidinedione there is obtained by methylation 3-(4-bromo-2-fluorophenyl)-1 -methyl-6-trifluoromethyl-2,4(1H,3H)-pyrimidinedione and from this by nitration there is obtained 3-(4-bromo-2-fluoro-5-nitrophenyl)-1 -methyl-6-trifluoromethyl-2,4(1H,3H)-pyrimidinedione, m.p. 124°-125° C.;

using 3-(4-bromo-2-fluorophenyl)-6-trifluoromethyl -2,4(1H,3H)-pyrimidinedione there is obtained by nitration 3-(4-bromo-2-fluoro-5-nitrophenyl)-6 -trifluoromethyl-2,4(1H,3H)-pyrimidinedione and from this by methylation there is obtained 3-(4-bromo-2-fluoro-5-nitrophenyl)-1-methyl-6-trifluoromethyl-2,4(1H,3H)-pyrimidinedione, m.p. 24°-125° C.;

using 3-(4-chloro-2-fluorophenyl)-6-methyl-2,4(1H,3H)-pyrimidinedione there is obtained by methylation 3-(4chloro-2-fluorophenyl)-1,6 -dimethyl-2,4(1H,3H)-pyrimidinedione, m.p. 145° C. and from this by nitration there is obtained 3-(4-chloro-2-fluoro-5-nitrophenyl)-1,6 -dimethyl-2,4(1H,3H)-pyrimidinedione, m.p. 65°-172° C.; $^1$H-NMR (D$_6$-DMSO, 60 MHz): 8.55 ppm (d,J=7 Hz. 1H), 8.20 ppm (d,J=10 Hz,1H), 3.51 ppm (s,3H), 2.52 ppm s,3H);

using 3-(4-chloro-2-fluorophenyl)-6-methyl-2,4(1H,3H)-pyrimidinedione there is obtained by nitration 3-(4-chloro-2-fluoro-5-nitrophenyl)-6 -methyl-2,4(1H,3H)-pyrimidinedione and from this by methylation there is obtained by methylation 3-(4-chloro-2-fluoro-5-nitrophenyl)-1,6-dimethyl-2,4(1H,3H)-pyrimidinedione (physical data as above).

EXAMPLE 25

A mixture consisting of 2.45 g of iron powder. 8 ml of water and 16 ml of ethanol is heated to 80° C. by means of an oil bath. After removing the oil bath 3.14 g of 3-(4-chloro-2-fluoro-5-nitrophenyl)-1,6 -dimethyl -2,4(1H,3H)-pyrimidinedione are added portionwise in such a manner that the reaction solution is held at the reflux temperature. After completion of the addition a spatula tip of active harcoal is added thereto and the reaction mixture is held at the reflux temperature for a few minutes longer. The mixture is then filtered and the colourless filtrate is concentrated. The product crystallizes out upon cooling the resulting oil. There is obtained 3-(5-amino-4-chloro-2-flurophenyl)-1,6-dimethyl-2,4(1H,3H)-pyrimidinedione, m.p. >220° C.; mass spectrum (m/e): 283 (M+), 186, 98;

|  | Microanalysis: | | | | |
| --- | --- | --- | --- | --- | --- |
|  | C % | H % | N % | F % | Cl % |
| Calculated | 50.81 | 3.91 | 14.81 | 6.70 | 12.50 |
| Found | 50.60 | 4.16 | 14.64 | 6.50 | 12.39 |

In an analogous manner:
using 3-(4-chloro-2-fluoro-5-nitrophenyl)-1-methyl-6-trifluoromethyl-2,4(1H,3H)-pyrimidinedione there is obtained 3-(5-amino-4-chloro-2-fluorophenyl)-1-methyl-6-trifluoromethyl-2,4(1H,3H)-pyrimidinedione, m.p. 129° C.;

using 3-(4-bromo-2-fluoro-5-nitrophenyl)-1-methyl-6-trifluoromethyl-2,4(1H,3H)-pyrimidinedione there is obtained 3-(5-amino-4-bromo-2-fluorophenyl)-1-methyl-6-trifluoromethyl-2,4(1H,3H)-pyrimidinedione. m.p 145° C.

EXAMPLE 26

4.24 g of boron trifluoride etherate and 6.75 g of 3-(5-amino-4-chloro-2-fluorophenyl)-1 -methyl-6-trifluoromethyl-2,4(1H,3H)-pyrimidinedione are placed at −15° C. in 50 ml of methylene chloride. A solution of 3.2 ml of isopentyl nitrite in 20 ml of methylene chloride is added dropwise to the mixture within 20 minutes while cooling. The mixture is subsequently stirred at 5° C. for 45 minutes, 25 treated with 50 ml of n-pentane and the resulting crystals are filtered off. There is obtained 2-chloro-5-[3,6-dihydro-2,6-dioxo -3-methyl-4-trifluoromethyl-1(2H)-pyrimidinyl]-4-fluorobenzenediazonium tetrafluoroborate. m.p. 191° C. (decomposition).

In an analogous manner:
using 3-(5-amino-4-bromo-2-fluorophenyl)-1 -methyl-6-trifluoromethyl-2,4(1H,3H)-pyrimidinedione there is obtained 2-bromo-5-[3,6-dihydro-2,6-dioxo -3-methyl-4-trifluoromethyl-1 (2H)-pyrimidinyl]-4-fluorobenzenediazonium tetrafluoroborate. m.p. 218°-220° C. (decomposition)

using 3-(5-amino-4-chloro-2-fluorophenyl) -1,6-dimethyl-2,4(1H,3H)-pyrimidinedione there is obtained 2-chloro-5-[3,6-dihydro-2,6-dioxo -3,4-dimethyl-1(2H)-pyrimidinyl]-4-fluorobenzenediazonium tetrafluoroborate,
m.p. 248°-253° C. (decomposition).

EXAMPLE 27

0 23 g of 2-chloro-5-[3,6-dihydro-2,6-dioxo -3-methyl-4-trifluoromethyl-1(2H)-pyrimidinyl]-4-fluorobenzenediazonium tetrafluoroborate is added to a solution of 75 g of cupric nitrate trihydrate in 50 ml of water. 67 mg of cuprous oxide are added thereto and the reaction mixture is stirred at room temperature for 10 minutes. The mixture is subsequently filtered, the filtrate is extracted with 50 ml of ethyl acetate and the organic phase is washed and evaporated under reduced pressure. The resulting crude product is crystallized from diethyl ether/n-hexane. There is obtained 3-(4-chloro-2-fluoro-5-hydroxyphenyl)-1-methyl-6 -trifluoromethyl-2,4(1H,3H)-pyrimidinedione.

In an analogous manner:

using 2-bromo-5-[3,6-dihydro-2,6-dioxo -3-methyl-4-trifluoromethyl-1(2H)-pyrimidinyl]4-fluorobenzenediazonium tetrafluoroborate there is obtained 3-(4-bromo -2-fluoro-5-hydroxyphenyl)-1-methyl-6 -trifluoromethyl-2,4(1H,3H)-pyrimidinedione;

using 2-chloro-5-[3,6-dihydro-2,6-dioxo -3,4-dimethyl1(2H)-pyrimidinyl]-4-fluorobenzenediazonium tetrafluoroborate there is obtained 3-(4-chloro-2-fluoro-5-hydroxyphenyl)-1,6-dimethyl-2,4(1H,3H)-pyrimidinedione.

III. Production of the compounds of formula IX

EXAMPLE 28

The novel ethyl N-(4-chloro-2-fluoro-5-isopropoxyphenyl)-carbamate used in Example 12 can be produced as follows 12.8 g of ethyl chloroformate are added while stirring to a solution of 20 g of 4-chloro-2-fluoro-5-isopropoxyaniline in 100 ml of methylene chloride at room temperature. 9.4 g of pyridine are subsequently added dropwise during 20 minutes at 20° C. while stirring and cooling. The reaction mixture is stirred for 20 minutes, washed three times with in each case 200 ml of a solution of 20 ml of 2N hydrochloric acid in 200 ml of water, dried over anhydrous sodium sulphate and evaporated to dryness under reduced pressure. There is obtained ethyl N-(4-chloro-2-fluoro-5-isopropoxyphenyl)-carbamate, m.p. 89°–91° C.

IV. Formulation Examples

EXAMPLE 29

An emulsifiable concentrate contains the following ingredients:

| | |
|---|---|
| A compound of formula I, III, XI XII, XIII, XIV, XV or XVI (active substance) | 50 g/l |
| N—Methylpyrrolidone (auxiliary solvent) | 200 g/l |
| Nonylphenol-(10)ethoxylate (non-ionic emulsifier) | 50 g/l |
| Calcium dodecylbenzenesulphonate (anionic emulsifier) | 25 g/l |
| Mixture of alkylbenzenes (solvent) ad | 1000 ml | active substance and the emulsifiers are dissolved in the auxiliary solvent while stirring and the solution is made up to 1 liter with the solvent.

The resulting emulsifiable concentrate can emulsify in water and then gives a ready-for-use spray liquor having the desired concentration.

EXAMPLE 30

The ingredients listed hereinafter are mixed with one another for the manufacture of a 25% spray liquor:

| | |
|---|---|
| A compound of formula I, III, XI, XII, XIII, XIV, XV or XVI (active substance) | 25 g |
| Silicic acid, hydrated | 5 g |
| Sodium lauryl sulphate | 1 g |
| Sodium lignosulphonate | 2 g |
| Kaolin | 67 g |
| | 100 g |

The mixture is subsequently finely ground using a pinned disc mill or comparable milling apparatus.

Upon stirring in water the resulting spray powder gives a fine suspension which is suitable as a ready-for-use spray liquor.

We claim:

1. A compound of the formula

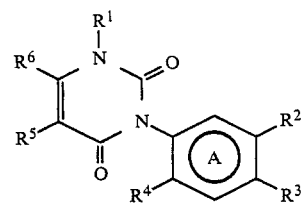

wherein $R^1$ is $C_{1-4}$-alkyl, $C_{1-4}$-haloalkyl, formyl or $C_{2-6}$-alkanoyl, $R^2$ is an ether group or a group containing a (thio)carbonyloxy or sulphonyloxy, whereby this group is directly attached to the benzene nucleus A via the oxygen atom, $R^3$ is halogen or cyano, $R^4$ is hydrogen or halogen, $R^5$ is hydrogen, halogen or $C_{1-4}$ alkyl, $R^6$ is $C_{1-4}$-alkyl or $C_{1-4}$-haloalkyl, or $R^5$ and $R^6$ are tetramethylene.

2. A compound according to claim 1, wherein $R^2$ is $C_{1-8}$-alkoxy, $C_{3-7}$-cycloalkoxy, $C_{3-8}$-alkenoxy, $C_{3-6}$-alkynoxy, $C_{4-8}$-cycloalkylalkoxy, phenyl-$C_{1-4}$-alkoxy, phenyl-$C_{1-4}$-alkoxy substituted with substituents selected from the group consisting of halo, nitro, cyano, lower alkyl, haloalkyl, and alkoxy; $C_{1-8}$-haloalkoxy, $C_{3-9}$-haloalkenoxy, $C_{2-8}$-alkoxy alkoxy, phenoxy-C-4-alkoxy, phenoxy-$C_{1-4}$-alkoxy substituted with substituent substituents selected from the group consisting of halo, nitro, cyano, lower alkyl, haloalkyl, and alkoxy; $C_{4-8}$-haloalkenoxyalkoxy, $C_{2-8}$-alkylthioalkoxy, N-alkyl- or N,N-dialkylcarbamoylalkoxy in which the sum of the carbon atoms is 2 to 10, $C_{3-8}$-alkynoyloxy, N-alkyl- or N,N- dialkylcarbamoyloxy which the sum of the carbon atoms is 2 to 10, $C_{1-8}$-alkylsulphonyloxy, phenylsulphonyloxy, phenylsulphonyloxy substituted with substituent substituents selected from the group consisting of halo, nitro, cyano, lower alkyl, haloalkyl, and alkoxy; or N-alkyl- or N,N- dialkylsulphamoyloxy in which the sum of the carbon atoms is 1 to 8.

3. A compound according to claim 2, wherein $R^2$ is $C_{1-3}$-alkoxy, allyloxy or propargyloxy.

4. A compound according to claim 2, wherein $R^3$ is chlorine or bromine.

5. A compound according to claim 2, wherein $R^4$ is fluorine.

6. A compound according to claim 2, wherein $R^5$ is hydrogen, fluorine or methyl.

7. A compound according to claim 2, wherein $R^6$ is methyl or trifluoromethyl.

8. A compound according to claim 1, wherein $R^5$ is hydrogen.

9. A compound according to claim 1, wherein $R^4$ is fluorine and $R^5$ is hydrogen.

10. A compound according to claim 1, wherein $R^5$ is hydrogen and $R^6$ is trifluoromethyl.

11. A compound according to claim 1, wherein $R^1$ is methyl, $R^4$ is fluorine, $R^5$ is hydrogen and $R^6$ is trifluoromethyl.

12. A compound according to claim 1, wherein $R^1$ is methyl, $R^3$ is chlorine, $R^4$ is fluorine, $R^5$ is hydrogen and $R^6$ is trifluoromethyl.

13. A compound according to claim 1 selected from the group consisting of
3-(4-Chloro-2-fluoro-5-propargyloxyphenyl)-1-methyl-6-trifluoromethyl-2,4(1H,3H)-pyrimidinedione,
3-(4-chloro-2-fluoro-5-isopropoxyphenyl)-1-methyl-6-trifluoromethyl-2,4(1H,3H)-pyrimidinedione,
3-(5-ethoxy-4-chloro-2-fluorophenyl)-1-methyl-6-trifluoromethyl-2,4(1H,3H)-pyrimidinedione.
3-(4-chloro-2-fluoro-5-methoxyphenyl)-1-methyl-6-trifluoromethyl-2,4(1H.3H)-pyrimidinedione,
b 3-(5-butoxy-4-chloro-2-fluorophenyl)-1-methyl-6-trifluoromethyl-2,4(1H,3H)-pyrimidinedione,
3-(4-chloro-2-fluoro-5-propoxyphenyl)-1-methyl-6-trifluoromethyl-2,4(1H,3H)-pyrimidinedione,
3-(5-allyloxy-4-chloro-2-fluorophenyl)-1-methyl-6-trifluoromethyl-2,4(1H,3H)-pyrimidinedione,
3-(4-chloro-2-fluoro-5-isopropoxyphenyl)-1-methyl-6-pentafluoroethyl-2,4(1H,3H)-pyrimidinedione, 3(4-chloro-2-fluoro-5-isopropoxyphenyl)-5-fluoro-1-methyl-6-pentafluoroethyl-2,4(1H,3H)-pyrimidinedione,
3-(4-chloro-2-fluoro-5-methoxymethoxy-phenyl)-1-methyl-6-trifluoromethyl-2,4(1H,3H)-pyrimidinedione,
2-chloro-5-[3,6-dihydro-2,6-dioxo-3-methyl-4-trifluoromethyl-1(2H)-pyrimidinyl]-4-fluorophenyl N-tert.butylcarbamate,
3-[5-(2-bromoethoxy)-4-chloro-2-fluorophenyl]-1-methyl-6-trifluoromethyl-2,4(1H,3H)-pyrimidinedione,
2-chloro-5-[3,6-dihydro-2,6-dioxo-3-methyl-4-trifluoromethyl-1(2H)-pyrimidinyl]-4-fluorophenyl p-chlorobenzenesulphonate.
3-[4-chloro-5-(3,3-dichloroallyloxy)-2-fluorophenyl]-1-methyl-6-trifluoromethyl-2,4(1H,3H)-pyrimidinedione.
3-{4-chloro-5-[2-(2,2-dichlorovinyloxy)-ethoxy]-2-fluorophenyl}-1-methyl-6-trifluoromethyl-2,4(1H,3H)-pyrimidinedione,
3-{4-chloro-2-fluoro-5-[2-(2-methoxyethoxy)-ethoxy]-phenyl}-1-methyl-6-trifluoromethyl-2,4(1H,3H)-pyrimidinedione,
2-chloro-5-[3,6-dihydro-2,6-dioxo-3-methyl-4-trifluoromethyl-1(2H)-pyrimidinyl]-4-fluorophenyl dimethylsulphamate,
2-chloro-5-[3,6-dihydro-2,6-dioxo-3-methyl-4-trifluoromethyl-1(2H)-pyrimidinyl]-4-fluorophenyl methanesulphonate,
3-(4-chloro-2-fluoro-5-methylthiomethoxy-phenyl)-1-methyl-6-trifluoromethyl-2,4(1H,3H)-pyrimidinedione,
3-(4-chloro-5-difluoromethoxy-2-fluorophenyl)-1-methyl-6-trifluoromethyl-2,4(1H,3H)-pyrimidinedione,
2-chloro-5-[3,6-dihydro-2,6-dioxo-3-methyl-4-trifluoromethyl-1(2H)-pyrimidinyl]-4-fluorophenyl 2-propiolate,
3-[4-chloro-2-fluoro-5-(2-methoxyethoxy)-phenyl]-1-methyl-6-trifluoromethyl-2,4(1H,3H)-pyrimidinedione.
3-[5-(2-ethoxyethoxy)-4-chloro-2-fluorophenyl]-1-methyl-6-trifluoromethyl-2,4(1H,3H)-pyrimidinedione,
3-{4-chloro-5-[(p-chlorophenoxy)methoxy]-2-fluorophenyl}-1-methyl-6-trifluoromethyl-2,4(1H,3H)-pyrimidinedione,
3-(5-benzyloxy-4-chloro-2-fluorophenyl)-1-methyl-6-trifluoromethyl-2,4(1H,3H)-pyrimidinedione,
2-{2-chloro-5-[3,6-dihydro-2,6-dioxo-3-methyl-4-trifluoromethyl-1(2H)-pyrimidinyl]-4-fluorophenoxy}-N,N-dimethyl-acetamide,
3-(4-chloro-2-fluoro-5-isopropoxyphenyl)-1-difluoromethyl-6-methyl-2,4(1H,3H)-pyrimidinedione and
3-(4-chloro-5-cyclopentoxy-2-fluorophenyl)-1-methyl-6-trifluoromethyl-2,4(1H,3H)-pyrimidinedione.

14. A compound in accordance with claim 1, 3-(4-Chloro-5-cyclohexylmethoxy-2-fluorophenyl)-1-methyl-b-trifluoromethyl-2,4(1H,3H)-pyrimidinedione.

15. A compound in accordance with claim 1, 2-Chloro-5-[3,6-dihydro-2,6-dioxo-3-methyl-4-trifluoromethyl-1(2H)-pyrimidinyl]-4-fluorophenylisopropane-sulphonate.

16. A compound of the formula

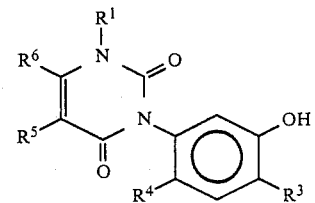

III wherein
$R^1$ is $C_{1-4}$-alkyl, $C_{1-4}$-haloalkyl, formyl, or $C_{2-6}$-alkanoyl,
$R^3$ is halogen or cyano,
$R^4$ is hydrogen or halogen,
$R^5$ is hydrogen, halogen or $C_{1-4}$-alkyl,
$R^6$ is $C_{1-4}$-alkyl or $C_{1-4}$-haloalkyl
$R^5$ and $R^6$ together are tri- or tetramethylene.

17. A compound in accorance with claim 16, wherein is $C_{1-4}$-alkyl, $C_{1-4}$-haloalkyl, formyl or $C_{2-6}$-alkanoyl.

18. A compound in accordance with claim 16, 3-(4-chloro-2-fluoro-5-hydroxyphenyl)-1-methyl-6-trifluoromethyl-2-4(1H, 3H)-pyrimidinedione.

19. A compound of the formula

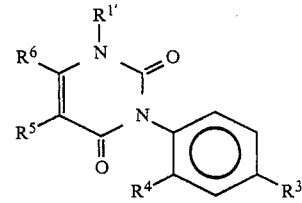

XII wherein $R^1$ is $C_{1-4}$-alkyl or $C_{1-4}$-haloalkyl,
$R^3$ is halogen or cyano,
$R^4$ is hydrogen or halogen,
$R^5$ is hydrogen, halogen or $C_{1-4}$-alkyl,
$R^6$ is $C_{1-4}$-alkyl or $C_{1-4}$-haloalkyl
$R^5$ and $R^6$ together are tri- or tetramethylene.

20. A compound of the formula

XIV wherein
$R^{1\prime}$ is $C_{1-4}$-alkyl or $C_{1-4}$-haloalkyl,
$R^3$ is halogen or cyano,
$R^4$ is hydrogen or halogen,
$R^5$ is hydrogen, halogen or $C_{1-4}$-alkyl,
$R^6$ is $C_{1-4}$-alkyl or $C_{1-4}$-haloalkyl
$R^5$ and $R^6$ together are tri- or tetramethylene.

21. A compound of the formula

XV wherein
$R^{1\prime}$ is $C_{1-4}$-alkyl or $C_{1-4}$-haloalkyl,
$R^3$ is halogen or cyano,
$R^4$ is hydrogen or halogen,
$R^5$ is hydrogen, halogen or $C_{1-4}$-alkyl,
$R^6$ is $C_{1-4}$-alkyl or $C_{1-4}$-haloalkyl
$R^5$ and $R^6$ together are tri- or tetramethylene.

22. A compound of the formula

XVI wherein
$R^1$ is $C_{1-4}$-alkyl or $C_{1-4}$-haloalkyl,
$R^3$ is halogen or cyano,
$R^4$ is hydrogen or halogen,
$R^5$ is hydrogen, halogen or $C_{1-4}$-alkyl,
$R^6$ is $C_{1-4}$-alkyl or $C_{1-4}$-haloalkyl
$R^5$ and $R^6$ together are tri- or tetramethyloene and
$A^-$ is an anion, selected from the group consisting of halide, hydrogen sulphate, or tetrafluoroborate.

23. A weed control composition, which contains an effective amount of at least one compound of the formula

I wherein
$R^1$ is $C_{1-4}$-alkyl, $C_{1-4}$-haloalkyl, formyl or $C_{2-6}$-alkanoyl,
$R^2$ is an ether group or a group containing a (thio)carbonyloxy or sulphonyloxy, whereby this group is directly attached to the benzene nucleus A via the oxygen atom,
$R^3$ is halogen or cyano,
$R^4$ is hydrogen or halogen,
$R^5$ is hydrogen, halogen or $C_{1-4}$-alkyl,
$R^6$ is $C_{1-4}$-alkyl or $C_{1-4}$-haloalkyl, or
$R^5$ and $R^6$ together are tri- or tetramethylene, as well as formulation adjuvants.

24. A weed control composition according to claim 23, which contains an effective amount of at least one compound selected from the group consisting of
3-(4-chloro-2-fluoro-5-propargyloxyphenyl)-1-methyl-6-trifluoromethyl-2,4(1H,3H)-pyrimidinedione,
3-(4-chloro-2-fluoro-5-isopropoxyphenyl)-1-methyl-6-trifluoromethyl-2,4(1H,3H)-pyrimidinedione,
3-(5-ethoxy-4-chloro-2-fluorophenyl)-1-methyl-6-trifluoromethyl-2,4(1H,3H)-pyrimidinedione,
3-(4-chloro-2-fluoro-5-methoxyphenyl)-1-methyl-6-trifluoromethyl-2,4(1H.3H)-pyrimidinedione,
3-(5-butoxy-4-chloro-2-fluorophenyl)-1-methyl-6-trifluoromethyl-2,4(1H.3H)-pyrimidinedione,
3-(4-chloro-2-fluoro-5-propoxyphenyl)-1-methyl-6-trifluoromethyl-2,4(1H,3H)-pyrimidinedione.
3-(5-allyloxy-4-chloro-2-fluorophenyl)-1-methyl-6-trifluoromethyl-2,4(1H,3H)-pyrimidinedione,
3-(4-chloro-2-fluoro-5-isopropoxyphenyl)-1-methyl-6-pentafluoroethyl-2,4(1H,3H)-pyrimidinedione,
3-(4-chloro-2-fluoro-5-isopropoxyphenyl)-5-fluoro-1-methyl-6-pentafluoroethyl-2,4(1H,3H)-pyrimidinedione,
3-(4-chloro-2-fluoro-5-methoxymethoxy-phenyl)-1-methyl6-trifluoromethyl-2,4(1H,3H)-pyrimidinedione,
2-chloro-5-[3,6-dihydro-2,6-dioxo-3-methyl-4-trifluoromethyl-1(2H)-pyrimidinyl]-4-fluorophenyl N-tert.butylcarbamate,
3-[5-(2-bromoethoxy)-4-chloro-2-fluorophenyl]-1-methyl-6-trifluoromethyl-2,4(1H,3H)-pyrimidinedione,
2-chloro-5-[3,6-dihydro-2,6-dioxo-3-methyl-4-trifluoromethyl-1(2H)-pyrimidinyl]-4-fluorophenyl p-chlorobenzenesulphonate,
3-[4-chloro-5-(3,3-dichloroallyloxy)-2-fluorophenyl]-1-methyl-6-trifluoromethyl-2,4(1H,3H)-pyrimidinedione,.
3-[4-chloro-5-[2-(2,2-dichlorovinyloxy)-ethoxy]-2-fluorophenyl}-1-methyl-6-trifluoromethyl-2,4(1H,3H)-pyrimidione,
3-{4-chloro-2-fluoro-5-[2-(2-methoxyethoxy)-ethoxy]-phenyl}-1-methyl-6-trifluoromethyl-2,4(1H,3H)-pyrimidinedione, 2-chloro-5-[3,6-dihydro-2,6-dioxo-3-methyl-4-trifluoromethyl-1(2H)-pyrimidinyl]-4-fluorophenyl dimethylsulphamate, 2-chloro-5-[3,6-dihydro-2,6-dioxo-3-methyl-4-trifluoromethyl-1(2H)-pyrimidinyl]-4-fluorophenyl methanesulphonate, 3-(4-chloro-2-fluoro-5-methylthiomethoxy-phenyl)-1-methyl-6-trifluoromethyl-2,4(1H,3H)-pyrimidinedione, 3-(4-chloro-5-difluoromethoxy-2-fluorophenyl)-1-methyl -6-trifluoromethyl-2,4(1H,3H)-pyrimidinedione, 2-chloro-5-[3,6-dihydro-2,6-dioxo-3-methyl-4-trifluoromethyl-1(2H)-pyrimidinyl]-4-fluorophenyl 2-propiolate, 3-[4-chloro-2-fluoro-5-(2-methoxyethoxy)-phenyl]-1-methyl-6-trifluoromethyl-2,4(1H,3H)-pyrimidinedione, 3-[5-(2-ethoxyethoxy)-4-chloro-2-fluorophenyl]-1-methyl-6-trifluoromethyl-2,4(1H,3H)-pyrimidinedione, 3-{4-chloro-5-[(p-chlorophenoxy)methoxy]-2-fluorophenyl}-1-methyl-6-trifluoromethyl-2,4(1H,3H)-pyrimidinedione, 3-(5-benzyloxy-4-chloro-2-fluorophenyl)-1-methyl-6-trifluoromethyl-2,4(1H,3H)-pyrimidinedione, 2-{2-chloro-5-[3,6-dihydro-2,6-dioxo-3-methyl-4-trifluoromethyl-1(2H)-pyrimidinyl]-4-fluorophenoxy}-N,N-dimethyl-acetamide, 3-(4-chloro-2-fluoro-5-isopropoxyphenyl)-1-difluoromethyl-6-methyl-2,4(1H,3H)-pyrimidinedione and 3-(4-chloro-5-cyclopentoxy-2-fluorophenyl)-1-methyl-6-trifluoromethyl-2,4(1H,3H)-pyrimidinedione as well as formulation adjuvants.

25. A weed control composition according to claim 23, which contains an effective amount of a compound selected from the group consisting of 3-(4-chloro-5-cyclohexylmethoxy-2-fluorophenyl)-1-methyl-6 -trifluoromethyl-2,4(1H,3H)-pyrimidinedione and 2-chloro-5-[3,6-dihydro -2,6-dioxo-3-methyl-4 -trifluoromethyl-1(2H)-pyrimidinyl]-4-trifluorophenyl isopropanesulphonate as well as formulation adjuvants.

26. A weed control composition, which contains an effective amount of a compound in accordance with claim 16 and one or more formulation adjuvants.

27. A weed control composition, which contains an effective amount of a compound in accordance with claim 19 and one or more formulation adjuvants.

28. A weed control composition, which contains an effective amount of a compound in accordance with claim 20 and one or more formulation adjuvants.

29. A weed control composition, which contains an effective amount of a compound in accordance with claim 21 and one or more formulation adjuvants.

30. A weed control composition, which contains an effective amount of a compound in accordance with claim 22 and one or more formulation adjuvants.

31. A method for the control of weeds, which method comprises treating the locus to be protected against weeds and/or the weeds with an effective amount of a composition in accordance with claim 23.

32. A method for the control of weeds, which method comprises treating the locus to be protected against weeds and/or the weeds with an effective amount of a composition in accordance with claim 26.

33. A method for the control of weeds, which method comprises treating the locus to be protected against weeds and/or the weeds with an effective amount of a composition in accordance with claim 27.

34. A method for the control of weeds, which method comprises treating the locus to be protected against weeds and/or the weeds with an effective amount of a composition in accordance with claim 28.

35. A method for the control of weeds, which method comprises treating the locus to be protected against weeds and/or the weeds with an effective amount of a composition in accordance with claim 29.

36. A method for the control of weeds, which method comprises treating the locus to be protected against weeds and/or the weeds with an effective amount of a composition in accordance with claim 30.

* * * * *

UNITED STATES PATENT AND TRADEMARK OFFICE
CERTIFICATE OF CORRECTION

PATENT NO. : 4,859,229

DATED : August 22, 1989

INVENTOR(S) : Jean Wenger, Paul Winternitz

It is certified that error appears in the above-identified patent and that said Letters Patent is hereby corrected as shown below:

In claim 1, column 56, line 44, after "$R^5$ and $R^6$" please insert -- tri- or--.

In claim 2, column 56, line 51, delete "phenoxy-C-4" and please insert --- phenoxy-$C_{1-4}$- ---;

In claim 13, column 57, line 29, "b" should be deleted at the beginning of the line;

In claim 14, column 58, line 27, delete "b" and insert --- 6 ---;

In claim 17, column 58, line 53, before "is" please insert --- $R^1$ ---;

In claim 19, column 59, line 1, "$R^1$" should be --- $R^{1'}$ ---; and

In claim 22, column 59, line 57, delete "$R^1$" and insert --- $R^{1'}$ ---.

Signed and Sealed this

Eighteenth Day of December, 1990

Attest:

HARRY F. MANBECK, JR.

*Attesting Officer*　　　　　*Commissioner of Patents and Trademarks*